(12) United States Patent
Emalfarb et al.

(10) Patent No.: US 7,399,627 B2
(45) Date of Patent: *Jul. 15, 2008

(54) TRANSFORMATION SYSTEM IN THE FIELD OF FILAMENTOUS FUNGAL HOSTS

(75) Inventors: Mark Aaron Emalfarb, Jupiter, FL (US); Richard Paul Burlingame, Manitowoc, WI (US); Philip Terry Olson, Manitowoc, WI (US); Arkady Panteleimonovich Sinitsyn, Moscow (RU); Martine Parriche, Toulouse (FR); Jean Christophe Bousson, Quint-Fonsegrives (FR); Christine Marie Pynnonen, Manitowoc, WI (US); Peter Jan Punt, Houten (NL); Cornelia Marie Johanna Van Zeijl, Vieuten-de Meern (NL)

(73) Assignee: Dyadic International (USA), Inc., Jupiter, FL (US)

( * ) Notice: Subject to any disclaimer, the term of this patent is extended or adjusted under 35 U.S.C. 154(b) by 723 days.

This patent is subject to a terminal disclaimer.

(21) Appl. No.: 10/394,568

(22) Filed: Mar. 21, 2003

(65) Prior Publication Data

US 2004/0002136 A1    Jan. 1, 2004

Related U.S. Application Data

(63) Continuation of application No. 09/548,938, filed on Apr. 13, 2000, now Pat. No. 6,573,086, which is a continuation-in-part of application No. PCT/NL99/00618, filed on Oct. 6, 1999, which is a continuation-in-part of application No. PCT/EP98/06496, filed on Oct. 6, 1998.

(51) Int. Cl.
   *C12N 1/15* (2006.01)
(52) U.S. Cl. .................... 435/254.11; 435/69.1
(58) Field of Classification Search .................. None
   See application file for complete search history.

(56) References Cited

U.S. PATENT DOCUMENTS 5,763,254 A    6/1998    Wöldike et al.
5,811,381 A *  9/1998    Emalfarb et al. ............ 510/320
6,573,086 B1 * 6/2003    Emalfrab et al. ........ 435/254.11

FOREIGN PATENT DOCUMENTS

| WO | WO 97/13853 | 4/1997 |
| WO | WO 97/27363 | 7/1997 |
| WO | WO 98/15633 | 4/1998 |
| WO | WO 00/20555 | 4/2000 |

OTHER PUBLICATIONS

Iikura Hiroshi, et al: "Cloning of a Gene Encoding a Putative Xylanase with a Cellulose-Binding Domain from *Humicola grisea*", *Bioscience Biotechnology And Biochemistry*, 61, No. 9, 1997, pp. 1593-1595.
Gunf-Fusox, accession No. p46239, Nov. 1, 1995, P.O. Sheppard, et. al.: "The Use of Conserved Cellulase Family-Specific Sequences to Clone Cellulase Homologue cDNAs from *Fusarium oxysporum*."
Accession No. o59937, Aug. 1, 1998, M.C. Ruiz-Roldan, et. al.: *Fusarium oxysporum* f.sp. lycopersici. family F xylanase (XYL3).
Accession No. D63515; Aug. 21, 1995, S. Takishima et al.: "Cloning, Sequencing, And Expression of the Cellulase Genes of *Humicola grisea* Var. Thermoidea."
P. O. Sheppard, et al:,*Gene*: 150, 1994, pp. 163-167.
Accession No. Q12621, Nov. 1, 1996, S. Takishima et al.: "Cloning, Sequencing, And Expression of the Cellulase Genes of *Humicola grisea* Var. Thermoidea."
K. Eriksson, et. al.: "Extracellular Enzyme System Utilized by the Fungus *Sporotrichum pulverulentum* (*Chrysosporium lignorum*) for the Breakdown of Cellulose." 1, Separation, Purification And Physico-Chemical Characterisation of Five Endo-1, 4-Beta-Glucanases *European Journal of Biochemistry*, 51, 1975, pp. 193-206.
COMMUNICATION, dated Dec. 28, 2000, European Search Report.

\* cited by examiner

*Primary Examiner*—James S Ketter
(74) *Attorney, Agent, or Firm*—Morgan & Finnegan, LLP

(57) ABSTRACT

A novel transformation system in the field of filamentous fungal hosts for expressing and secreting heterologous proteins or polypeptides is described. The invention also covers a process for producing large amounts of polypeptide or protein in an economical manner. The system comprises a transformed or transfected fungal strain of the genus *Chrysosporium*, more particularly of *Chrysosporium lucknowense* and mutants or derivatives thereof. It also covers transformants containing *Chrysosporium* coding sequences, as well expression-regulating sequences of *Chrysosporium* genes. Also provided are novel fungal enzymes and their encoding sequences and expression-regulating sequences.

6 Claims, 36 Drawing Sheets

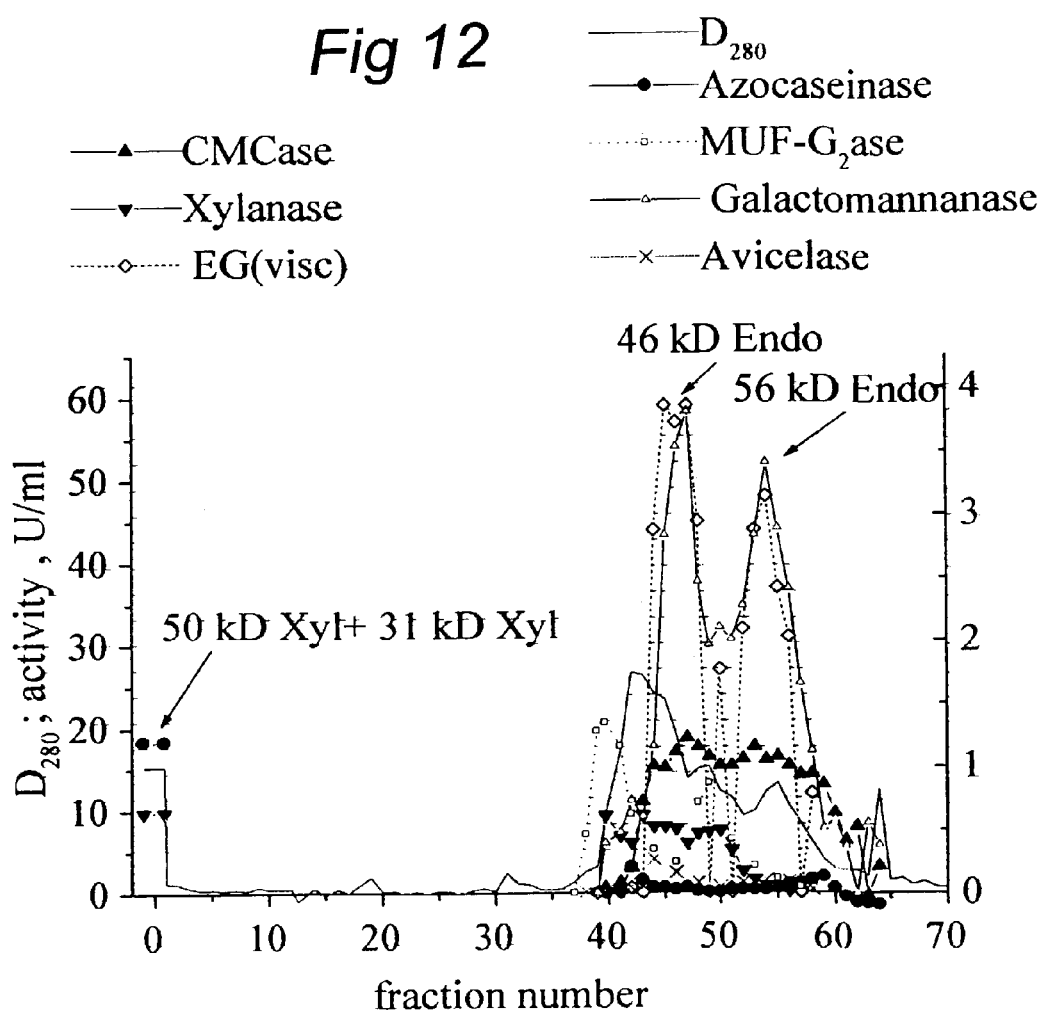

Fig 13a
45kD endo (pI 6.0)
Fig 13b
55 kD endo (pI 4.9)
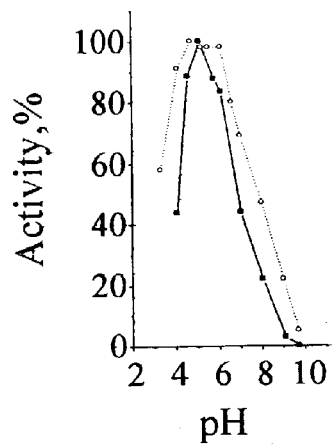
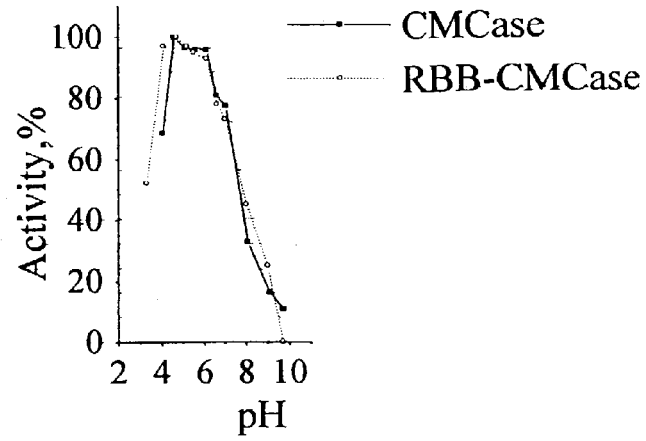
Fig 13c
30kD Xyl (pI 9.1)
Fig 13d
51kD Xyl (pI 8.7)
Fig 13e
60 kD Xyl (pI 4.7)
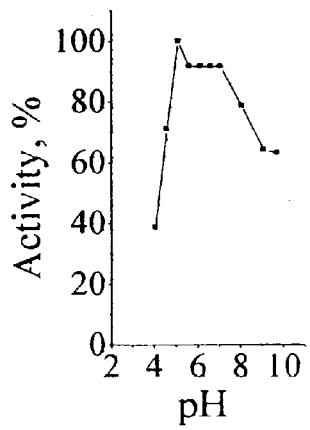
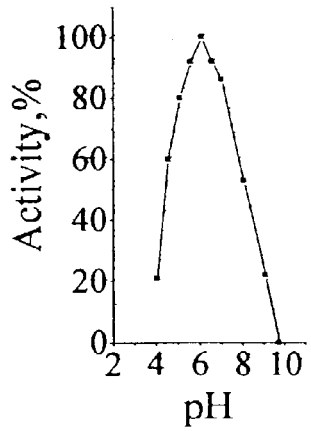
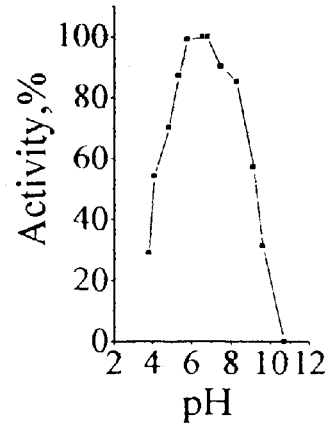

45 kD Endo (pI 6.0)

55 kD Endo (pI 4.9)

30 kD Xyl (pI 9.1)

51 kD Xyl (pI 8.7)

Fig 16a
45 kD endo (pI 6.0)
Fig 16b
55kD endo (pI 4.9)
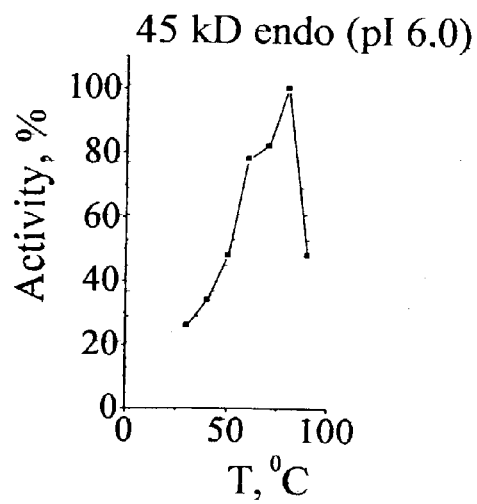
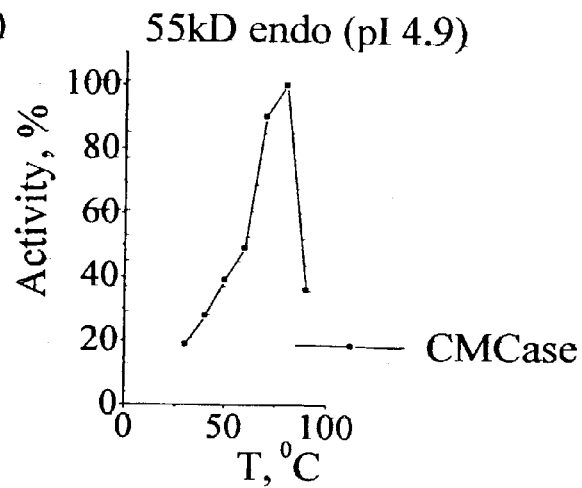
Fig 16c
30 kD Xyl (pI 9.1)
Fig 16d
51 kD Xyl (pI 8.7)
Fig 16e
60 kD Xyl (pI 4.7)
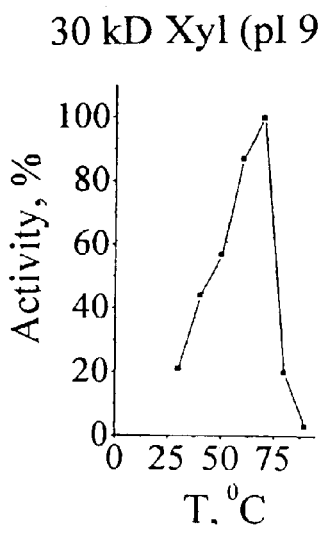
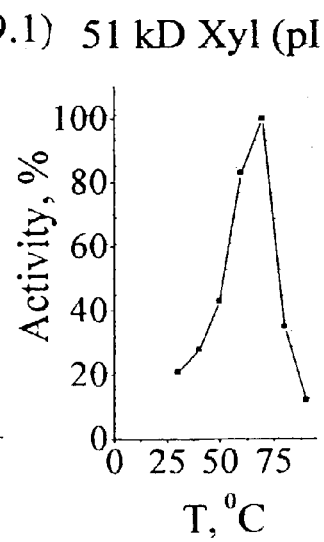
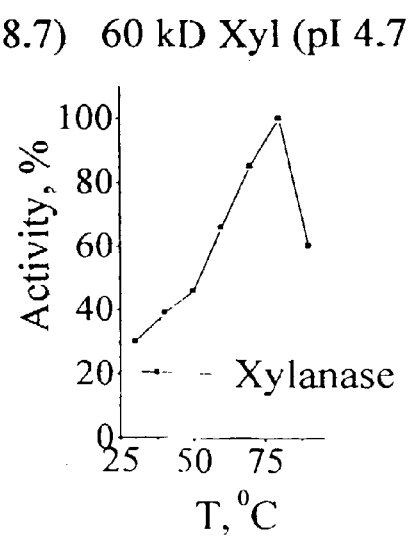

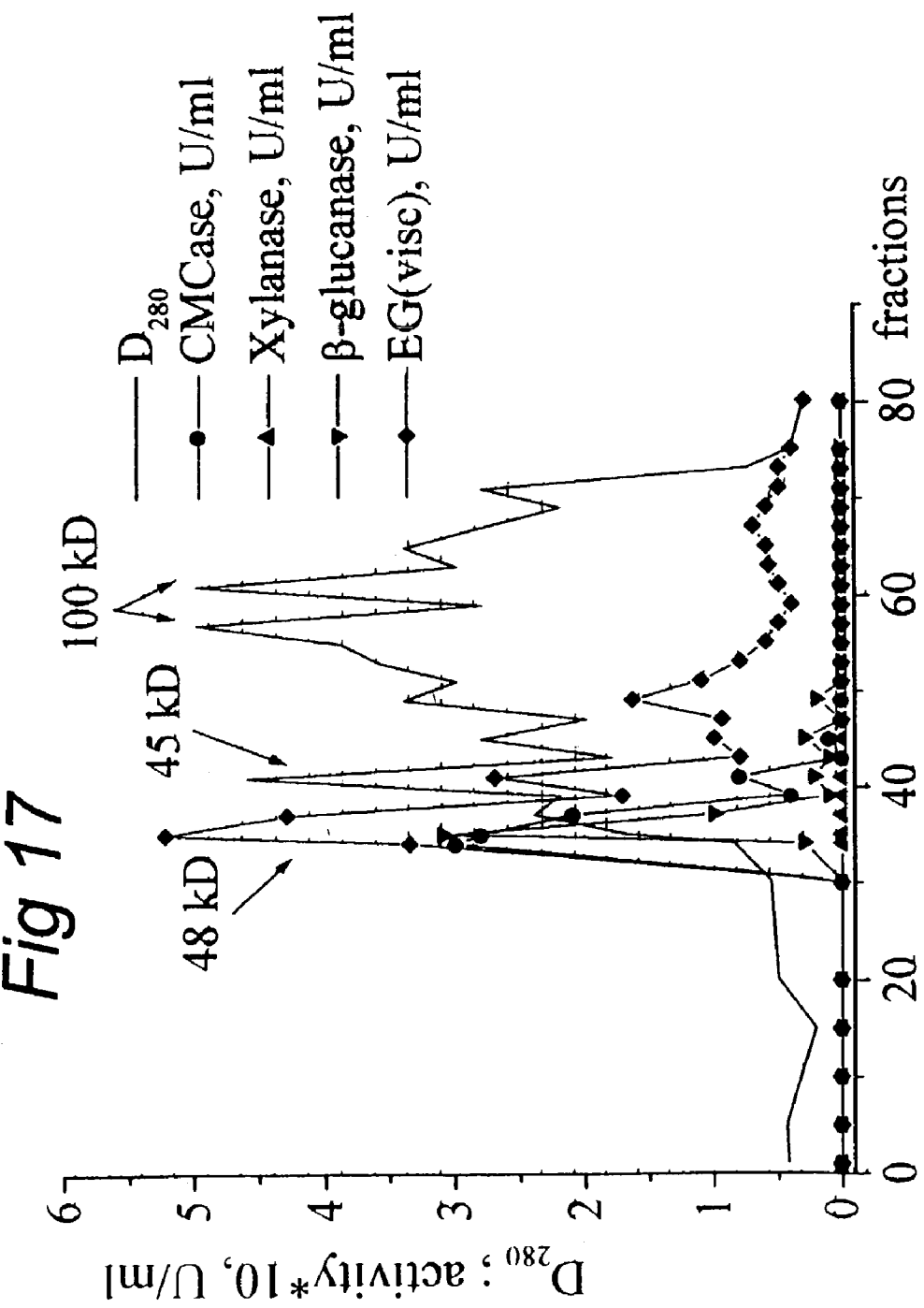

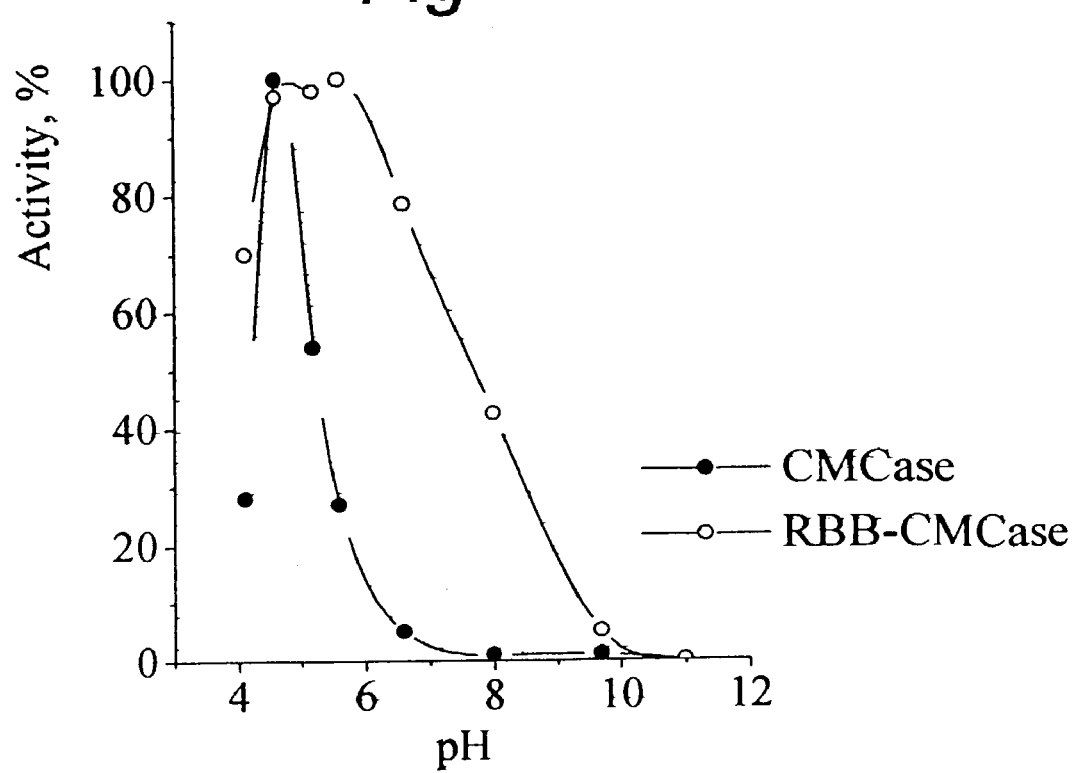

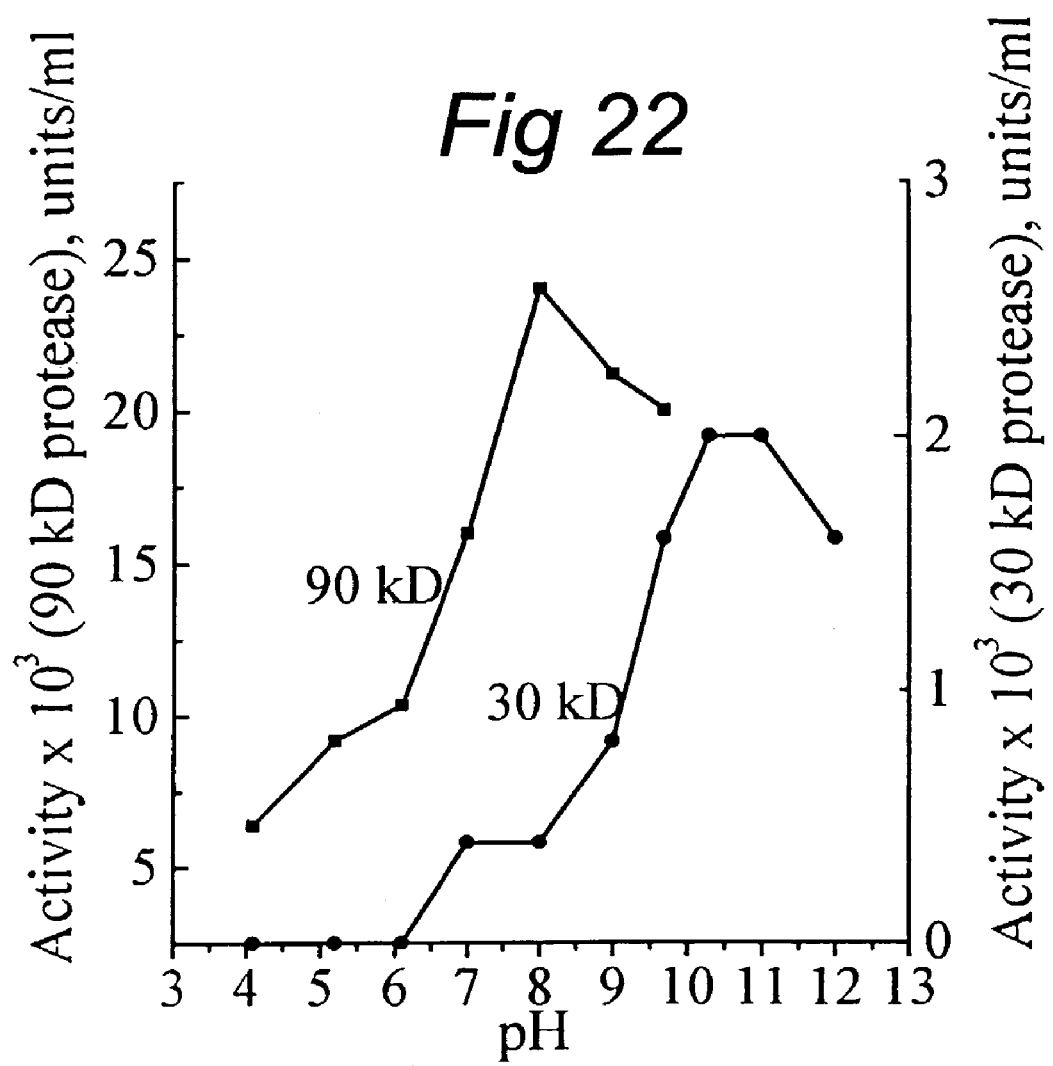

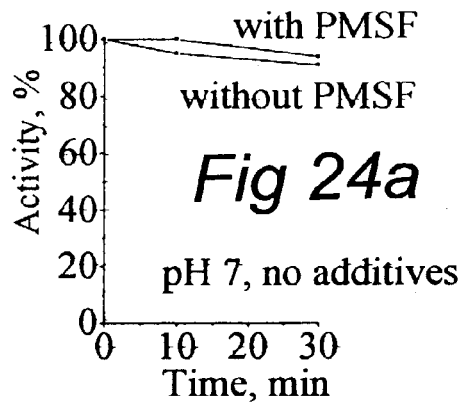
Fig 24a — pH 7, no additives
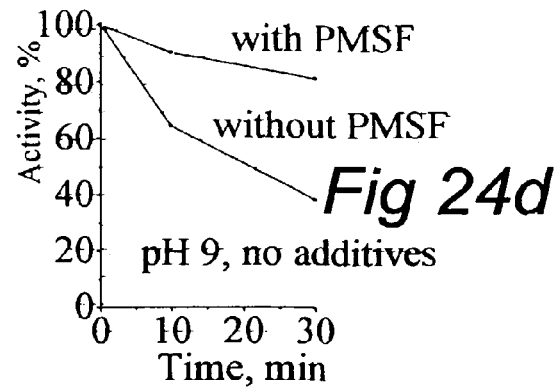
Fig 24d — pH 9, no additives
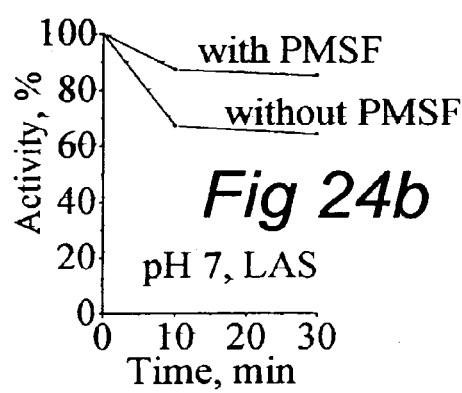
Fig 24b — pH 7, LAS
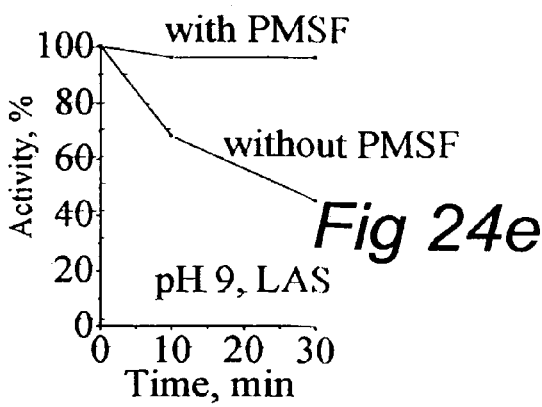
Fig 24e — pH 9, LAS
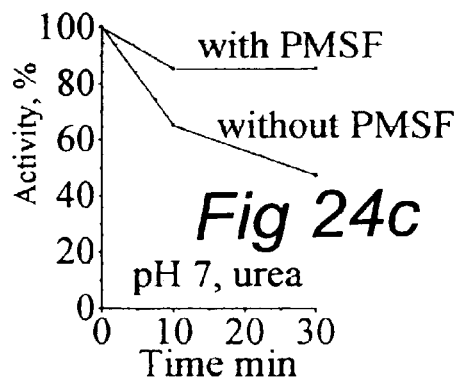
Fig 24c — pH 7, urea
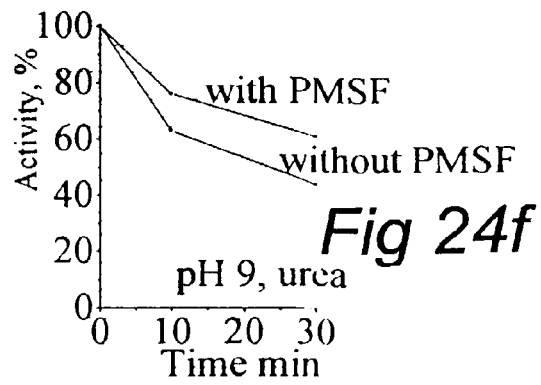
Fig 24f — pH 9, urea

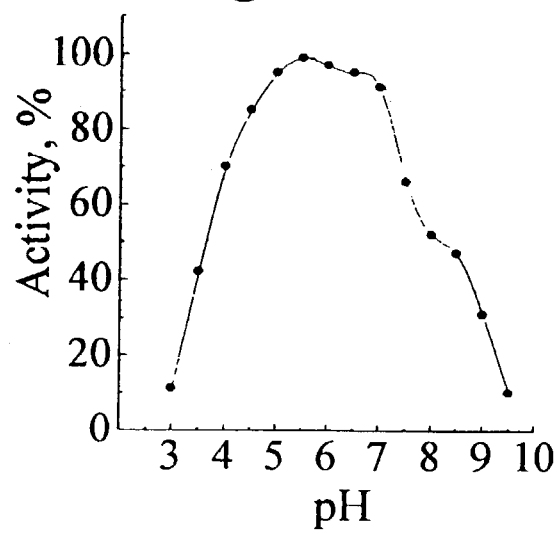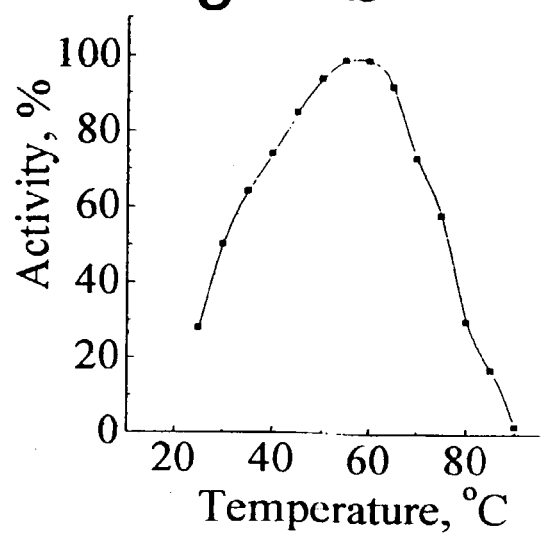
Fig 26a
Fig 26b

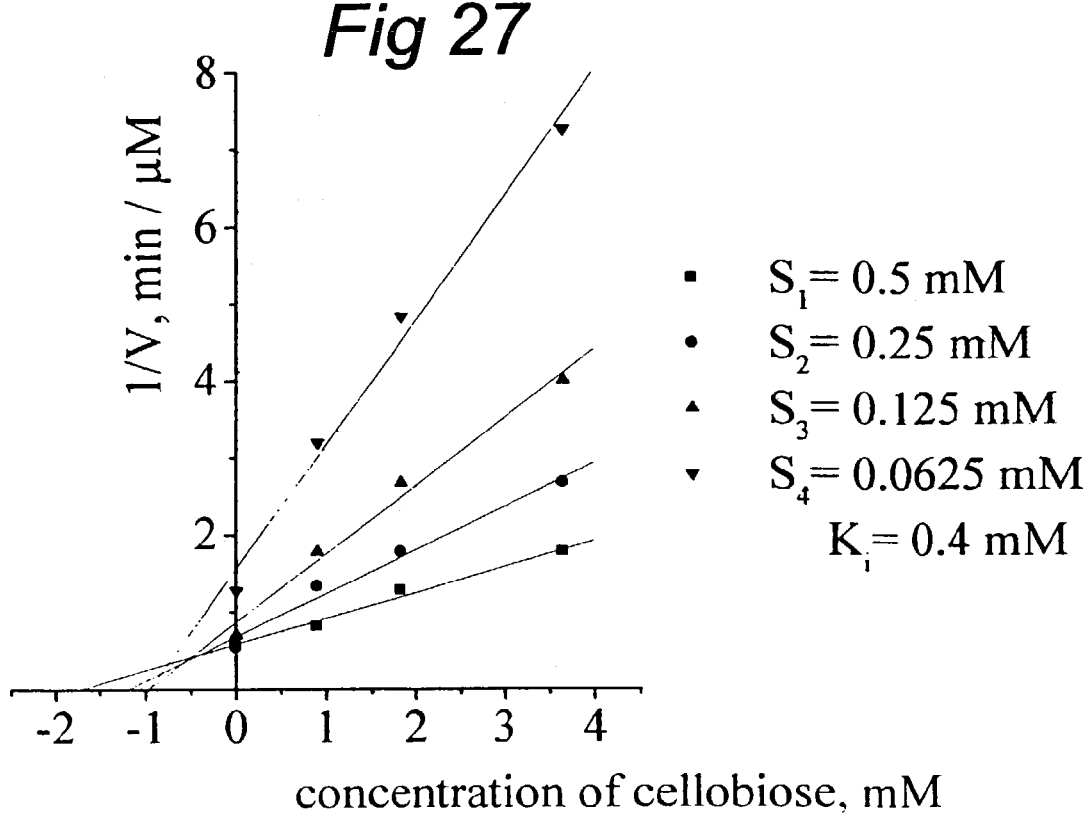

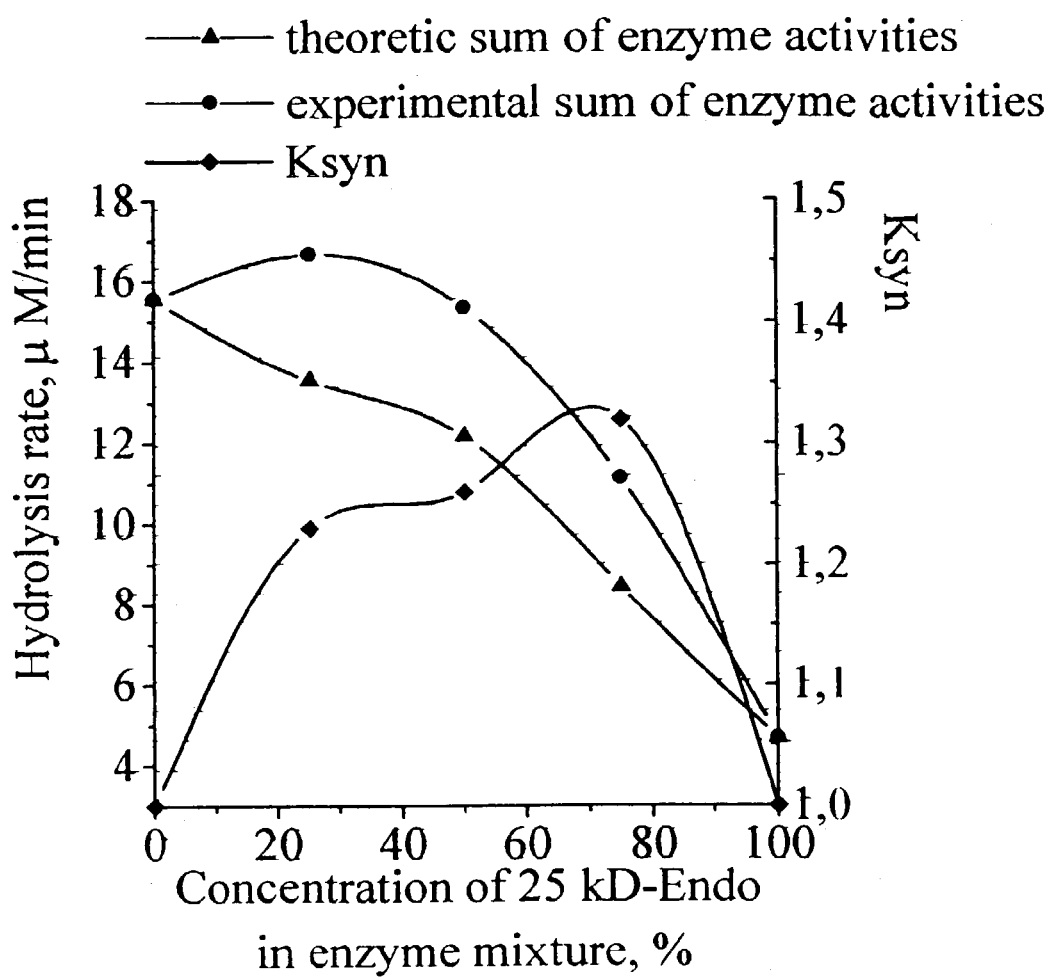

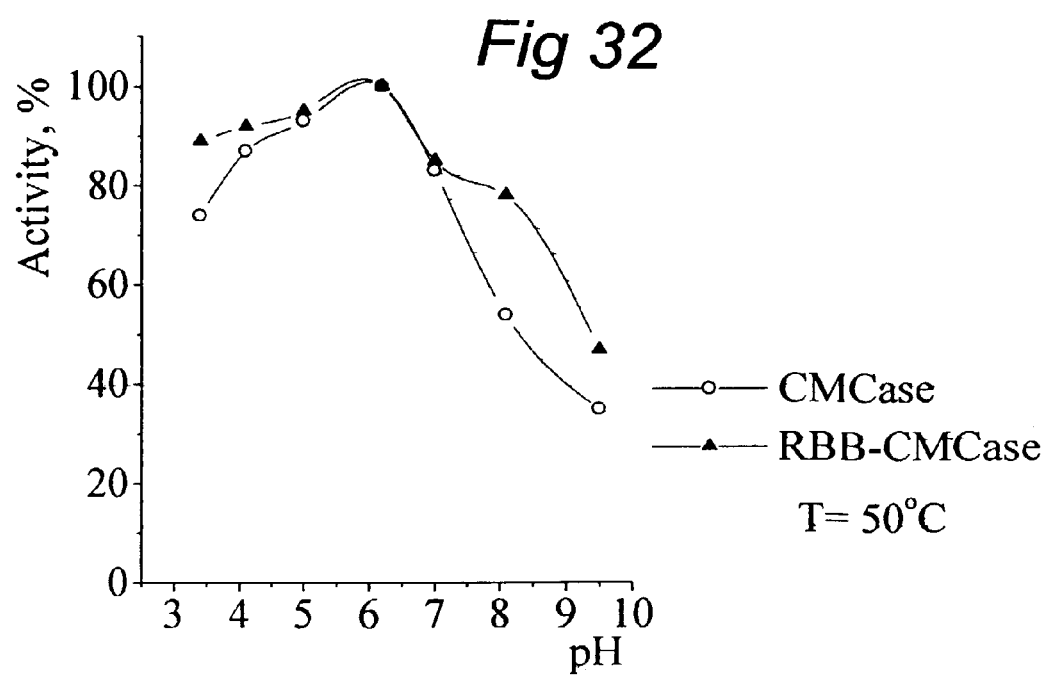

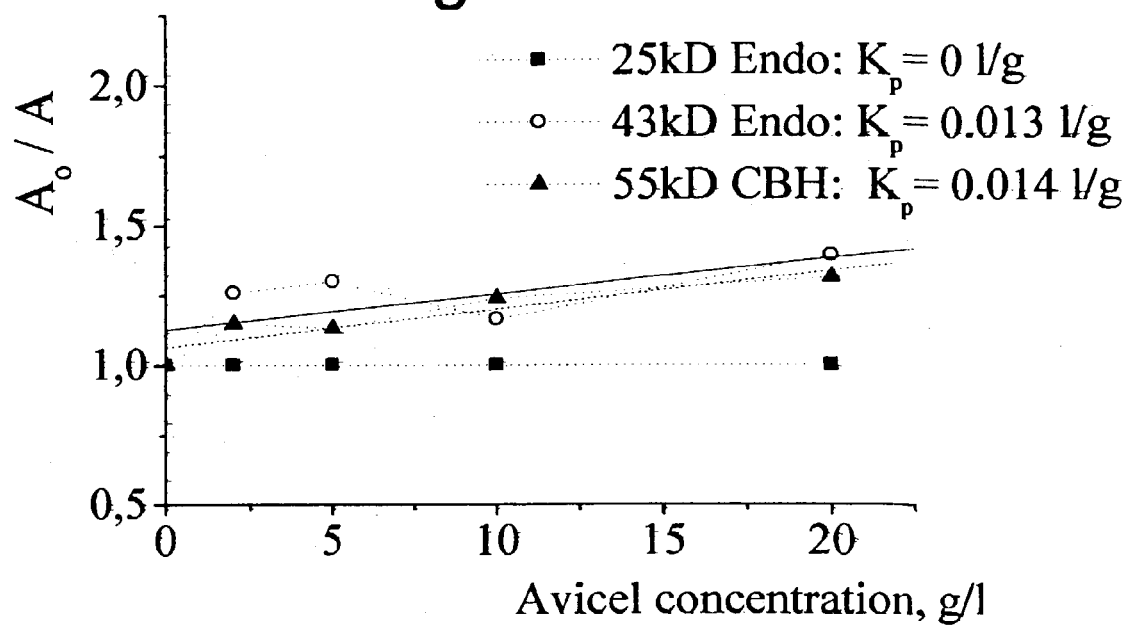

SEQUENCE LISTING

<160> NUMBER OF SEQ ID NOS: 12

<210> SEQ ID NO 1
<211> LENGTH: 1570
<212> TYPE: DNA
<213> ORGANISM: Homo sapiens
<220> FEATURE:
<221> NAME/KEY: CDS
<222> LOCATION: (126)..(1523)

<400> SEQUENCE: 1

```
gtcgacgttg caggctgagt catcactaga gagtgggaag ggcagcagca gcagagaatc         60
caaaccctaa agctgatatc acaaagtacc atttctccaa gttgggggct cagaggggag        120 tcatc atg agc gat gtt acc att gtg aaa gaa ggt tgg gtt cag aag agg       170
      Met Ser Asp Val Thr Ile Val Lys Glu Gly Trp Val Gln Lys Arg
        1               5                  10                  15 gga gaa tat ata aaa aac tgg agg cca aga tac ttc ctt ttg aag aca         218
Gly Glu Tyr Ile Lys Asn Trp Arg Pro Arg Tyr Phe Leu Leu Lys Thr
             20                  25                  30 gat ggc tca ttc ata gga tat aaa gag aaa cct caa gat gtg gat tta         266
Asp Gly Ser Phe Ile Gly Tyr Lys Glu Lys Pro Gln Asp Val Asp Leu
         35                  40                  45 cct tat ccc ctc aac aac ttt tca gtg gca aaa tgc cag tta atg aaa         314
Pro Tyr Pro Leu Asn Asn Phe Ser Val Ala Lys Cys Gln Leu Met Lys
     50                  55                  60 aca gaa cga cca aag cca aac aca ttt ata atc aga tgt ctc cag tgg         362
Thr Glu Arg Pro Lys Pro Asn Thr Phe Ile Ile Arg Cys Leu Gln Trp
 65                  70                  75 act act gtt ata gag aga aca ttt cat gta gat act cca gag gaa agg         410
Thr Thr Val Ile Glu Arg Thr Phe His Val Asp Thr Pro Glu Glu Arg
 80                  85                  90                  95 gaa gaa tgg aca gaa gct atc cag gct gta gca gac aga ctg cag agg         458
Glu Glu Trp Thr Glu Ala Ile Gln Ala Val Ala Asp Arg Leu Gln Arg
                100                 105                 110 caa gaa gag gag aga atg aat tgt agt cca act tca caa att gat aat         506
Gln Glu Glu Glu Arg Met Asn Cys Ser Pro Thr Ser Gln Ile Asp Asn
            115                 120                 125 ata gga gag gaa gag atg gat gcc tct aca acc cat cat aaa aga aag         554
Ile Gly Glu Glu Glu Met Asp Ala Ser Thr Thr His His Lys Arg Lys
        130                 135                 140 aca atg aat gat ttt gac tat ttg aaa cta cta ggt aaa ggc act ttt         602
Thr Met Asn Asp Phe Asp Tyr Leu Lys Leu Leu Gly Lys Gly Thr Phe
    145                 150                 155 ggg aaa gtt att ttg gtt cga gag aag gca agt gga aaa tac tat gct         650
Gly Lys Val Ile Leu Val Arg Glu Lys Ala Ser Gly Lys Tyr Tyr Ala
160                 165                 170                 175 atg aag att ctg aag aaa gaa gtc att att gca aag gat gaa gtg gca         698
Met Lys Ile Leu Lys Lys Glu Val Ile Ile Ala Lys Asp Glu Val Ala
                180                 185                 190 cac act cta act gaa agc aga gta tta aag aac act aga cat ccc ttt         746
His Thr Leu Thr Glu Ser Arg Val Leu Lys Asn Thr Arg His Pro Phe
            195                 200                 205 tta aca tcc ttg aaa tat tcc ttc cag aca aaa gac cgt ttg tgt ttt         794
Leu Thr Ser Leu Lys Tyr Ser Phe Gln Thr Lys Asp Arg Leu Cys Phe
        210                 215                 220 gtg atg gaa tat gtt aat ggg ggc gag ctg ttt ttc cat ttg tcg aga         842
Val Met Glu Tyr Val Asn Gly Gly Glu Leu Phe Phe His Leu Ser Arg
    225                 230                 235
```

```
gag cgg gtg ttc tct gag gac cgc aca cgt ttc tat ggt gca gaa att     890
Glu Arg Val Phe Ser Glu Asp Arg Thr Arg Phe Tyr Gly Ala Glu Ile
240                 245                 250                 255 gtc tct gcc ttg gac tat cta cat tcc gga aag att gtg tac cgt gat     938
Val Ser Ala Leu Asp Tyr Leu His Ser Gly Lys Ile Val Tyr Arg Asp
                260                 265                 270 ctc aag ttg gag aat cta atg ctg gac aaa gat ggc cac ata aaa att     986
Leu Lys Leu Glu Asn Leu Met Leu Asp Lys Asp Gly His Ile Lys Ile
        275                 280                 285 aca gat ttt gga ctt tgc aaa gaa ggg atc aca gat gca gcc acc atg    1034
Thr Asp Phe Gly Leu Cys Lys Glu Gly Ile Thr Asp Ala Ala Thr Met
            290                 295                 300 aag aca ttc tgt ggc act cca gaa tat ctg gca cca gag gtg tta gaa    1082
Lys Thr Phe Cys Gly Thr Pro Glu Tyr Leu Ala Pro Glu Val Leu Glu
305                 310                 315 gat aat gac tat ggc cga gca gta gac tgg tgg ggc cta ggg gtt gtc    1130
Asp Asn Asp Tyr Gly Arg Ala Val Asp Trp Trp Gly Leu Gly Val Val
320                 325                 330                 335 atg tat gaa atg atg tgt ggg agg tta cct ttc tac aac cag gac cat    1178
Met Tyr Glu Met Met Cys Gly Arg Leu Pro Phe Tyr Asn Gln Asp His
                340                 345                 350 gag aaa ctt ttt gaa tta ata tta atg gaa gac att aaa ttt cct cga    1226
Glu Lys Leu Phe Glu Leu Ile Leu Met Glu Asp Ile Lys Phe Pro Arg
        355                 360                 365 aca ctc tct tca gat gca aaa tca ttg ctt tca ggg ctc ttg ata aag    1274
Thr Leu Ser Ser Asp Ala Lys Ser Leu Leu Ser Gly Leu Leu Ile Lys
            370                 375                 380 gat cca aat aaa cgc ctt ggt gga gga cca gat gat gca aaa gaa att    1322
Asp Pro Asn Lys Arg Leu Gly Gly Gly Pro Asp Asp Ala Lys Glu Ile
385                 390                 395 atg aga cac agt ttc ttc tct gga gta aac tgg caa gat gta tat gat    1370
Met Arg His Ser Phe Phe Ser Gly Val Asn Trp Gln Asp Val Tyr Asp
400                 405                 410                 415 aaa aag ctt gta cct cct ttt aaa cct caa gta aca tct gag aca gat    1418
Lys Lys Leu Val Pro Pro Phe Lys Pro Gln Val Thr Ser Glu Thr Asp
                420                 425                 430 act aga tat ttt gat gaa gaa ttt aca gct cag act att aca ata aca    1466
Thr Arg Tyr Phe Asp Glu Glu Phe Thr Ala Gln Thr Ile Thr Ile Thr
        435                 440                 445 cca cct gaa aaa tgt cag caa tca gat tgt ggc atg ctg ggt aac tgg    1514
Pro Pro Glu Lys Cys Gln Gln Ser Asp Cys Gly Met Leu Gly Asn Trp
            450                 455                 460 aaa aaa taa taaaaagtaa gtttcaatag ctaaaaaaa aaaaaaaaa aaaaaa       1570
Lys Lys
    465

<210> SEQ ID NO 2
<211> LENGTH: 465
<212> TYPE: PRT
<213> ORGANISM: Homo sapiens

<400> SEQUENCE: 2

Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
            20                  25                  30

Gly Ser Phe Ile Gly Tyr Lys Glu Lys Pro Gln Asp Val Asp Leu Pro
        35                  40                  45

Tyr Pro Leu Asn Asn Phe Ser Val Ala Lys Cys Gln Leu Met Lys Thr
    50                  55                  60
```

```
Glu Arg Pro Lys Pro Asn Thr Phe Ile Ile Arg Cys Leu Gln Trp Thr
 65                  70                  75                  80

Thr Val Ile Glu Arg Thr Phe His Val Asp Thr Pro Glu Arg Glu
                 85                  90                  95

Glu Trp Thr Glu Ala Ile Gln Ala Val Ala Asp Arg Leu Gln Arg Gln
            100                 105                 110

Glu Glu Glu Arg Met Asn Cys Ser Pro Thr Ser Gln Ile Asp Asn Ile
            115                 120                 125

Gly Glu Glu Met Asp Ala Ser Thr Thr His His Lys Arg Lys Thr
130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175

Lys Ile Leu Lys Lys Glu Val Ile Ile Ala Lys Asp Glu Val Ala His
                180                 185                 190

Thr Leu Thr Glu Ser Arg Val Leu Lys Asn Thr Arg His Pro Phe Leu
            195                 200                 205

Thr Ser Leu Lys Tyr Ser Phe Gln Thr Lys Asp Arg Leu Cys Phe Val
    210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
                260                 265                 270

Lys Leu Glu Asn Leu Met Leu Asp Lys Asp Gly His Ile Lys Ile Thr
            275                 280                 285

Asp Phe Gly Leu Cys Lys Glu Gly Ile Thr Asp Ala Ala Thr Met Lys
290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
                325                 330                 335

Tyr Glu Met Met Cys Gly Arg Leu Pro Phe Tyr Asn Gln Asp His Glu
                340                 345                 350

Lys Leu Phe Glu Leu Ile Leu Met Glu Asp Ile Lys Phe Pro Arg Thr
            355                 360                 365

Leu Ser Ser Asp Ala Lys Ser Leu Leu Ser Gly Leu Leu Ile Lys Asp
370                 375                 380

Pro Asn Lys Arg Leu Gly Gly Gly Pro Asp Asp Ala Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
                420                 425                 430

Arg Tyr Phe Asp Glu Glu Phe Thr Ala Gln Thr Ile Thr Ile Thr Pro
            435                 440                 445

Pro Glu Lys Cys Gln Gln Ser Asp Cys Gly Met Leu Gly Asn Trp Lys
    450                 455                 460

Lys
465
```

```
<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:Synthethic
      Oligonucleotide Primers

<400> SEQUENCE: 3
tccaaaccct aaagctgata tcac                                           24

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:Synthetic
      Oligonucleotide Primers

<400> SEQUENCE: 4
cctggatagc ttctgtccat tc                                             22

<210> SEQ ID NO 5
<211> LENGTH: 74
<212> TYPE: DNA
<213> ORGANISM: Artificial Sequence
<220> FEATURE:
<223> OTHER INFORMATION: Description of Artificial Sequence:Synthetic
      Oligonucleotide Primers

<400> SEQUENCE: 5
atgagcgatg ttaccattgt gaaagaaggt tgggttcaga agaggggaga atatataaaa    60
aactggaggc caag                                                      74

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:Synthetic
      Oligonucleotide Primers

<400> SEQUENCE: 6
ttattttttc caggtaccca gcatgcc                                        27

<210> SEQ ID NO 7
<211> LENGTH: 90
<212> TYPE: DNA
<213> ORGANISM: Artificial Sequence
<220> FEATURE:
<223> OTHER INFORMATION: Description of Artificial Sequence:Synthetic
      Oligonucleotide Primers

<400> SEQUENCE: 7
gcgcgcgaat tccaccatg ggtagcaaca agagcaagcc caaggatgcc agccagcggc     60
gccgcagcag cgatgttacc attgtgaaag                                     90

<210> SEQ ID NO 8
<211> LENGTH: 66
<212> TYPE: DNA
<213> ORGANISM: Artificial Sequence
<220> FEATURE:
<223> OTHER INFORMATION: Description of Artificial Sequence:Synthetic
      Oligonucleotide Primers

<400> SEQUENCE: 8
```

```
gcgcgcgggc ccttaggcgt agtcggggac gtcgtacggg tattttttcc agttacccag    60
catgcc                                                               66
```

<210> SEQ ID NO 9
<211> LENGTH: 51
<212> TYPE: DNA
<213> ORGANISM: Artificial Sequence
<220> FEATURE:
<223> OTHER INFORMATION: Description of Artificial Sequence:Synthetic
      Oligonucleotide Primers

<400> SEQUENCE: 9

```
cggggtacca ccatgggtag caacaagagc aagcccaagg atgccagcca g             51
```

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:Synthetic
      Oligonucleotide Primers

<400> SEQUENCE: 10

```
ccggaattct taggcgtagt cggggacgtc                                    30
```

<210> SEQ ID NO 11
<211> LENGTH: 480
<212> TYPE: PRT
<213> ORGANISM: Homo sapiens

<400> SEQUENCE: 11

| Met | Asn | Glu | Val | Ser | Val | Ile | Lys | Glu | Gly | Trp | Leu | His | Lys | Arg | Gly |
|---|---|---|---|---|---|---|---|---|---|---|---|---|---|---|---|
| 1 | | | | 5 | | | | | 10 | | | | | 15 | |

| Glu | Tyr | Ile | Lys | Thr | Trp | Arg | Pro | Arg | Tyr | Phe | Leu | Leu | Lys | Ser | Asp |
|---|---|---|---|---|---|---|---|---|---|---|---|---|---|---|---|
| | | | 20 | | | | | 25 | | | | | 30 | | |

| Gly | Ser | Phe | Ile | Gly | Tyr | Lys | Glu | Arg | Pro | Glu | Ala | Pro | Asp | Gln | Thr |
|---|---|---|---|---|---|---|---|---|---|---|---|---|---|---|---|
| | | | 35 | | | | | 40 | | | | | 45 | | |

| Leu | Pro | Pro | Leu | Asn | Asn | Phe | Ser | Val | Ala | Glu | Cys | Gln | Leu | Met | Lys |
|---|---|---|---|---|---|---|---|---|---|---|---|---|---|---|---|
| | 50 | | | | | 55 | | | | | 60 | | | | |

| Thr | Glu | Arg | Pro | Arg | Pro | Asn | Thr | Phe | Val | Ile | Arg | Cys | Leu | Gln | Trp |
|---|---|---|---|---|---|---|---|---|---|---|---|---|---|---|---|
| 65 | | | | | 70 | | | | | 75 | | | | | 80 |

| Thr | Thr | Val | Ile | Glu | Arg | Thr | Phe | His | Val | Asp | Ser | Pro | Asp | Glu | Arg |
|---|---|---|---|---|---|---|---|---|---|---|---|---|---|---|---|
| | | | | 85 | | | | | 90 | | | | | 95 | |

| Glu | Glu | Trp | Met | Arg | Ala | Ile | Gln | Met | Val | Ala | Asn | Ser | Leu | Lys | Gln |
|---|---|---|---|---|---|---|---|---|---|---|---|---|---|---|---|
| | | | 100 | | | | | 105 | | | | | 110 | | |

| Arg | Ala | Pro | Gly | Glu | Asp | Pro | Met | Asp | Tyr | Lys | Cys | Gly | Ser | Pro | Ser |
|---|---|---|---|---|---|---|---|---|---|---|---|---|---|---|---|
| | | | 115 | | | | | 120 | | | | | 125 | | |

| Asp | Ser | Ser | Thr | Thr | Glu | Glu | Met | Glu | Val | Ala | Val | Ser | Lys | Ala | Arg |
|---|---|---|---|---|---|---|---|---|---|---|---|---|---|---|---|
| | 130 | | | | | 135 | | | | | 140 | | | | |

| Ala | Lys | Val | Thr | Met | Asn | Asp | Phe | Asp | Tyr | Leu | Lys | Leu | Leu | Gly | Lys |
|---|---|---|---|---|---|---|---|---|---|---|---|---|---|---|---|
| 145 | | | | | 150 | | | | | 155 | | | | | 160 |

| Gly | Thr | Phe | Gly | Lys | Val | Ile | Leu | Val | Arg | Glu | Lys | Ala | Thr | Gly | Arg |
|---|---|---|---|---|---|---|---|---|---|---|---|---|---|---|---|
| | | | | 165 | | | | | 170 | | | | | 175 | |

| Tyr | Tyr | Ala | Met | Lys | Ile | Leu | Arg | Lys | Glu | Val | Ile | Ile | Ala | Lys | Asp |
|---|---|---|---|---|---|---|---|---|---|---|---|---|---|---|---|
| | | | 180 | | | | | 185 | | | | | 190 | | |

| Glu | Val | Ala | His | Thr | Val | Thr | Glu | Ser | Arg | Val | Leu | Gln | Asn | Thr | Arg |
|---|---|---|---|---|---|---|---|---|---|---|---|---|---|---|---|
| | | | 195 | | | | | 200 | | | | | 205 | | |

His Pro Phe Leu Thr Ala Leu Lys Tyr Ala Phe Gln Thr His Asp Arg

-continued

```
              210                 215                 220
Leu Cys Phe Val Met Glu Tyr Ala Asn Gly Gly Glu Leu Phe His
225                 230                 235                 240

Leu Ser Arg Glu Arg Val Phe Thr Glu Glu Arg Ala Arg Phe Tyr Gly
                245                 250                 255

Ala Glu Ile Val Ser Ala Leu Glu Tyr Leu His Ser Arg Asp Val Val
                260                 265                 270

Tyr Arg Asp Ile Lys Leu Glu Asn Leu Met Leu Asp Lys Asp Gly His
                275                 280                 285

Ile Lys Ile Thr Asp Phe Gly Leu Cys Lys Glu Gly Ile Ser Asp Gly
290                 295                 300

Ala Thr Met Lys Thr Phe Cys Gly Thr Pro Glu Tyr Leu Ala Pro Glu
305                 310                 315                 320

Val Leu Glu Asp Asn Asp Tyr Gly Arg Ala Val Asp Trp Trp Gly Leu
                325                 330                 335

Gly Val Val Met Tyr Glu Met Met Cys Gly Arg Leu Pro Phe Tyr Asn
                340                 345                 350

Gln Asp His Glu Arg Leu Phe Glu Leu Ile Leu Met Glu Glu Ile Arg
                355                 360                 365

Phe Pro Arg Thr Leu Ser Pro Glu Ala Lys Ser Leu Leu Ala Gly Leu
370                 375                 380

Leu Lys Lys Asp Pro Lys Gln Arg Leu Gly Gly Gly Pro Ser Asp Ala
385                 390                 395                 400

Lys Glu Val Met Glu His Arg Phe Phe Leu Ser Ile Asn Trp Gln Asp
                405                 410                 415

Val Val Gln Lys Lys Leu Leu Pro Pro Phe Lys Pro Gln Val Thr Ser
                420                 425                 430

Glu Val Asp Thr Arg Tyr Phe Asp Asp Glu Phe Thr Ala Gln Ser Ile
                435                 440                 445

Thr Ile Thr Pro Pro Asp Arg Tyr Asp Ser Leu Gly Leu Leu Glu Leu
450                 455                 460

Asp Gln Arg Thr His Phe Pro Gln Phe Ser Tyr Ser Ala Ser Ile Arg
465                 470                 475                 480

<210> SEQ ID NO 12
<211> LENGTH: 465
<212> TYPE: PRT
<213> ORGANISM: Homo sapiens

<400> SEQUENCE: 12

Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
                20                  25                  30

Gly Ser Phe Ile Gly Tyr Lys Glu Lys Pro Gln Asp Val Asp Leu Pro
            35                  40                  45

Tyr Pro Leu Asn Asn Phe Ser Val Ala Lys Cys Gln Leu Met Lys Thr
        50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
                85                  90                  95

Glu Trp Thr Glu Ala Ile Gln Ala Val Ala Asp Arg Leu Gln Arg Gln
                100                 105                 110
```

-continued

```
Glu Glu Glu Arg Met Asn Cys Ser Pro Thr Ser Gln Ile Asp Asn Ile
            115                 120                 125

Gly Glu Glu Glu Met Asp Ala Ser Thr Thr His His Lys Arg Lys Thr
130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175

Lys Ile Leu Lys Lys Glu Val Ile Ile Ala Lys Asp Glu Val Ala His
            180                 185                 190

Thr Leu Thr Glu Ser Arg Val Leu Lys Asn Thr Arg His Pro Phe Leu
        195                 200                 205

Thr Ser Leu Lys Tyr Ser Phe Gln Thr Lys Asp Arg Leu Cys Phe Val
210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
            260                 265                 270

Lys Leu Glu Asn Leu Met Leu Asp Lys Asp Gly His Ile Lys Ile Thr
        275                 280                 285

Asp Phe Gly Leu Cys Lys Glu Gly Ile Thr Asp Ala Ala Thr Met Lys
290                 295                 300

Thr Phe Cys Gly Thr Pro Glu Tyr Leu Ala Pro Glu Val Leu Glu Asp
305                 310                 315                 320

Asn Asp Tyr Gly Arg Ala Val Asp Trp Trp Gly Leu Gly Val Val Met
                325                 330                 335

Tyr Glu Met Met Cys Gly Arg Leu Pro Phe Tyr Asn Gln Asp His Glu
            340                 345                 350

Lys Leu Phe Glu Leu Ile Leu Met Glu Asp Ile Lys Phe Pro Arg Thr
        355                 360                 365

Leu Ser Ser Asp Ala Lys Ser Leu Leu Ser Gly Leu Leu Ile Lys Asp
370                 375                 380

Pro Asn Lys Arg Leu Gly Gly Gly Pro Asp Asp Ala Lys Glu Ile Met
385                 390                 395                 400

Arg His Ser Phe Phe Ser Gly Val Asn Trp Gln Asp Val Tyr Asp Lys
                405                 410                 415

Lys Leu Val Pro Pro Phe Lys Pro Gln Val Thr Ser Glu Thr Asp Thr
            420                 425                 430

Arg Tyr Phe Asp Glu Glu Phe Thr Ala Gln Thr Ile Thr Ile Thr Pro
        435                 440                 445

Pro Glu Lys Cys Gln Gln Ser Asp Cys Gly Met Leu Gly Asn Trp Lys
450                 455                 460

Lys
465
```

TRANSFORMATION SYSTEM IN THE FIELD OF FILAMENTOUS FUNGAL HOSTS

REFERENCE TO PRIOR APPLICATIONS

This application is a continuation of application Ser. No. 09/548,938, filed Apr. 13, 2000, now U.S. Pat. No. 6,573,086, which is a continuation-in-part of international application PCT/NL99/00618, filed Oct. 6, 1999, which is a continuation-in-part of international application PCT/EP98/06496, filed Oct. 6, 1998.

SUMMARY OF THE INVENTION

The subject invention pertains to a novel transformation system in the field of filamentous fungal hosts for expressing and secreting heterologous proteins or polypeptides. The invention also covers a process for producing large amounts of polypeptide in an economical manner. The system comprises a transformed or transfected fungal strain of the genus *Chrysosporium*, more particularly of *Chrysosporium lucknowense* and mutants or derivatives thereof. It also covers transformants containing *Chrysosporium* coding sequences. Novel mutant *Chrysosporium* strains are disclosed as are novel enzymes derived therefrom. The subject invention further relates to novel enzymes derived from filamentous fungi, especially from strains of the genus *Chrysosporium*, and to coding sequences and expression-regulating sequences for these enzymes.

BACKGROUND TO THE INVENTION

A number of hosts for gene expression and methods of transformation have been disclosed in the prior art. Bacteria are often mentioned e.g. *Escherichia coli. E. coli* is however a micro-organism incapable of secretion of a number of proteins or polypeptides and as such is undesirable as host cell for production of protein or polypeptide at the industrial level. An additional disadvantage for *E. coli*, which is valid also for bacteria in general, is that prokaryotes cannot provide additional modifications required for numerous eukaryotic proteins or polypeptides to be produced in an active form. Glycosylation of proteins and proper folding of proteins are examples of processing required to ensure an active protein or polypeptide is produced. To ensure such processing one can sometimes use mammalian cells; however, the disadvantage of such cells is that they are often difficult to maintain and require expensive media. Such transformation systems are therefore not practical for production of proteins or polypeptides at the industrial level. They may be cost efficient for highly priced pharmaceutical compounds requiring relatively low amounts, but certainly not for industrial enzymes.

A number of fungal expression systems have been developed e.g. *Aspergillus niger, Aspergillus awamori, Aspergillus nidulans, Trichoderma reesei*. A number of others have been suggested but for various reasons have not found wide-spread acceptance or use. In general terms the ideal host must fulfill a large number of criteria:

The ideal host must be readily fermented using inexpensive medium.

The ideal host should use the medium efficiently.

The ideal host must produce the polypeptide or protein in high yield, i.e. must exhibit high protein to biomass ratio.

The ideal host should be capable of efficient secretion of the protein or polypeptide.

The ideal host must enable ease of isolation and purification of the desired protein or polypeptide.

The ideal host must process the desired protein or polypeptide such that it is produced in an active form not requiring additional activation or modification steps.

The ideal host should be readily transformed.

The ideal host should allow a wide range of expression regulatory elements to be used thus ensuring ease of application and versatility.

The ideal host should allow use of easily selectable markers that are cheap to use.

The ideal host should produce stable transformants.

The ideal host should allow cultivation under conditions not detrimental to the expressed protein or polypeptide e.g. low viscosity, low shear.

Fungal systems that have not yet found widespread use are described e.g. in U.S. Pat. No. 5,578,463 by Berka et al suggesting *Neurospora, Podospora, Endothia, Mucor, Cochoibolus* and *Pyricularia* together with *Aspergillus* and *Trichoderma*. However only illustrations of transformation and expression are provided for *Aspergillus* and *Trichoderma* and no details are provided for any of the other suggested hosts.

WO 96/02563 and U.S. Pat. Nos. 5,602,004, 5,604,129 and 5,695,985 to Novo Nordisk describe the drawbacks of *Aspergillus* and *Trichoderma* systems and suggests cultivation conditions for other fingi may be more suited to large scale protein production. The only examples provided for any transformed cultures are those of *Myceliophthora thermophila, Acremonium alabamense, Thielavia terrestris* and *Sporotrichum cellulophilum* strains. The *Sporotrichum* strain is reported to lyse and produce green pigment under fermentation conditions not leading to such results for the other strains. A non-sporulating mutant of *Thielavia terrestris* is described as being the organism of choice by virtue of its morphology. However it is also stated that the protoplasting efficiency of *Thielavia* and *Acremonium* (whereby the *Acremonium* strain used was the imperfect state of the *Thielavia* strain used) is low and that hygromycin was not useful as a selection marker. A large number of others are suggested as being potentially useful by virtue of their morphology but no transformation thereof is described. The suggested strains are *Corynascus, Thermoascus, Chaetomium, Ctenomyces, Scytalidium* and *Talaromyces*. The transformed hosts are mentioned as only producing low levels of the introduced *Humicola* xylanase with *Thielavia* producing the lowest amount; however, the information is ambiguous and could actually infer *Thielavia* was the best embodiment. The nomenclature of this reference is based on the ATCC names of Industrial Fungi of 1994. Thus it is apparent no high degree of heterologous expression was achieved and in fact no positive correlation could be derived between the postulated morphology and the degree of expression. If any correlation could be made, it was more likely to be negative. According to the 1996 ATCC fungal classification *Sporotrichum thermophilum* ATCC 20493 is a *Myceliophthora thermophila* strain. Currently the strain is still identified as *Myceliophthora thermophila*. The unpredicatability of the art is apparent from these recent disclosures.

Also Allison et al (*Curr. Genetics* 21:225-229, 1992) described transformation of *Humicola grisea* var. *thermoidea* using the lithium acetate method and a *Humicola* enzyme-encoding sequence, but no report of expression of heterologous protein from such a strain has been provided.

In 1997 a patent issued to Hawaii Biotechnology Group for transformed *Neurospora* for expression of mammalian peptide such as chymosin. The transformation of auxotrophic

*Neurospora crassa* occurred with spheroplasts. Endogenous transcriptional regulatory regions were introduced and cotransformation was carried out. Nothing is mentioned concerning other hosts and other transformation protocols. Nothing is apparent from the disclosure concerning the degree of expression. It is doubtful whether the degree of expression is high, as immunotechniques (which are useful for detecting small amounts of protein) are the only techniques used to illustrate the presence of the protein. No actual isolation of the protein is disclosed.

WO 97/26330 of Novo Nordisk suggests a method of obtaining mutants of filamentous fungal parent cells having an improved property for production of heterologous polypeptide. The method comprises first finding a specific altered morphology followed by assessing whether a transformant produces more heterologous polypeptide than the parent. The method is illustrated only for strains of *Fusarium* A3/5 and *Aspergillus oryzae*. The method is suggested to be applicable for *Aspergillus, Trichoderma, Thielavia, Fusarium, Neurospora, Acremonium, Tolyplocadium, Humicola, Scytalidium, Myceliophthora* or *Mucor*. As stated above the unpredictability in the art and also the unpredictability of the method of the cited application do not provide a generally applicable teaching with a reasonable expectation of success.

DESCRIPTION OF FIGURES

FIG. 12: Ion exchange chromatography on Macro Prep Q of non-bound fraction after DEAE-Toyopearl of F-60-31 CF sample.

FIG. 13: pH dependencies of activity of enzymes from non-bound fractions of F-60-31 CF sample.

FIG. 16: Temperature dependencies of enzymes from non-bound fraction of F-60-31 sample.

FIG. 17: Ion exchange chromatography on Macro Prep Q of bound fractions 50-53 after DEAE-Toyopearl of F-60-8 sample.

FIG. 19: pH dependencies of activity of 48 kD CBH (pI 4.4) from bound fractions of F-60-8, UF-conc.

FIG. 22: pH courses of activities of 30 kD (pI 8.9) and 90 kD (pI 4.2) proteases toward C1 proteins (50° C., 30 min. incubation).

FIG. 24: Effect of 90 kD (pI 4.2)"neutral" protease on CMCase activity of the proteins in the bound fraction #44-45 (DEAE-Toyopearl) of F 60-8 UV-conc sample at 50° C.

FIG. 26: pH- and temperature dependencies of polygalacturonase activity of F-60-43 UF-conc.

FIG. 27: Inhibition of activity toward MUF-cellobioside by cellobiose for 55 kD CBH (pI 4.4): pH 4.5, 40 C.

FIG. 28: Synergistic effect between 25 kD Endo (pI 4.1) and 55 kD CBH (pI 4.4) toward avicel (40 C/, pH 5, 25 min).

FIG. 32: pH-Dependencies of CMCase and RBB-CMCase activities of 55 kD CBH (pI 4.4).

FIG. 35: Adsorption of the enzymes isolated from bound fractions of F-60-8 UF-conc. sample.

DETAILED DESCRIPTION OF THE INVENTION

Figure 1:
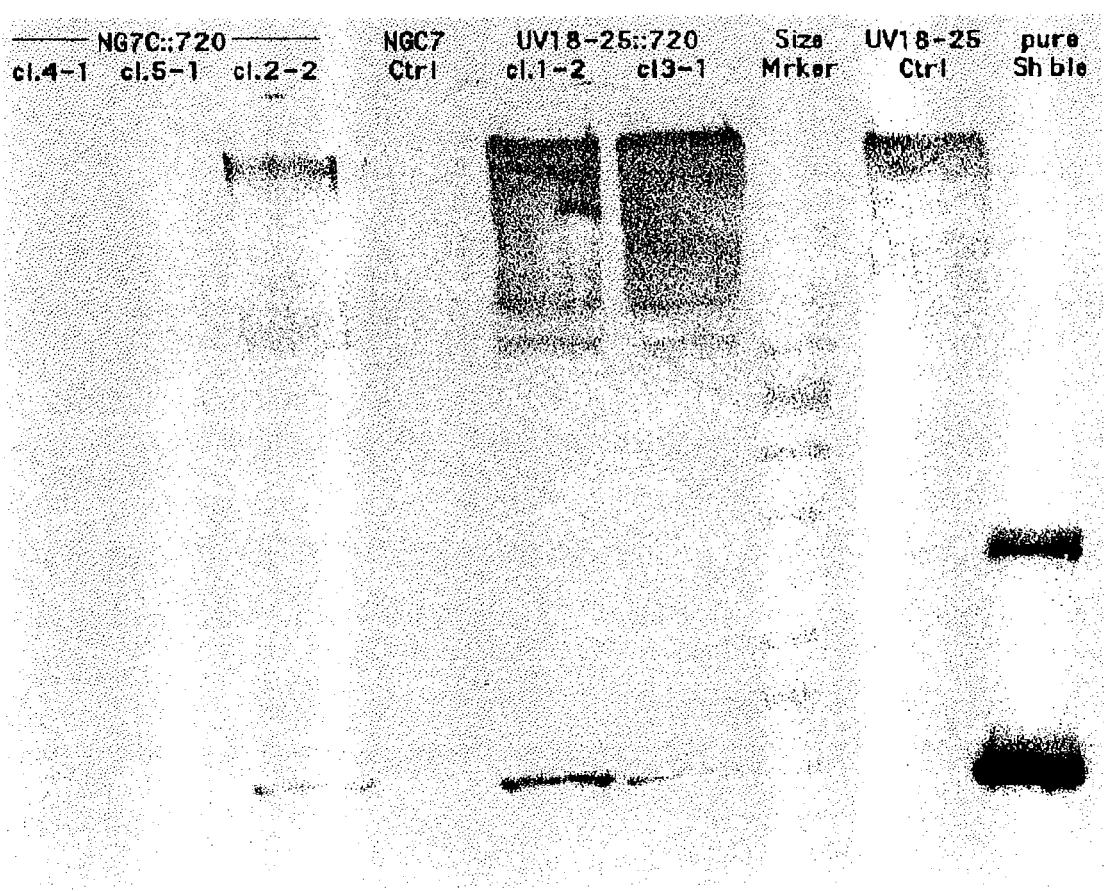
FIG. 1 is a Western blot as described in the Examples

We now describe an alternative fungal expression system with the simplicity of use of the above-mentioned *Aspergilli* and *Trichoderma* fulfilling the above requirements. The new system has not been taught or suggested in the prior art. The new system according to the invention provides the additional advantages that transformation rates are higher than those for the frequently used *Trichoderma reesei* system. In addition the culture conditions offer the additional bonus of being advantageous for the expressed polypeptide.

We further describe a number of industrially interesting enzymes derived from the novel expressing system, together with full sequence information. We also describe novel promoter systems derived from *Chrysosporium* strains and useful for expressing homologous and heterologous genes.

The present invention is thus also concerned with glycosyl hydrolases of the families 7 (e.g. cellobiohydrolases), 10 (e.g. xylanases) and 12 (e.g. endoglucanases), and glyceraldehyde phosphate dehydrogenases, as identified by their amino acid sequence, as well as peptides derived from these enzymatic proteins, and with nucleic acid sequences encoding these peptides and proteins, as well as, in particular, with regulating sequences related to these genes.

In particular, the present invention pertains to isolated or recombinant enzymic proteins or active parts thereof of the four classes referred to above, including mutants thereof having at least a certain degree of sequence identity as specified in the further disclosure and in the claims, as well as nucleic acid sequences encoding these proteins or parts thereof, and/or nucelic acid sequences regulating their expression. These enzymes are especially: (1) a glycosyl hydrolase of family 7 (cellobiohydrolase, CBH1) having at least 75%, preferably at least 80% or even at least 85% amino acid identity with the sequence of SEQ ID No 1; (2) a glycosyl hydrolase of family 10 (endoxylanase XYLF or XYL1) having at least 70%, preferably at least 75% or even at least 80% amino acid identity with the sequence of SEQ ID No 2; (3) a glycosyl hydrolase family of 12 (endoglucanase, EG3) having at least 65%, preferably at least 70% or even at least 80% amino acid identity with the sequence of SEQ ID No. 3; and (4) a glyceraldehyde phosphate dehydrogenase (GPD1) having at least 86%, preferably at least 90% or even at least 93% amino acid identity with the sequence of SEQ ID No 4. Polypeptides and nucleic acid sequences encoding these polypeptides, having at least 20, preferably at least 30 contiguous amino acids of SEQ ID No's 1-4 are also a preferred part of the invention.

The recombinant enzymes may comprise essentially the complete protein, or a truncated protein having at least part of the enzymatic activity. Such truncated part may be the catalytic domain, or at least about 75% of the amino acids thereof. By way of example, the catalytic domain of the CBH1 according to the invention comprises the aminoacids 20-495 of the aminoacid sequence of SEQ ID No. 1, and the catalytic domain of the XYL1 according to the invention comprises the aminoacids 54-384 of the aminoacid sequence of SEQ ID No. 2. The catalytic domain may or may not be combined with a signal sequence originating from another protein and/or with a carbohydrate-binding domain from another enzymic protein. Alternatively, the cellulose-binding domain of the enzymes of the invention (CBH1 and XYL1) may be fused to catalytic domains of other enzymic proteins.

The nucleic acid sequences according to of the invention may be complete protein-encoding regions or oligonucleotides or, preferentially, expression-regulating sequences. Oligonucleotides may be used also as probes for identifying genes corresponding to, but not identical to the genes of SEQ ID No.'s 1-4; these genes, when fulfilling the percentage identity criteria defined herein, as well as encoding and non-encoding parts thereof and their expression products are also part of the invention.

The invention also pertains to expression systems (cassettes) comprising either an expression-regulating region (including a promoter) of any of the four protein classes fused to a gene encoding another protein of interest, or an encoding region of any of these proteins fused to another expression regulating region, or both the expression-regulating region and the protein-encoding region of these novel proteins. The expression-regulating region comprises at least 60%, preferably at least 70%, more preferably at least 75% or even 80% of the 5'-non-coding region of SEQ ID No.'s 1-4, and/or at least 20, especially at least 40 contiguous nucleotides from these 5' non-coding regions. Terminating sequences similarly derived from the 3' non-coding regions of the genes of the invention are also useful in expressing cassettes, whether combined with homologous or heterologous genes.

These expression systems may be contained in a *Chrysosporium* host, such as a *Chrysosporium lucknowense* host, or in another non-fungal or, preferably, fungal host. Examples of other fungal hosts are other *Chrysosporium* species or strains, *Fusarium* species, *Aspergillus* species etc. Such host may be advantageously a host that does not itself, intrinsically or as a result of the culture conditions, produce a protein corresponding to the protein of interest, so as to simplify the recovery of the protein of interest.

Where reference is made in this specification and in the appending claims to "polypeptides" or "peptides" or "polypeptides of interest" or "peptides of interest" as the products of the expression system of the invention, this term also comprise proteins, i.e. polypeptides having a particular function and/or secondary and/or tertiary structure. Where reference is made to percentage amino acid identity, such identity relates to e complete protein or a to a specific part defined by initial and final amino acid number, as determined by the conventionally used BLAST algorithm.

In the production method of the invention, the pH of the culture medium can be neutral or alkaline thus no longer subjecting the produced protein or polypeptide to aggressive and potentially inactivating acid pH. It is also possible to culture at acid pH such as pH 4 for cases where the protein or polypeptide is better suited to an acidic environment. Suitably culture can occur at a pH between 4.0-10.0. A preference however exists for neutral to alkaline pH as the host strain exhibits better growth at such pH, e.g. between 6 and 9. Growth at alkaline pH which can be from pH 8 up and can even be as high as 10 is also a good alternative for some cases. Also the cultivation temperature of such host strains is advantageous to the stability of some types of produced polypeptide. The cultivation temperature is suitably at a temperature of 25-43° C. A temperature in the range from 40° C. down to 23° C. or 30° C. is also advantageously applied. Clearly such conditions are of particular interest for production of mammalian polypeptides. The selected temperature will depend on cost effectiveness of the cultivation and sensitivity of the polypeptide or cultivation strain. The conditions will be determined by the skilled person without undue burden on a case-by-case basis, as is common in the art.

It has also been ascertained that the biomass and viscosity relations to the amount of protein produced is exceedingly favourable for the host according to the invention. Comparisons have been carried out with *Trichoderma longibrachiatum* (formerly also known as *Trichoderma reesei*) and with *Aspergillus niger*. *Trichoderma longibrachiatum* gave 2.5-5 g/l biomass, *Aspergillus niger* gave 5-10 g/l biomass and the host according to the invention gave 0.5-1 g/l biomass under their respective optimised conditions. This thus offers 5-10 fold improvement over the commercially used strains. These commercial strains are strains which themselves are considered in the art to be high producers of proteins and they are successfully used for commercial protein production. They have been cultured under their optimal conditions developed and run viably in large-scale commercial fermenters. The same strains were used to illustrate enormous improvement in viscosity values for cultures of the host according to the invention. At the end of the fermentation process *Trichoderma longibrachiatum* gave a value of 200-600 cP (Centipoise), *Aspergillus niger* gave a value of 1500-2000 cP and the host according to the invention gave a value below 10 cP. This thus provides at least 20-200 fold improvement for viscosity values over the commercially used strains. A quite surprising further aspect was that the protein levels determined for the host cells according to the invention were much higher than for the commercial *Aspergilli* and *Trichoderma reesei* strains, even with the above mentioned surprisingly low biomass and viscosity levels. In summary an easy to use versatile improved transformation system and expression system with improved culturing conditions has hereby been introduced. The strains according to the invention produce surprisingly higher protein levels under these improved conditions and in addition they do such in a shorter fermenter time.

The subject invention is directed at mutant *Chrysosporium* strains comprising a nucleic acid sequence encoding a heterologous protein or polypeptide, said nucleic acid sequence being operably linked to an expression regulating region and optionally a secretion signal encoding sequence and/or a carrier protein encoding sequence. Preferably a recombinant strain according to the invention will secrete the polypeptide of interest. This will avoid the necessity of disrupting the cell in order to isolate the polypeptide of interest and also minimise the risk of degradation of the expressed product by other components of the host cell.

*Chrysosporium* can be defined by morphology consistent with that disclosed in Barnett and Hunter 1972, Illustrated Genera of Imperfect Fungi, 3rd Edition of Burgess Publishing Company. Other sources providing details concerning classification of fungi of the genus *Chrysosporium* are known e.g. Sutton Classification (Van Oorschot, C. A. N. (1980) "A revision of *Chrysosporium* and allied genera" in Studies in Mycology No. 20 of the CBS in Baarn The Netherlands p1-36). CBS is one of the depository institutes of the Budapest Treaty. According to these teachings the genus *Chrysosporium* falls within the family Moniliaceae which belongs to the order Hyphomycetales. The criteria that can be used are the following:

1. Signs of Hyphomycetales Order:

Conidia are produced directly on mycelium, on separate sporogenous cells or on distinct conidiophores.

2. Signs of Moniliaceae Family:

Both conidia and conidiophores (if present) are hyaline or brightly coloured; conidiophores are single or in loose clusters.

3. Signs of *Chrysosporium* Corda 1833 Genus:

Colonies are usually spreading, white, sometimes cream-coloured, pale brown or yellow, felty and/or powdery. Hyphae are mostly hyaline and smooth-walled, with irregular, more or less orthotopic branching. Fertile hyphae exhibit little or no differentiation. Conidia are terminal and lateral, thallic, borne all over the hyphae, sessile or on short protrusions or side branches, subhyaline or pale yellow, thin- or thick-walled, subglobose, clavate, pyriform, orobovoid, 1-celled, rarely 2-celled, truncate. Intercalary conidia are sometimes present, are solitary, occasionally catenate, subhyaline or pale yellow, broader than the supporting hyphae, normally 1-celled, truncate at both ends. Chlamydospores are occasionally present.

Another source providing information on fungal nomenclature is ATCC (US). Their website is may be accessed on the World Wide Web (HTTP protocol) at atcc.org. CBS also has a website located on the World Wide Web (HTTP protocol) at cbs.knaw.n1 providing relevant information. VKM in Moscow is also a reliable source of such information, located on the World Wide Web (HTTP protocol) at bdt.org.br.bdt.msdn.vkm/general. Another source is the United States Department of Agriculture Research Service website (located on an NT webserver rather than the World Wide Web) at ars-grin.gov/fungaldatabases. All these institutions can provide teaching on the distinguishing characteristics of a *Chrysosporium*.

Strains defined as being of *Myceliophthora thermophila* are not considered to define *Chrysosporium* strains according to the definition of the invention. In the past there has been considerable confusion over the nomenclature of some *Myceliophthora* strains. Preferably the *Chrysosporium* according to the invention are those which are clearly distinguishable as such and cannot be confused with *Myceliophthora, Sporotrichum* or *Phanerochaete chrysosporium.*

The following strains are defined as *Chrysosporium* but the definition of *Chrysosporium* is not limited to these strains: *C. botryoides, C. carmichaelii, C. crassitunicatum, C. europae, C. evolceannui, C. farinicola, C. fastidium, C. filiforme, C. georgiae, C. globiferum, C. globiferum* var. *articulatum, C. globiferum* var. *niveum, C. hirundo, C. hispanicum, C. holmii, C. indicum, C. inops, C. keratinophilum, C. kreiselii, C. kuzurovianum, C. lignorum, C. lobatum, C. lucknowense, C. lucknowense* Garg 27K, *C. medium, C. medium* var. *spissescens, C. mephiticum, C. merdarium, C. merdarium* var. *roseum, C. minor, C. pannicola, C. parvum, C. parvum* var. *crescens, C. pilosum, C. pseudomerdarium, C. pyriformis, C. queenslandicum, C. sigleri, C. sulfureum, C. synchronum, C. tropicum, C. undulatum, C. vallenarense, C. vespertilium, C. zonatum.*

*C. lucknowense* forms one of the species of *Chrysosporium* that have raised particular interest as it has provided a natural high producer of cellulase proteins (WO 98/15633 and related U.S. Pat. No. 5,811,381, as well as U.S. Pat. No. 6,015,707). The characteristics of this *Chrysosporium lucknowense* are:

Colonies attain 55 mm diameter on Sabouraud glucose agar in 14 days, are cream-coloured, felty and fluffy; dense and 3-5 mm high; margins are defined, regular, and fimbriate; reverse pale yellow to cream-coloured. Hyphae are hyaline, smooth- and thin-walled, little branched. Aerial hyphae are mostly fertile and closely septate, about 1-3.5 μm wide. Submerged hyphae are infertile, about 1-4.5 μm wide, with the thinner hyphae often being contorted. Conidia are terminal and lateral, mostly sessile or on short, frequently conical protrusions or short side branches. Conidia are solitary but in close proximity to one another, 1-4 conidia developing on one hyphal cell, subhyaline, fairly thin- and smooth-walled, mostly subglobose, also clavate orobovoid, 1-celled, 2.5–11×1.5-6 μm, with broad basal scars (1-2 μm). Intercalary conidia are absent. Chlamydospores are absent. ATCC 44006, CBS 251.72, CBS 143.77 and CBS 272.77 are examples of *Chrysosporium lucknowense* strains and other examples are provided in WO 98/15633 and U.S. Pat. No. 5,811,381.

A further strain was isolated from this species with an even higher production capacity for cellulases. This strain is called C1 by its internal notation and was deposited with the International Depository of the All Russian Collection of microorganisms of the Russian Academy of Sciences Bakrushina Street 8, Moscow, Russia 113184 on Aug. 29, 1996, as a deposit according to the Budapest Treaty and was assigned Accession Number VKM F-3500D. It is called *Chrysosporium lucknowense* Garg 27K. The characteristics of the C1 strain are as follows:

Colonies grow to about 55-66 mm diameter in size on potato-dextrose agar in about 7 days; are white-cream-coloured, felty, 2-3 μm high at the center; margins are defined, regular, fimbriate; reverse pale, cream-coloured. Hyphae are hyaline, smooth- and thin-walled, little branched. Aerial hyphae are fertile, septate, 2-3 mm wide. Submerged hyphae are infertile. Conidia are terminal and lateral; sessile or on short side branches; absent; solitary, but in close proximity to one another, hyaline, thin- and smooth-walled, subglobose, clavate or obovoid, 1-celled, 4-10 μm. Chlamydospores are absent. Intercalary conidia are absent.

The method of isolation of the C1 strain is described in WO 98/15633 and U.S. Pat. No. 5,811,381. Strains exhibiting such morphology are included within the definition of *Chry-* sosporium according to the invention. Also included within the definition of *Chrysosporium* are strains derived from *Chrysosporium* predecessors including those that have mutated somewhat either naturally or by induced mutagenesis. In particular the invention covers mutants of *Chrysosporium* obtained by induced mutagenis, especially by a combination of irradiation and chemical mutagenesis.

For example strain C1 was mutagenised by subjecting it to ultraviolet light to generate strain UV13-6. This strain was subsequently further mutated with N-methyl-N'-nitro-N-nitrosoguanidine to generate strain NG7C-19. The latter strain in turn was subjected to mutation by ultraviolet light resulting in strain UV18-25. During this mutation process the morphological characteristics have varied somewhat in culture in liquid or on plates as well as under the microscope. With each successive mutagenesis the cultures showed less of the fluffy and felty appearance on plates that are described as being characteristic of *Chrysosporium*, until the colonies attained a flat and matted appearance. A brown pigment observed with the wild type strain in some media was also less prevalent in mutant strains. In liquid culture the mutant UV18-25 was noticeably less viscous than the wild type strain C1 and the mutants UV13-6 and NG7C-19. While all strains maintained the gross microscopic characteristics of *Chrysosporium*, the mycelia became narrower with each successive mutation and with UV18-25 distinct fragmentation of the mycelia could be observed. This mycelial fragmentation is likely to be the cause of the lower viscosity associated with cultures of UV 18-25. The ability of the strains to sporulate decreased with each mutagenic step. The above illustrates that for a strain to belong to the genus *Chrysosporium* there is some leeway from the above morphological definition. At each mutation step production of cellulase and extracellular proteins has in addition also increased, while several mutations resulted in decrease of protease expression. Criteria with which fungal taxonomy can be determined are available from CBS, VKMF and ATCC for example.

In particular the anamorph form of *Chrysosporium* has been found to be suited for the production application according to the invention. The metabolism of the anamorph renders it extremely suitable for a high degree of expression. A teleomorph should also be suitable as the genetic make-up of the anamorphs and teleomorphs is identical. The difference between anamorph and teleomorph is that one is the asexual state and the other is the sexual state. The two states exhibit different morphology under certain conditions.

It is preferable to use non-toxic *Chrysosporium* strains of which a number are known in the art as this will reduce risks to the environment upon large scale production and simplify production procedures with the concomitant reduction in costs.

An expression-regulating region is a DNA sequence recognised by the host *Chrysosporium* strain for expression. It comprises a promoter sequence operably linked to a nucleic acid sequence encoding the polypeptide to be expressed. The promoter is linked such that the positioning vis-à-vis the initiation codon of the sequence to be expressed allows expression. The promoter sequence can be constitutive or inducible. Any expression regulating sequence or combination thereof capable of permitting expression of a polypeptide from a *Chrysosporium* strain is envisaged. The expression regulating sequence is suitably a fungal expression-regulating region e.g. an ascomycete regulating region. Suitably the fugal expression regulating region is a regulating region from any of the following genera of fungi: *Aspergillus, Trichoderma, Chrysosporium* (preferred), *Hansenula, Mucor, Pichia, Neurospora, Tolypocladium, Rhizomucor, Fusarium, Penicillium, Saccharomyces, Talaromyces* or alternative sexual forms thereof like *Emericella, Hypocrea* e.g. the cellobiohydrolase promoter from *Trichoderma*, glucoamylase promoter from *Aspergillus*, glyceraldehyde phosphate dehydrogenase promoter from *Aspergillus*, alcohol dehydrogenase A and alcohol dehydrogenase R promoter of *Aspergillus*, TAKA amylase promoter from *Aspergillus*, phosphoglycerate and cross-pathway control promoters of *Neurospora*, aspartic proteinase promoter of *Rhizomucor miehei*, lipase promoter of *Rhizomucor miehei* and beta-galactosidase promoter of *Penicillium canescens*. An expression regulating sequence from the same genus as the host strain is extremely suitable, as it is most likely to be specifically adapted to the specific host. Thus preferably the expression regulating sequence is one from a *Chrysosporium* strain.

We have found particular strains of *Chrysosporium* to express proteins in extremely large amounts and natural expression regulating sequences from these strains are of particular interest. These strains are internally designated as *Chrysosporium* strain C1, strain UV13-6, strain NG7C-19 and strain UV18-25. They have been deposited in accordance with the Budapest Treaty with the All Russian Collection (VKM) depository institute in Moscow. Wild type C1 strain was deposited in accordance with the Budapest Treaty with the number VKM F-3500 D, deposit date 29 Aug. 1996, C1 UV13-6 mutant was deposited with number VKM F-3632 D, and deposit date 2 Sep. 1998, C1 NG7C-19 mutant was deposited with number VKM F-3633 D and deposit date 2 Sep. 1998 and C1 UV18-25 mutant was deposited with number VKM F-3631 D and deposit date 2 Sep. 1998.

Preferably an expression-regulating region enabling high expression in the selected host is applied. This can also be a high expression-regulating region derived from a heterologous host, such as are well known in the art. Specific examples of proteins known to be expressed in large quantities and thus providing suitable expression regulating sequences for the invention are without being limited thereto hydrophobin, protease, amylase, xylanase, pectinase, esterase, beta-galactosidase, cellulase (e.g. endo-glucanase, cellobiohydrolase) and polygalacturonase. The high production has been ascertained in both solid state and submerged fermentation conditions. Assays for assessing the presence or production of such proteins are well known in the art. The catalogues of Sigma and Megazyme for example provide numerous examples. Megazyme is located at Bray Business Park, Bray, County Wicklow in Ireland. Sigma Aldrich has many affiliates world wide e.g. USA P.O. Box 14508 St. Louis Mo. For cellulase we refer to commercially available assays such as CMCase assays, endoviscometric assays, Avicelase assays, beta-glucanase assays, RBBCMCase assays, Cellazyme C assays. Xylanase assays are also commercially available (e.g. DNS and Megazyme). Alternatives are well known to a person skilled in the art and can be found from general literature concerning the subject and such information is considered incorporated herein by reference. By way of example we refer to "Methods in Enzymology Volume 1, 1955 right through to volumes 297-299 of 1998. Suitably a *Chrysosporium* promoter sequence is applied to ensure good recognition thereof by the host.

We have found that heterologous expression-regulating sequences work as efficiently in *Chrysosporium* as native *Chrysosporium* sequences. This allows well known constructs and vectors to be used in transformation of *Chrysosporium* as well as offering numerous other possibilities for constructing vectors enabling good rates of expression in this novel expression and secretion host. For example standard *Aspergillus* transformation techniques can be used as described for example by Christiansen et al in Bio/Technol. 6:1419-1422 (1988). Other documents providing details of *Aspergillus* transformation vectors, e.g. U.S. Pat. Nos. 4,816,405, 5,198,345, 5,503,991, 5,364,770 and 5,578,463, EP-B-215.594 (also for *Trichoderma*) and their contents are incorporated by reference. As extremely high expression rates for cellulase have been ascertained for *Chrysosporium* strains, the expression regulating regions of such proteins are particularly preferred. We refer for specific examples to the previously mentioned deposited *Chrysosporium* strains.

A nucleic acid construct comprising a nucleic acid expression regulatory region from *Chrysosporium*, preferably from *Chrysosporium lucknowense* or a derivative thereof forms a separate embodiment of the invention as does the mutant *Chrysosporium* strain comprising such operably linked to a gene encoding a polypeptide to be expressed. Suitably such a nucleic acid construct will be an expression regulatory region from *Chrysosporium* associated with cellulase or xylanase expression, preferably cellobiohydrolase expression, more specifically expression of a 55 kDa cellobiohydrolase. The *Chrysosporium* promoter sequences of an endoglucanase of 25 kDa (C1-EG5) and of an endoglucanase of 43 kDa (C1-EG6), wherein the molecular weights are determined according to SDS PAGE (with the molecular weights according to amino acid sequence data being 21.9 kDa and 39.5 kDa), are provided by way of example. Thus, the *Chrysosporium* promoter sequences of hydrophobin, protease, amylase, xylanase, esterase, pectinase, beta-galactosidase, cellulase (e.g. endoglucanase, cellobiohydrolase) and polygalacturonase are considered to also fall within the scope of the invention. Any of the promoters or regulatory regions of expression of enzymes disclosed in Table A or B can be suitably employed. The nucleic acid sequence according to the invention can suitably be obtained from a *Chrysosporium* strain according to the invention, such strain being defined elsewhere in the description. The manner in which promoter sequences can be determined are numerous and well known in the art. Nuclease deletion experiments of the region upstream of the ATG codon at the beginning of the relevant gene will provide such sequence. Also for example analysis of consensus sequences can lead to finding a gene of interest. Using hybridisation and amplification techniques one skilled in the art can readily arrive at the corresponding promoter sequences.

The promoter sequences of C1 endoglucanases were identified in this manner, by cloning the corresponding genes, and are given in SEQ ID No.'s 5 (EG5) and 6 (EG6), respectively. Other preferred promoters according to the invention are the 55 kDa cellobiohydrolase (CBH1) promoter and the 30 kDa xylanase (XylF) promoters, as the enzymes are expressed at high level by their own promoters. The corresponding promoter sequences can be identified in a straightforward manner by cloning as described below for the endoglucanase promoters, using the sequence information given in SEQ ID No. 1 (for CBH1) and SEQ ID No. 2 (for XylF), respectively. The promoters of the carbohydrate-degrading enzymes of *Chrysosporium*, especially C1 promoters, can advantageously be used for expressing desired polypeptides in a host organism, especially a fungal or other microbial host organism. Promoter sequences having at least 60%, preferably at least 70%, most preferably at least 80% nucleotide sequence identity with the sequence given in SEQ ID No's 1 and 2, or with the sequences found for other *Chrysosporium* genes, are part of the present invention.

For particular embodiments of the recombinant strain and the nucleic acid sequence according to the invention we also refer to the examples. We also refer for the recombinant strains to prior art describing high expression promoter sequences in particular those providing high expression in fungi e.g. such as are disclosed for *Aspergillus* and *Trichoderma*. The prior art provides a number of expression regulating regions for use in *Aspergillus* e.g. U.S. Pat. No. 5,252, 726 of Novo and U.S. Pat. No. 5,705,358 of Unilever. The contents of such prior art are hereby incorporated by reference.

The hydrophobin gene is a fungal gene that is highly expressed. It is thus suggested that the promoter sequence of a hydrophobin gene, preferably from *Chrysosporium*, may be suitably applied as expression regulating sequence in a suitable embodiment of the invention. *Trichoderma reesei* and *Trichoderma harzianum* gene sequences for hydrophobin have been disclosed for example in the prior art as well as a gene sequence for *Aspergillus fumigatus* and *Aspergillus nidulans* and the relevant sequence information is hereby incorporated by reference (Munoz et al, *Curr. Genet.* 1997, 32(3):225-230; Nakari-Setala T. et al, *Eur. J. Biochem.* 1996 15:235 (1-2):248-255, M. Parta et al, *Infect. Immun.* 1994 62 (10): 4389-4395 and Stringer M. A. et al. *Mol. Microbiol.* 1995 16(1):33-44). Using this sequence information a person skilled in the art can obtain the expression regulating sequences of *Chrysosporium* hydrophobin genes without undue experimentation following standard techniques as suggested already above. A recombinant *Chrysosporium* strain according to the invention can comprise a hydrophobin-regulating region operably linked to the sequence encoding the polypeptide of interest.

An expression regulating sequence can also additionally comprise an enhancer or silencer. These are also well known in the prior art and are usually located some distance away from the promoter. The expression regulating sequences can also comprise promoters with activator binding sites and repressor binding sites. In some cases such sites may also be modified to eliminate this type of regulation. Filamentous fungal promoters in which creA sites are present have been described. Such creA sites can be mutated to ensure the glucose repression normally resulting from the presence of the non-mutated sites is eliminated. Gist-Brocades' WO 94/13820 illustrates this principle. Use of such a promoter enables production of the polypeptide encoded by the nucleic acid sequence regulated by the promoter in the presence of glucose. The same principle is also apparent from WO 97/09438. These promoters can be used either with or without their creA sites. Mutants in which the creA sites have been mutated can be used as expression regulating sequences in a recombinant strain according to the invention and the nucleic acid sequence it regulates can then be expressed in the presence of glucose. Such *Chrysosporium* promoters ensure derepression in an analogous manner to that illustrated in WO 97/09438. The identity of creA sites is known from the prior art. Alternatively, it is possible to apply a promoter with CreA binding sites that have not been mutated in a host strain with a mutation elsewhere in the repression system e.g. in the creA gene itself, so that the strain can, notwithstanding the presence of creA binding sites, produce the protein or polypeptide in the presence of glucose.

Terminator sequences are also expression-regulating sequences and these are operably linked to the 3' terminus of the sequence to be expressed. Any fungal terminator is likely to be functional in the host *Chrysosporium* strain according to the invention. Examples are *A. nidulans* trpC terminator (1), *A. niger* alpha-glucosidase terminator (2), *A. niger* glucoamylase terminator (3), *Mucor miehei* carboxyl protease terminator (U.S. Pat. No. 5,578,463) and the *Trichoderma reesei* cellobiohydrolase terminator. Naturally *Chrysosporium* terminator sequences will function in *Chrysosporium* and are suitable e.g. CBH1 or EG6 terminator.

A suitable recombinant *Chrysosporium* strain according to the invention has the nucleic acid sequence to be expressed operably linked to a sequence encoding the amino acid sequence defined as signal sequence. A signal sequence is an amino acid sequence which when operably linked to the amino acid sequence of the expressed polypeptide allows secretion thereof from the host fungus. Such a signal sequence may be one normally associated with the heterologous polypeptide or may be one native to the host. It can also be foreign to both host and the polypeptide. The nucleic acid sequence encoding the signal sequence must be positioned in frame to permit translation of the signal sequence and the heterologous polypeptide. Any signal sequence capable of permitting secretion of a polypeptide from a *Chrysosporium* strain is envisaged. Such a signal sequence is suitably a fungal signal sequence, preferably an ascomycete signal sequence.

Suitable examples of signal sequences can be derived from yeasts in general or any of the following specific genera of fungi: *Aspergillus, Trichoderma, Chrysosporium, Pichia, Neurospora, Rhizomucor, Hansenula, Humicola, Mucor, Tolypocladium, Fusarium, Penicillium, Saccharomyces, Talaromyces* or alternative sexual forms thereof like *Emericella, Hypocrea*. Signal sequences that are particularly useful are often natively associated with the following proteins a cellobiohydrolase, an endoglucanase, a beta-galactosidase, a xylanase, a pectinase, an esterase, a hydrophobin, a protease or an amylase. Examples include amylase or glucoamylase of *Aspergillus* or *Humicola* (4), TAKA amylase of *Aspergillus oryzae*, alpha-amylase of *Aspergillus niger*, carboxyl peptidase of *Mucor* (U.S. Pat. No. 5,578,463), a lipase or proteinase from *Rhizomucor miehei*, cellobiohydrolase of *Trichoderma* (5), beta-galactosidase of *Penicillium canescens* and alpha mating factor of *Saccharomyces.*

Alternatively the signal sequence can be from an amylase or subtilisin gene of a strain of *Bacillus*. A signal sequence from the same genus as the host strain is extremely suitable as it is most likely to be specifically adapted to the specific host thus preferably the signal sequence is a signal sequence of *Chrysosporium*. We have found particular strains of *Chrysosporium* to excrete proteins in extremely large amounts and naturally signal sequences from these strains are of particular interest. These strains are internally designated as *Chrysosporium* strain C1, strain UV13-6, strain NG7C-19 and strain UV18-25. They have been deposited in accordance with the Budapest Treaty as described elsewhere in this description. Signal sequences from filamentous fingi, yeast and bacteria are useful. Signal sequences of non-fungal origin are also considered useful, particularly bacterial, plant and mammalian.

A recombinant *Chrysosporium* strain according to any of the embodiments of the invention can further comprise a selectable marker. Such a selectable marker will permit easy selection of transformed or transfected cells. A selectable marker often encodes a gene product providing a specific type of resistance foreign to the non-transformed strain. This can be resistance to heavy metals, antibiotics and biocides in general. Prototrophy is also a useful selectable marker of the non-antibiotic variety. Non-antibiotic selectable markers can be preferred where the protein or polypeptide of interest is to be used in food or pharmaceuticals with a view to speedier or less complicated regulatory approval of such a product. Very often the GRAS indication is used for such markers. A number of such markers are available to the person skilled in the art. The FDA e.g. provides a list of such. Most commonly used are selectable markers selected from the group conferring resistance to a drug or relieving a nutritional defect e.g the group comprising amdS (acetamidase), hph (hygromycin phosphotransferase), pyrg (orotidine-5'-phosphate decarboxylase), trpc (anthranilate synthase), argB (ornithine carbamoyltransferase), sC (sulphate adenyltransferase), bar (phosphinothricin acetyltransferase), glufosinate resistance, niaD (nitrate reductase), a bleomycin resistance gene, more specifically Sh ble, sulfonylurea resistance e.g. acetolactate synthase mutation ilv1. Selection can also be carried out by virtue of cotransformation where the selection marker is on a separate vector or where the selection marker is on the same nucleic acid fragment as the polypeptide-encoding sequence for the polypeptide of interest.

As used herein the term heterologous polypeptide is a protein or polypeptide not normally expressed and secreted by the *Chrysosporium* host strain used for expression according to the invention. The polypeptide can be of plant or animal (vertebrate or invertebrate) origin e.g. mammalian, fish, insect, or micro-organism origin, with the proviso it does not occur in the host strain. A mammal can include a human. A micro-organism comprises viruses, bacteria, archaebacteria and fungi i.e. filamentous fungi and yeasts. Bergey's Manual for Bacterial Determinology provides adequate lists of bacteria and archaebacteria. For pharmaceutical purposes quite often a preference will exist for human proteins thus a recombinant host according to the invention forming a preferred embodiment will be a host wherein the polypeptide is of human origin. For purposes such as food production suitably the heterologous polypeptide will be of animal, plant or algal origin. Such embodiments are therefore also considered suitable examples of the invention. Alternative embodiments that are useful also include a heterologous polypeptide of any of bacterial, yeast, viral, archaebacterial and fungal origin. Fungal origin is most preferred.

A suitable embodiment of the invention will comprise a heterologous nucleic acid sequence with adapted codon usage. Such a sequence encodes the native amino acid sequence of the host from which it is derived, but has a different nucleic acid sequence, i.e. a nucleic acid sequence in which certain codons have been replaced by other codons encoding the same amino acid but which are more readily used by the host strain being used for expression. This can lead to better expression of the heterologous nucleic acid sequence. This is common practice to a person skilled in the art. This adapted codon usage can be carried out on the basis of known codon usage of fungal vis-à-vis non-fungal codon usage. It can also be even more specifically adapted to codon usage of *Chrysosporium* itself. The similarities are such that codon usage as observed in *Trichoderma, Humicola* and *Aspergillus* should enable exchange of sequences of such organisms without adaptation of codon usage. Details are available to the skilled person concerning the codon usage of these fungi and are incorporated herein by reference.

The invention is not restricted to the above mentioned recombinant *Chrysosporium* strains, but also covers a recombinant *Chrysosporium* strain comprising a nucleic acid sequence encoding a homologous protein for a *Chrysosporium* strain, said nucleic acid sequence being operably linked to an expression-regulating region and said recombinant strain expressing more of said protein than the corresponding non-recombinant strain under the same conditions. In the case of homologous polypeptide of interest such is preferably a neutral or alkaline enzyme like a hydrolase, a protease or a carbohydrate degrading enzyme as already described elsewhere. The polypeptide may also be acidic. Preferably the recombinant strain will express the polypeptide in greater amounts than the non-recombinant strain. All comments mentioned vis-à-vis the heterologous polypeptide are also valid (mutatis mutandis) for the homologous polypeptide cellulase.

Thus the invention also covers genetically engineered *Chrysosporium* strains wherein the sequence that is introduced can be of *Chrysosporium* origin. Such a strain can, however, be distinguished from natively occurring strains by virtue of for example heterologous sequences being present in the nucleic acid sequence used to transform or transfect the *Chrysosporium*, by virtue of the fact that multiple copies of the sequence encoding the polypeptide of interest are present or by virtue of the fact that these are expressed in an amount exceeding that of the non-engineered strain under identical conditions or by virtue of the fact that expression occurs under normally non-expressing conditions. The latter can be the case if an inducible promoter regulates the sequence of interest contrary to the non-recombinant situation or if another factor induces the expression than is the case in the non-engineered strain. The invention as defined in the preceding embodiments is not intended to cover naturally occurring *Chrysosporium* strains. The invention is directed at strains derived through engineering either using classical genetic technologies or genetic engineering methodologies.

All the recombinant strains of the invention can comprise a nucleic acid sequence encoding a heterologous protein selected from carbohydrate-degrading enzymes (cellulases, xylanases, mannanases, mannosidases, pectinases, amylases, e.g. glucoamylases, -amylases, alpha- and beta-galactosidases, -and -glucosidases, -glucanases, chitinases, chitanases), proteases (endoproteases, amino-proteases, amino- and carboxy-peptidases, keratinases), other hydrolases (lipases, esterases, phytases), oxidoreductases (catalases, glucose-oxidases) and transferases (transglycosylases, transglutaminases, isomerases and invertases).

TABLE A pH range where enzymes retain activity and/or stability

| Sample | pH range retaining > 50% enzymatic activity | | | pH range retaining > 70% enzymatic activity | | | Stability (20 h, 50° C.) |
| --- | --- | --- | --- | --- | --- | --- | --- |
| | CMCase | RBB-CMCase | Other substrates | CMCase | RBB-CMCase | Other substrates | % from max pH 7.5/8 |
| 30 Kd protease (alkaline) 30 kD | — | — | 12.5 | — | — | 12.0 | — |
| Xyl (alkaline) | — | — | 10.0 | — | — | 8.5 | 80 |
| 51 kD Xyl | — | — | 8.0 | — | — | 7.5 | — |
| 60 kD Xyl | — | — | 9.5 | — | — | 9.0 | 85 |
| 45 kD endo | 7.0 | 8.0 | — | 6.5 | 7.0 | — | 75 |
| 55 kD endo | 8.0 | 8.0 | — | 7.0 | 7.0 | — | 55 |
| 25 kD (21.8 kD*) endo | 7.5 | 10.0 | — | 6.5 | 9.0 | — | 80 |
| 43 kD (39.6 kD*) endo | 8.0 | 8.0 | — | 7.2 | 7.2 | — | — |
| 45 kD, β-Gal/β-Gluc | — | — | 6.8 | — | — | 5.7 | — |
| 48 kD CBH with β-Gluc traces | 5.2 | 7.5 | 8.0 | 5.0 | 6.8 | — | — |
| 55 kD CBH | 8.0 | 9.0 | — | 7.4 | 8.5 | — | 70 |
| 65 kD PGU | — | — | 8.0 | — | — | 7.3 | — |
| 90 kD protease | — | — | 9.0 | — | — | 9.0 | — |
| 100 kD esterase | — | — | 9.0 | — | — | 9.0 | — |

*molecular weights (by MALDI)
Note:
*all other molecular weights by SDS PAGE
*enzymes were taken in equal protein contents
*xyl = xylanase
*endo = endoglucanase
*gal = galactosidase
*gluc = glucosidase
*CBN = cellbiohydrolase
*PGU = polygalacturonase

TABLE B

Activities of enzymes isolated from ultrafiltrate from 18-25 strain toward different substrates (pH 5), units/mg protein

| Sample | pI | CMC 50° C. | RBB-CMC 40° C. | CMC-41 40° C. | FP 50° C. | CMC (visc) 40° C. | b-Glucan 50° C. | pNP-a-G 40° C. | pNP-b-G 40° C. | Cellobiose 40° C. | Avicel 40° C. | MUF-cellobioside 40° C. |
| --- | --- | --- | --- | --- | --- | --- | --- | --- | --- | --- | --- | --- |
| 30 kD protease | 8.9 | 0 | 0 | 0 | 0 | 0 | 0 | — | 0 | 0 | 0 | 0 |
| 30 kD Xyl | 9.1 | 0.1 | 2 | 0.1 | 0.16 | 0.1 | 0 | — | 0 | — | 0 | 0 |
| 51 kD Xyl | 8.7 | 0.1 | 4.2 | — | 0.19 | — | 0 | — | 0 | — | 0 | 0 |
| 60 kD Xyl | 4.7 | 0 | — | — | 0 | — | 0 | — | 0 | — | 0 | 0.14 |
| 45 kD endo | 6 | 51 | 86 | 7.6 | 0.2 | 47 | 36 | — | 0 | — | 0.5 | 0 |
| 55 kD endo | 4.9 | 47 | 94 | 7.7 | 0.3 | 39 | 25 | — | 0 | — | 0.5 | 0 |
| 25 kD (21.8 kD*) endo | 4.1 | 19 | 15 | 3.9 | 0.3 | 11 | 3.8 | — | 0 | 0 | 0.05 | 0 |
| 43 kD (39.6 kD*) endo | 4.2 | 0.43 | 0.2 | 0.1 | 0 | 0.2 | 0.2 | — | 0 | 0 | 0 | 0 |

TABLE B-continued

Activities of enzymes isolated from ultrafiltrate from 18-25 strain toward different substrates (pH 5), units/mg protein

| | | | | | | | | | | | | |
|---|---|---|---|---|---|---|---|---|---|---|---|---|
| 45 kD a,b-Gal/b-Gluc | 4.2 | 0 | 0 | 0 | 0 | 0.01 | 0.01 | 0 | 0.4 | 0.06 | 0 | 0 |
| traces + glucono-d-lactone | 4.4 | 0.67 | 1.3 | 1.2 | 0.4 | 0.8 | 0.77 | 0 | 1.70 | 0.08 | 0 | 0.2 |
| 55 kD CBH with b-Gluc traces + glucono-d-lactone | 4.4 | 0.7 | 0.16 | 0.27 | 0.4 | 0.1 | 0.1 | — | 0.050 | 0.08 | 0.46 | 0.2 0.14 |
| 65 kD PGU | 4.4 | 0 | 0 | 0 | 0 | 0 | 0 | — | 0 | 0 | 0 | 0 |
| 90 kD protease | 4.2 | — | — | — | — | — | — | — | — | — | — | — |
| 100 kD esterase | 4.5 | 0 | 0 | 0 | 0 | 0 | 0 | — | 0 | 0 | 0 | 0 |

| Sample | MUF-lactoside 40° C. | MUF-xyloside 40° C. | Lactose 40° C. | Xylan 50° C. | Polygalacturonic acid 50° C. | MUF-glucoside 40° C. | Galactomannan 50° C. | pNP-a-galactoside 40° C. | pNP-b-galactoside 40° C. | Dyed casein** 50° C. | pNP butyrate 60° C. |
|---|---|---|---|---|---|---|---|---|---|---|---|
| 30 kD protease | 0 | 0 | 0 | 0 | 0 | 0 | 0 | 0 | 0 | 0.4 | 0 |
| 30 kD Xyl | 0 | 0 | — | 25 | 0 | 0 | 0 | 0 | — | 0 | 0 |
| 51 kD Xyl | 0 | 0 | — | 19 | 0 | 0 | 0 | 0 | — | 0 | 0 |
| 60 kD Xyl | 0.02 | 0.04 | — | 16.3 | 0 | 0 | 0 | 0 | 0 | 0 | 0 |
| 45 kD endo | 0 | 0 | — | 1 | — | 0 | 1.8 | 0 | — | 0 | 0 |
| 55 kD endo | 0 | 0 | — | 0 | — | 0 | 0.4 | 0 | — | 0 | 0 |
| 25 kD (21.8 kD*) endo | 0 | — | 0 | 0.03 | 0 | — | 0 | 0 | 0 | 0 | 0 |
| 43 kD (39.6 kD*) endo | 0 | — | 0 | 0 | 0 | — | 0 | 0 | 0 | 0 | 0 |
| 45 kD a,b-Gal/b-Gluc | 0 | — | 0.01 | 0 | 0.1 | 0.1 | 0.2 | 0.2 | 0.3 | 0 | 1.7 |
| traces + glucono-d-lactone | 0.36 0.36 | — | 0 | 0 | 0.1 | 0.4 | 0 | 0 | 0 | 0 | 2.3 |
| 55 kD CBH with b-Gluc traces + glucono-d-lactone | 0.7 0.6 | — | 0 | 0.1 | 0 | — | 0 | 0 | 0 | 0 | 0 |
| 65 kD PGU | 0 | — | 0 | 0 | 1 | — | 0 | 0 | 0 | 0 | 0 |
| 90 kD protease | — | — | — | — | — | — | — | — | — | 0.01 | — |
| 100 kD esterase | 0 | — | 0 | 0 | 0 | 0 | 0 | 0 | 0 | 0 | 0.8 |

*molecular weights (by MALDI)
**activity toward dyed casein was expressed in arbitrary units/mg The most interesting products to be produced according to invention are cellulases, xylanases, pectinases, lipases and proteases, wherein cellulases and xylanases cleave beta-1,4-bonds, and cellulases comprise endoglucanases, cellobiohydrolases and beta-glucosidases. These proteins are extremely useful in various industrial processes known in the art. Specifically for cellulases we refer e.g. to WO 98/15633 describing cellobiohydrolases and endoglucanases of use. The contents of said application are hereby incorporated by reference. We also refer to Tables A and B providing further details of interesting *Chrysosporium* proteins.

It was found according to the invention, that *Chrysosporium* mutants can be made that have reduced expression of protease, thus making them even more suitable for the production of proteinaceous products, especially if the proteinaceous product is sensitive to protease activity. Thus the invention also involves a mutant *Chrysosporium* strain which produces less protease than non-mutant *Chrysosporium* strain, for example less than C. lucknowense strain C1 (VKM F-3500 D). In particular the protease activity of such strains is less than half the amount, more in particular less than 30% of the amount produced by C1 strain. The decreased protease activity can be measured by known methods, such as by measuring the halo formed on skim milk plates or BSA degradation.

An embodiment of the invention that is of particular interest is a recombinant *Chrysosporium* according to the invention wherein the nucleic acid sequence encoding the polypeptide of interest encodes a polypeptide that is inactivated or unstable at acid pH i.e. pH below 6, even below pH 5.5, more suitably even below pH 5 and even as low as or lower than pH 4. This is a particularly interesting embodiment, as the generally disclosed fungal expression systems are not cultured under conditions that are neutral to alkaline, but are cultured at acidic pH. Thus the system according to the invention provides a safe fungal expression system for proteins or polypeptides that are susceptible to being inactivated or are unstable at acid pH.

Quite specifically a recombinant strain as defined in any of the embodiments according to the invention, wherein the nucleic acid sequence encoding the polypeptide of interest encodes a protein or polypeptide exhibiting optimal activity and/or stability at a pH above 5, preferably at neutral or alkaline pH (i.e. above 7) and/or at a pH higher than 6, is considered a preferred embodiment of the invention. More than 50%, more than 70% and even more than 90% of optimal activities at such pH values are anticipated as being particularly useful embodiments. A polypeptide expressed under the cultivation conditions does not necessarily have to be active at the cultivation conditions, in fact it can be advantageous for it to be cultured under conditions under which it is inactive as its active form could be detrimental to the host. This is the case for proteases for example. What is however required is for the protein or polypeptide to be stable under the cultivation conditions. The stability can be thermal stability. It can also be stability against specific compositions or chemicals, such as are present for example in compositions or processes of production or application of the polypeptide or protein of interest. Linear alkylbenzene sulfonate (LAS) in detergent compositions comprising cellulases or lipases, etc. is an example of a chemical often detrimental to proteins. The time periods of use in applications can vary from short to long exposure so stability can be over a varying length of time varying per application. The skilled person will be able to ascertain the correct conditions on a case by case basis. One can use a number of commercially available assays to determine the optimal activities of the various enzymatic products. The catalogues of Sigma and Megazyme for example show such. Specific examples of tests are mentioned elsewhere in the description. The manufacturers provide guidance on the application.

We have surprisingly found that a *Chrysosporium* strain that can be suitably used to transform or transfect with the sequence of interest to be expressed is a strain exhibiting relatively low biomass. We have found that *Chrysosporium* strains having a biomass two to five times lower than that of *Trichoderma reesei* when cultured to a viscosity of 200-600 cP at the end of fermentation and exhibiting a biomass of 10 to 20 times lower than that of *Aspergillus niger* when cultured to a viscosity of 1500-2000 cP under corresponding conditions, i.e. their respective optimal cultivation conditions can provide a high level of expression. This level of expression far exceeds that of the two commercial reference strains at a much lower biomass and at much lower viscosity. This means that the yield of expression of such *Chrysosporium* strains will be appreciably higher than from *Aspergillus niger* and *Trichoderma reesei*. Such a transformed or transfected *Chrysosporium* strain forms a suitable embodiment of the invention.

We find a biomass of 0.5-1.0 g/l for *Chrysosporium* strain C1(18-25) as opposed to 2.5-5.5 g/l for *Trichoderma reesei* and 5-10 g/l of *Aspergillus niger* under the above described conditions. In the Examples we provide details of this process.

In a suitable embodiment a recombinant *Chrysosporium* strain according to the invention produces protein or polypeptide in at least the amount equivalent to the production in moles per liter of cellulase by the strain UV13-6 or NG7C-19, and most preferably at least equivalent to or higher than that of the strain UV18-25 under the corresponding or identical conditions, i.e. their respective optimal cultivation conditions.

Unexpectedly we have also found that expression and secretion rates are exceedingly high when using a *Chrysosporium* strain exhibiting the mycelial morphology of strain UV18-25 i.e. fragmented short mycelia. Thus a recombinant strain according to the invention will preferably exhibit such morphology. The invention however also covers non-recombinant strains or otherwise engineered strains of *Chrysosporium* exhibiting this novel and inventive characteristic. Also covered by the invention is a recombinant *Chrysosporium* strain in any of the embodiments described according to the invention further exhibiting reduced sporulation in comparison to C1, preferably below that of strain UV13-6, preferably below that of NG7C-19, preferably below that of UV18-25 under equivalent fermenter conditions. Also covered by the invention is a recombinant *Chrysosporium* strain in any of the embodiments described according to the invention further exhibiting at least the amount of protein production ratio to biomass in comparison to C1, preferably in comparison to that of any of strains UV13-6, NG7C-19 and UV18-25 under equivalent fermenter conditions. The invention however also covers non-recombinant strains or otherwise engineered strains of *Chrysosporium* exhibiting this novel and inventive characteristic as such or in combination with any of the other embodiments.

Another attractive embodiment of the invention also covers a recombinant *Chrysosporium* strain exhibiting a viscosity below that of strain NG7C-19, preferably below that of UV18-25 under corresponding or identical fermenter conditions. The invention however also covers non-recombinant strains or otherwise engineered strains of *Chrysosporium* exhibiting this novel and inventive characteristic as such or in combination with any of the other embodiments. We have determined that the viscosity of a culture of UV18-25 is below 10 cP opposed to that of *Trichoderma reesei* being of the order 200-600 cP, with that of *Aspergillus niger* being of the order 1500-2000 cP under their respective optimal culture conditions at the end of fermentation. The process used for such determination is provided in the examples.

Viscosity can be assessed in many cases by visual monitoring. The fluidity of the substance can vary to such a large extent that it can be nearly solid, sauce like or liquid. Viscosity can also readily be ascertained by Brookfield rotational viscometry, use of kinematic viscosity tubes, falling ball viscometer or cup type viscometer. The yields from such a low viscosity culture are higher than from the commercial known higher viscosity cultures per time unit and per cell.

The processing of such low viscosity cultures according to the invention is advantageous in particular when the cultures are scaled up. The subject *Chrysosporium* strains with the low viscosity perform very well in cultures as large as up to 150,000 liter cultures. Thus any culture size up to 150,000 liters provides a useful embodiment of the invention. Any other conventional size of fermentation should be carried out well with the strains according to the invention. The reasoning behind this is that problems can arise in large scale production with the formation of aggregates that have mycelia that are too dense and/or are unevenly distributed. The media as a result cannot be effectively utilised during the culture thus leading to an inefficient production process in particular in large scale fermentations i.e. over 150,000 liters. Aeration and mixing become problematic leading to oxygen and nutrient starvation and thus reduced concentration of productive biomass and reduced yield of polypeptide during the culture and/or can result in longer fermentation times. In addition high viscosity and high shear are not desirable in commercial fermentation processes and in current commercial processes they are the production limiting factors. All these negative aspects can be overcome by the *Chrysosporium* host according to the invention which exhibits much better characteristics than *Trichoderma reesei*, *Aspergillus niger* and *Aspergillus oryzae* that are commercially used in this respect i.e. exhibits better protein production levels and viscosity properties and biomass figures.

A *Chrysosporium* strain selected from C1, UV13-6, NG7C-19 and UV18-25 illustrates various aspects of the invention exceedingly well. The invention however also covers recombinant strains or otherwise engineered strains of *Chrysosporium* derived from the four deposited strains that also exhibit any of the novel and inventive characteristics as such or in combination. The deposit data for these strains have been presented elsewhere in the description. The invention also covers recombinant strains or otherwise engineered strains of *Chrysosporium* derived from the four deposited strains that also exhibit any of the novel and inventive characteristics as such or in combination. A *Chrysosporium* strain according to the invention also comprises a strain exhibiting under the corresponding culture conditions a biomass at least twice as low as that of *Trichoderma reesei*, suitably even more up to 5 times lower than that of *Trichoderma reesei*, specifically of a *Trichoderma reesei* exhibiting a viscosity of 200-600 cP as disclosed under the conditions of the examples. A *Chrysosporium* strain according to the invention also comprises a strain producing the polypeptide in at least the amount in moles per liter of cellulase by the strain C1, UV13-6, NG7C-19 or UV18-25 under the corresponding or identical conditions.

*Chrysosporium* strains according to the invention are further preferred if they exhibit optimal growth conditions at neutral to alkaline pH and temperatures of 25-43° C. A preference can exist for neutral and even for alkaline pH. Such production conditions are advantageous to a number of polypeptides and proteins, in particular those susceptible to attack by acidic pH or those that are inactive or unstable at low temperatures. It is however also an embodiment of the invention to include *Chrysosporium* strains that can be cultured at acidic pH as this can be useful for certain proteins and polypeptides. A suitable acidic pH lies from 7.0. An acidic pH lower than 6.5 is envisaged as providing a good embodiment of the invention. A pH around 5.0-7.0 is also a suitable embodiment. A neutral pH can be 7.0 or around 7 e.g. 6.5-7.5. As stated elsewhere the pH of optimal interest depends on a number of factors that will be apparent to the person skilled in the art. A pH higher than 7.5 is alkaline, suitably between 7.5-9.0 can be used.

When comparing data of strains according to the invention with other strains perhaps having other optimal conditions (e.g. *Aspergillus* and *Trichoderma*) for viscosity measurements, biomass determination or protein production comparisons should be made using the relevant optimal conditions for the relevant strain. This will be obvious to the person skilled in the art.

A *Chrysosporium* strain according to any of the above-mentioned embodiments of the invention, said strain further exhibiting production of one or more of the fungal enzymes selected from the carbohydrate-degrading enzymes, proteases, other hydrolases, oxidoreductase, and transferases mentioned above is considered a particularly useful embodiment of the invention. The most interesting products are specifically cellulases, xylanases, pectinases, lipases and proteases. Also useful as embodiment of the invention however is a *Chrysosporium* strain exhibiting production of one or more fungal enzymes that exhibit neutral or alkaline optimal stability and/or activity, preferably alkaline optimal stability and/or activity, said enzyme being selected from carbohydrate-degrading enzymes, hydrolases and proteases, preferably hydrolases and carbohydrate-degrading enzymes. In the case of non-recombinant *Chrysosporium*, such enzymes are suitably other than cellulase as disclosed in WO 98/15633. Enzymes of particular interest are xylanases, proteases, esterases, alpha-galactosidases, beta-galactosidases, beta-glucanases and pectinases. The enzymes are not limited to the aforementioned. The comments vis-à-vis stability and activity elsewhere in the description are valid here also.

The invention also covers a method of producing a polypeptide of interest, said method comprising culturing a *Chrysosporium* strain in any of the embodiments according to the invention under conditions permitting expression and preferably secretion of the polypeptide and recovering the subsequently produced polypeptide of interest.

Where protein or polypeptide is mentioned, variants and mutants e.g. substitution, insertion or deletion mutants of naturally occurring proteins are intended to be included that exhibit the activity of the non-mutant. The same is valid vis-à-vis the corresponding nucleic acid sequences. Processes such as gene shuffling, protein engineering and directed evolution, site directed mutagenesis and random mutagenesis are processes through which such polypeptides, variants or mutants can be obtained. U.S. Pat. No. 5,223,409, U.S. Pat. No. 5,780,279 and U.S. Pat. No. 5,770,356 provide teaching of directed evolution. Using this process a library of randomly mutated gene sequences created for example by gene shuffling via error prone PCR occurs in any cell type. Each gene has a secretion region and an immobilising region attached to it such that the resulting protein is secreted and stays fixed to the host surface. Subsequently conditions are created that necessitate the biological activity of the particular polypeptide. This occurs for a number of cycles ultimately leading to a final gene with the desired characteristics. In other words a speeded up directed process of evolution. U.S. Pat. No. 5,763,192 also describes a process for obtaining DNA, RNA, peptides, polypeptides or protein by way of synthetic polynucleotide coupling stochastically generated sequences, introduction thereof into a host followed by selection of the host cell with the corresponding predetermined characteristic.

Another application of the method of the present invention is in the process of "directed evolution", wherein novel protein-encoding DNA sequences are generated, the encoded proteins are expressed in a host cell, and those sequences encoding proteins having a desired characteristic are mutated and expressed again. The process is repeated for a number of cycles until a protein with the desired characteristics is obtained. Gene shuffling, protein engineering, error-prone PCR, site-directed mutagenesis, and combinatorial and random mutagenesis are examples of processes through which novel DNA sequences encoding exogenous proteins can be generated. U.S. Pat. Nos. 5,223,409, 5,780,279 and 5,770,356 provide teaching of directed evolution. See also Kuchner and Arnold, Trends in Biotechnology, 15:523-530 (1997); Schmidt-Dannert and Arnold, Trends in Biotech., 17:135-136 (1999); Arnold and Volkov, Curr. Opin. Chem. Biol., 3:54-59 (1999); Zhao et al., Manual of Industrial Microbiology and Biotechnology, 2nd Ed., (Demain and Davies, eds.) pp. 597-604, ASM Press, Washington D.C., 1999; Arnold and Wintrode, Encyclopedia of Bioprocess Technology Fermentation, Biocatalysis, and Bioseparation, (Flickinger and Drew, eds.) pp. 971-987, John Wiley & Sons, New York, 1999; and Minshull and Stemmer, Curr. Opin. Chem. Biol. 3:284-290.

An application of combinatorial mutagenesis is disclosed in Hu et al., Biochemistry. 1998 37:10006-10015. U.S. Pat. No. 5,763,192 describes a process for obtaining novel protein-encoding DNA sequences by stochastically generating synthetic sequences, introducing them into a host, and selecting host cells with the desired characteristic. Methods for effecting artificial gene recombination (DNA shuffling) include random priming recombination (Z. Shao, et al., Nucleic Acids Res., 26:681-683 (1998)), the staggered extension process (H. Zhao et al., Nature Biotech., 16:258-262 (1998)), and heteroduplex recombination (A. Volkov et al., Nucleic Acids Res., 27:e18 (1999)). Error-prone PCR is yet another approach (Song and Rhee, Appl. Environ. Microbiol. 66:890-894 (2000)).

There are two widely-practiced methods of carrying out the selection step in a directed evolution process. In one method, the protein activity of interest is somehow made essential to the survival of the host cells. For example, if the activity desired is a cellulase active at pH 8, a cellulase gene could be mutated and introduced into the host cells. The transformants are grown with cellulose as the sole carbon source, and the pH raised gradually until only a few survivors remain. The mutated cellulase gene from the survivors, which presumably encodes a cellulase active at relatively high pH, is subjected to another round of mutation, and the process is repeated until transformants that can grow on cellulose at pH 8 are obtained. Thermostable variants of enzymes can likewise be evolved, by cycles of gene mutation and high-temperature culturing of host cells (Liao et al., Proc. Natl. Acad. Sci. USA 83:576-580 (1986); Giver et al., Proc. Natl. Acad. Sci. USA. 95:12809-12813 (1998).

An alternative to the massively parallel "survival of the fittest" approach is serial screening. In this approach, individual transformants are screened by traditional methods, such as observation of cleared or colored zones around colonies growing on indicator media, colorimetric or fluorometric enzyme assays, immunoassays, binding assays, etc. See for example Joo et al., Nature 399:670-673 (1999), where a cytochrome P450 monooxygenase not requiring NADH as a cofactor was evolved by cycles of mutation and screening; May et al., Nature Biotech. 18:317-320 (2000), where a hydantoinase of reversed stereoselectivity was evolved in a similar fashion; and Miyazaki et al., J. Mol. Biol. 297:1015-1026 (2000), where a thermostable subtilisin was evolved.

Standard cloning and protein or polypeptide isolation techniques can be used to arrive at the required sequence information. Parts of known sequences can be used as probes to isolate other homologues in other genera and strains. The nucleic acid sequence encoding a particular enzyme activity can be used to screen a *Chrysosporium* library for example. A person skilled in the art will realise which hybridisation conditions are appropriate. Conventional methods for nucleic acid hybridisation construction of libraries and cloning techniques are described in Sambrook et al (Eds) (1989) In "Molecular Cloning. A Laboratory Manual" Cold Spring Harbor Press, Plainview, N.Y., and Ausubel et al (Eds) "Current Protocols in Molecular Biology" (1987) John Wiley and Sons, New York. The relevant information can also be derived from later handbooks and patents, as well as from various commercially available kits in the field.

In an alternative embodiment, said method comprises culturing a strain according to the invention under conditions permitting expression and preferably secretion of the protein or polypeptide or precursor thereof and recovering the subsequently produced polypeptide and optionally subjecting the precursor to additional isolation and purification steps to obtain the polypeptide of interest. Such a method may suitably comprise a cleavage step of the precursor into the polypeptide or precursor of interest. The cleavage step can be cleavage with a Kex-2 like protease, any basic amino acid paired protease or Kex-2 for example when a protease cleavage site links a well secreted protein carrier and the polypeptide of interest. A person skilled in the art can readily find Kex-2-like protease sequences as consensus sequence details for such are available and a number of alternatives have already been disclosed e.g. furin.

Suitably in a method for production of the polypeptide according to any of the embodiments of the invention the cultivation occurs at pH higher than 5, preferably 5-10, more preferably 6-9. Suitably in such a method the cultivation occurs at a temperature between 25-43° C., preferably 30-40° C. The *Chrysosporium* strain used in the method according to the invention is quite suitably a recombinant *Chrysosporium* strain according to any of the embodiments disclosed. The method according to the invention in such a case can further be preceded by the step of production of a recombinant *Chrysosporium* strain according to the invention. The selection of the appropriate conditions will depend on the nature of the polypeptide to be expressed and such selection lies well within the realm of normal activity of a person skilled in the art.

The method of production of a recombinant *Chrysosporium* strain according to the invention is also part of the subject invention. The method comprises stably introducing a nucleic acid sequence encoding a heterologous or homologous polypeptide into a *Chrysosporium* strain, said nucleic acid sequence being operably linked to an expression regulating region, said introduction occurring in a manner known per se for transforming filamentous fungi. As stated above numerous references hereof are available and a small selection has been cited. The information provided is sufficient to enable the skilled person to carry out the method without undue burden. The method comprises introduction of a nucleic acid sequence comprising any of the nucleic acid elements described in the various embodiments of the recombinant *Chrysosporium* according to the invention as such or in combination.

By way of example the introduction can occur using the protoplast transformation method. The method is described in the examples. Alternative protoplast or spheroplast transformation methods are known and can be used as have been described in the prior art for other filamentous fungi. Details of such methods can be found in many of the cited references and are thus incorporated by reference. A method according to the invention suitably comprises using a non-recombinant strain of *Chrysosporium* according to the invention as starting material for introduction of the desired sequence encoding the polypeptide of interest.

The subject invention also covers a method of producing *Chrysosporium* enzyme, said method comprising culturing a *Chrysosporium* strain according to any of the embodiments of the invention as described above in or on a cultivation medium at pH higher than 5, preferably 5-10, more preferably 6-9, suitably 6-7.5, 7.5-9 as examples of neutral and alkaline pH ranges.

The subject invention also covers such a method using a cultivation medium at a temperature between 25-43° C., preferably 30-40° C. The combination of preferred pH and temperature is an especially preferred embodiment of the method of producing *Chrysosporium* enzyme according to the invention.

More in general the invention further covers a method of producing enzymes exhibiting neutral or alkaline optimal activity and/or stability, preferably alkaline optimal activity and/or stability. The preferred ranges vis-à-vis pH and optimal activity as well as assays with which to determine such have been provided elsewhere in the description. The enzyme should be selected from carbohydrate-degrading enzymes, proteases, other hydrolases, oxidoreductases, and transferases, as described above, said method comprising cultivating a host cell transformed or transfected with the corresponding enzyme-encoding nucleic acid sequence. Suitably such an enzyme will be a *Chrysosporium* enzyme. A suitable method such as this comprises production specifically of cellulase, xylanase, pectinase, lipase and protease, wherein cellulase and xylanase cleave-1,4-bonds and cellulase comprises endoglucanase, cellobiohydrolase and -glucosidase. The method according to the invention can comprise cultivating any *Chrysosporium* host according to the invention comprising nucleic acid encoding such aforementioned enzymes. Suitably the production of non-recombinant *Chrysosporium* hosts according to the invention is directed at production of carbohydrate degrading enzymes, hydrolases and proteases. In such a case the enzyme is suitably other than a cellulase. Suitable examples of products to be produced are given in Tables A and B. Methods of isolating are analogous to those described in WO 98/15633 and are incorporated by reference.

The enzymes produced by *Chrysosporium* strains according to the invention are also covered by the invention. Enzymes of *Chrysosporium* origin as can be isolated from non-recombinant *Chrysosporium* strains according to the invention are also covered. They exhibit the aforementioned stability, activity characteristics. Suitably they are stable in the presence of LAS. In particular proteases with pI 4-9.5, proteases with a MW of 25-95 kD, xylanases with pI between 4.0 and 9.5, xylanases with MW between 25 and 65 kD, endoglucanases with a pI between 3.5 and 6.5, endoglucanases with MW of 25-55 kDa, β-glucosidases, α,β-galactosidases with a pI of 4-4.5, β-glucosidases, α,β-galactosidases with a MW of 45-50 kDa, cellobiohydrolases of pI 4-5, cellobiohydrolases of MW 45-75 kDa, e.g. a MW of 55 kD and pI 4.4, polygalacturonases, with a pI of 4.0-5.0 polygalacturonase of 60-70 kDa, e.g. 65 kDa, esterases with a pI 4-5, and esterases with a MW of 95-105 kDa with the afore-mentioned stability, activity characteristics are claimed. The molecular weights (MW) are those determined by SDS-PAGE. The non-recombinant i.e. natively occurring enzyme is other than cellulase as disclosed in WO 98/15633. An enzyme as disclosed in WO 98/15633 is excluded. Enzymes according to the invention are represented by the enzymes of Table B. Enzymes with combinations of the pI values and molecular weights mentioned above are also covered.

The invention is also concerned with the (over)production of non-protein products by the mutant (recombinant) strains of the invention. Such non-protein products include primary metabolites such as organic acids, amino acids, and secondary metabolites such as antibiotics, e.g. penicillins and cephalosporins, and other therapeutics. These products are the result of combinations of biochemical pathways, involving several fungal genes of interest. Fungal primary and secondary metabolites and procedures for producing these metabolites in fungal organisms are well known in the art. Examples of the production of primary metabolites have been described by Mattey M., The Production of Organic Acids, *Current Reviews in Biotechnology*, 12, 87-132 (1992). Examples of the production of secondary metabolites have been described by Penalva et al. The Optimization of Penicillin Biosynthesis in Fungi, *Trends in Biotechnology* 16, 483-489 (1998).

EXAMPLES

Examples of Biomass and Viscosity Determinations

The following operating parameter data ranges have been determined for fungal fermentations using three different fungal organisms. The three fungal organisms compared are: *Trichoderma longibrachiatum* (formerly *T. reesei*), *Aspergillus niger* and *Chrysosporium* lucknowense (UV 18-25).

Viscosity:

Viscosity is determined on a Brookfield LVF viscometer using the small sample adapter and spindle number 31.

Turn the water-circulating pump on 5 minutes prior to viscometer use to equilibrate the water jacket. The water bath temperature should be 30° C.

Obtain a fresh sample of fermentation broth and place 10 ml of the broth in the small sample spindle. Select the spindle speed to give a reading in the range 10-80. Wait four (4) minutes and take the reading from the viscometer scale. Multiply the reading by the factor given below to get the viscosity in centipoise (cP).

| Spindle Speed | Multiplication Factor |
| --- | --- |
| 6 | 50 |
| 12 | 25 |
| 30 | 10 |
| 60 | 5 |

The following viscosity ranges have been determined for fermentations using the specified fungal organism using the above procedure:

| | Viscosity in cP |
| --- | --- |
| *T. longibrachiatum* | 200-600 |
| *A. niger* | 1,500-2,000 |
| *C. lucknowense* (UV18-25) | LT 10 |

Biomass:

Biomass is determined by the following procedure:

Preweigh 5.5 cm filter paper (Whatman 54) in an aluminium weighing dish.

Filter 5.0 ml whole broth through the 5.5 cm paper on a Buchner funnel, wash the filter cake with 10 ml deionised water, place the washed cake and filter in a weighing pan and dry overnight at 60° C. Finish drying at 100° C. for 1 hour, then place in desiccator to cool.

Measure the weight of dried material. Total biomass (g/l) is equal to the difference between the initial and finals weights multiplied by 200. The following biomass ranges have been determined for fermentations using the specified fungal organism using the above procedure:

| | Biomass in g/l |
| --- | --- |
| *T. longibrachiatum* | 2.5-5 |
| *A. niger* | 5-10 |
| *C. lucknowense* (UV18-25) | 0.5-1 |

Protein:

Protein levels were determined using the BioRadBradford Assay Procedure from BioRad Laboratories. Protein levels were highest for the *Chrysosporium*.

The data presented above represent values determined 48 hours into the fermentation process until fermentation end; All values of *Aspergilli* and *Trichoderma* are for commercially relevant fungal organisms and reflect actual commercial data.

A fungal strain such as *C. lucknowense* (UV18-25) has the advantage that the low viscosity permits the use of lower power input and/or shear in the fermentation to meet oxygen demands for those cases where shear stress on the product may be detrimental to productivity due to physical damage of the product molecule. The lower biomass production at high protein production indicates a more efficient organism in the conversion of fermentation media to product. Thus the *Chrysosporium* provides better biomass and viscosity data whilst also delivering at least as much protein, and in fact a lot more protein than the two commercially used systems which obviously are better than for typically deposited *Aspergillus* or *Trichoderma reesei* strains in general public collections.

The high protein production with low biomass concentration produced by *C. lucknowense* (UV18-25) would allow development of fermentation conditions with higher multiples of increase in biomass, if increasing biomass results in increased productivity, for the desired product before reaching limiting fermentation conditions. The present high levels of biomass and viscosity produced by the *T. longibrachiatum* and *A. niger* organisms restrict the increase of biomass as the present levels of biomass and viscosity are near limiting practical fermentation conditions.

Examples of Transformation Comparing *Chrysosporium*, *Trichoderma* and *Tolypocladium* Geodes Two untransformed *Chrysosporium* C1 strains and one *Trichoderma reesei* reference strain were tested on two media (Gs pH 6,8 and Pridham agar, PA, pH 6,8). To test the antibiotic resistance level spores were collected from 7 day old PDA plates. Selective plates were incubated at 32° C. and scored after 2, 4, and 5 days. It followed that the C-1 strains NG7C-19 and UV18-25 clearly have a low basal resistance level both to phleomycin and hygromycin. This level is comparable to that for a reference *T. reesei* commonly used laboratory strain. Thus there is clear indication these two standard fungal selectable markers can be used well in *Chrysosporium* strains. Problems with other standard fungal selectable markers should not be expected.

Selection of Sh-ble (phleomycin-resistance) transformed *Chrysosporium* strains was successfully carried out at 50 µg/ml. This was also the selection level used for *T. reesei* thus showing that differential selection can be easily achieved in *Chrysosporium*. The same comments are valid for transformed strains with hygromycin resistance at a level of 150 µg/ml.

TABLE C

|  | Gs (pH 6.8) | | | Pridham Agar (PA, pH 6.8) | | |
| --- | --- | --- | --- | --- | --- | --- |
|  | NG7C-19 | UV18-25 | T.r.11D5 | NG7C-19 | UV18-25 | T.r.11D5 |
| Phleomycin | 7.5 µg/ml | 10 µg/ml | 5-7.5 µg/ml | 2.5 µg/ml | 10-µg/ml | 2.5 µg/ml |
| Hygromycin | 7.5-10 µg/ml | 10 µg/ml | 10 µg/ml | 15 µg/ml | 25 µg/ml | 15 µg/ml |

The protoplast transformation technique was used on *Chrysosporium* based on the most generally applied fungal transformation technology. All spores from one 90 mm PDA plate were recovered in 8 ml IC1 and transferred into a shake flask of 50 ml IC1 medium for incubation for 15 hours at 35° C. and 200 rpm. After this the culture was centrifuged, the pellet was washed in MnP, brought back into solution in 10 ml MnP and 10 mg/ml Caylase C$_3$ and incubated for 30 minutes at 35° C. with agitation (150 rpm).

The solution was filtered and the filtrate was subjected to centrifugation for 10 minutes at 3500 rpm. The pellet was washed with 10 ml MnPCa$^{2+}$. This was centrifuged for 10 minutes at 25° C. Then 50 microlitres of cold MPC was added. The mixture was kept on ice for 30 minutes whereupon 2.5 ml PMC was added. After 15 minutes at room temperature 500 microlitres of the treated protoplasts were mixed to 3 ml of MnR Soft and immediately plated out on a MnR plate containing phleomycin or hygromycin as selection agent. After incubation for five days at 30° C. transformants were analysed (clones become visible after 48 hours). Transformation efficiency was determined using 10 microgrammes of reference plasmid pAN8-1[19]. The results are presented in the following Table D.

TABLE D

| Transformation efficiency (using 10 g of reference plasmid pAN8-1) | | | |
| --- | --- | --- | --- |
|  | T. reesei | NG7C-19 | UV18-25 |
| Viability | $10^6$/200 µl | 5 $10^6$/200 µl | 5 $10^6$/200 µl |
| Transformants Per 200 µl | 2500 | $10^4$ | $10^4$ |
| Transformants per $10^6$ viable cells | 2500 | 2000 | 2000 |

The results show that the *Chrysosporium* transformants viability is superior to that of *Trichoderma*. The transformability of the strains is comparable and thus the number of transformants obtained in one experiment lies 4 times higher for *Chrysosporium* than for *T. reesei*. Thus the *Chrysosporium* transformation system not only equals the commonly used *T. reesei* system, but even outperforms it. This improvement can prove especially useful for vectors that are less transformation efficient than pAN8-1. Examples of such less efficient transformation vectors are protein carrier vectors for production of non-fungal proteins which generally yield 10 times fewer transformants.

A number of other transformation and expression vectors were constructed with homologous *Chrysosporium* protein encoding sequences and also with heterologous protein encoding sequences for use in transformation experiments with *Chrysosporium*. The vector maps are provided in the FIGS. 6-11.

The homologous protein to be expressed was selected from the group of cellulases produced by *Chrysosporium* and consisted of endoglucanase 6 which belongs to family 6 (MW 43 kDa) and the heterologous protein was endoglucanase 3 which belongs to family 12 (MW 25 kDa) of *Penicillium*.

pF6g comprises *Chrysosporium* endoglucanase 6 promoter fragment linked to endoglucanase 6 signal sequence in frame with the endoglucanase 6 open reading frame followed by the endoglucanase 6 terminator sequence. Transformant selection is carried out by using cotransformation with a selectable vector.

pUT1150 comprises *Trichoderma reesei* cellobiohydrolase promoter linked to endoglucanase 6 signal sequence in frame with the endoglucanase 6 open reading frame followed by the *T. reesei* cellobiohydrolase terminator sequence. In addition this vector carries a second expression cassette with a selection marker i.e. the phleomycin resistance gene (Sh-ble gene).

pUT1152 comprises *Aspergillus nidulans* glyceraldehyde-3-phosphate dehydrogenase A promoter linked to endoglucanase 6 signal sequence in frame with the endoglucanase 6 open reading frame followed by the *A. nidulans* anthranilate synthase (trpC) terminator sequence. In addition this vector carries a second expression cassette with a selection marker i.e. the phleomycin resistance gene (Sh-ble gene).

pUT1155 comprises *A. nidulans* glyceraldehyde-3-phosphate dehydrogenase A promoter linked to *Trichoderma reesei* cellobiohydrolase signal sequence in frame with the carrier protein Sh-ble which in turn is linked in frame to the endoglucanase 6 open reading frame followed by the *A. nidulans* trpC terminator sequence. This vector uses the technology of the carrier protein fused to the protein of interest which is known to very much improve the secretion of the protein of interest.

pUT1160 comprises *Aspergillus nidulans* glyceraldehyde-3-phosphate dehydrogenase A promoter linked to *Trichoderma reesei* cellobiohydrolase signal sequence in frame with the carrier protein Sh-ble which in turn is linked in frame to the endoglucanase 3 open reading frame of *Penicillium* followed by the *A. nidulans* trpC terminator sequence.

pUT1162 comprises *Trichoderma reesei* cellobiohydrolase promoter linked to endoglucanase 3 signal sequence in frame with the endoglucanase 3 open reading frame of *Penicillium* followed by the *T. reesei* cellobiohydrolase terminator sequence. In addition this vector carries a second expression cassette with a selection marker i.e. the phleomycin resistance gene (Sh-ble gene).

Further examples of expression systems include a *Chrysosporium* endoglucanase 3 promoter fragment linked to endoglucanase 3 signal sequence in frame with the endoglucanase 3 open reading frame followed by the endoglucanase 3 terminator sequence. Transformant selection is carried out by using cotransformation with a selectable vector.

Another example is a *Chrysosporium lucknowense* cellobiohydrolase promoter linked to *Penicillium* endoglucanase 3 signal sequence in frame with the *Penicillium* endoglucanase 3 open reading frame followed by the *Chrysosporium* cellobiohydrolase terminator sequence. In addition this vector carries a second expression cassette with a selection marker i.e. the aceetamidase S gene (AmdS gene).

A further example comprises *Chrysosporium* glyceraldehyde-3-phosphate dehydrogenase 1 promoter linked to the *Aspergillus niger* glucoamylase signal sequence and the glucoamylase open reading frame fused to the human Interleukine 6 open reading frame. In addition this vector carries a second expression cassette with a selection marker i.e. the AmdS gene.

A still further example is a *Aspergillus nidulans* glyceraldehyde-3-phosphate dehydrogenase A promoter linked to the endoglucanase 5 open reading frame followed by a *Aspergillus nidulans* terminator sequence.

TABLE E

Comparative transformations

| Vector | Strain | Transformation | No of transf. | Tested in liquid culture |
|---|---|---|---|---|
| PUT1150 | UV18-25 | selection phleo | 285 | 5 |
|  | T. geodes | selection phleo | 144 | 5 |
| PUT1152 | UV18-25 | cotransformationpAN8.1 | 398 | 5 |
|  | T. geodes | cotransformationpAN8.1 | 45 | 4 |
| PF6g | UV18-25 | cotransformationpAN8.1 | 252 | 6 |
|  | T. geodes | cotransformationpAN8.1 | 127 | 5 |
| PUT1162 | UV18-25 | selection phleo | >400 |  |
|  | T. geodes | Not done yet |  |  |

Table E shows the results of transformation of both *Chrysosporium* UV18-25 and *Tolypocladium* geodes. The transformation protocol used is described in the section for heterologous transformation.

Examples of Heterologous and Homologous Expression of *Chrysosporium* Transformants C1 strains (NG7C-19 and/or UV18-25) have been tested for their ability to secrete various heterologous proteins: a bacterial protein (*Streptoalloteichus hindustanus* phleomycin-resistance protein, Sh ble), a fungal protein (*Trichoderma reesei* xylanase II, XYN2) and a human protein (the human lysozyme, HLZ).

The details of the process are as follows:

[1] C1 Secretion of *Streptoalloteichus hindustanus* Phleomycin-Resistance Protein (Sh ble).

C1 strains NG7C-19 and UV 18-25 have been transformed by the plasmid pUT720[1]. This vector presents the following fungal expression cassette:

*Aspergillus nidulans* glyceraldehyde-3-phosphate dehydrogenase (gpdA) promoter[2]

A synthetic *Trichoderma reesei* cellobiohydrolase I (cbh1) signal sequence[1,3]

*Streptoalloteichus hindustanus* phleomycin-resistance gene Sh ble[4]

*Aspergillus nidulans* tryptophan-synthase (trpC) terminator[5]

Figure 2:
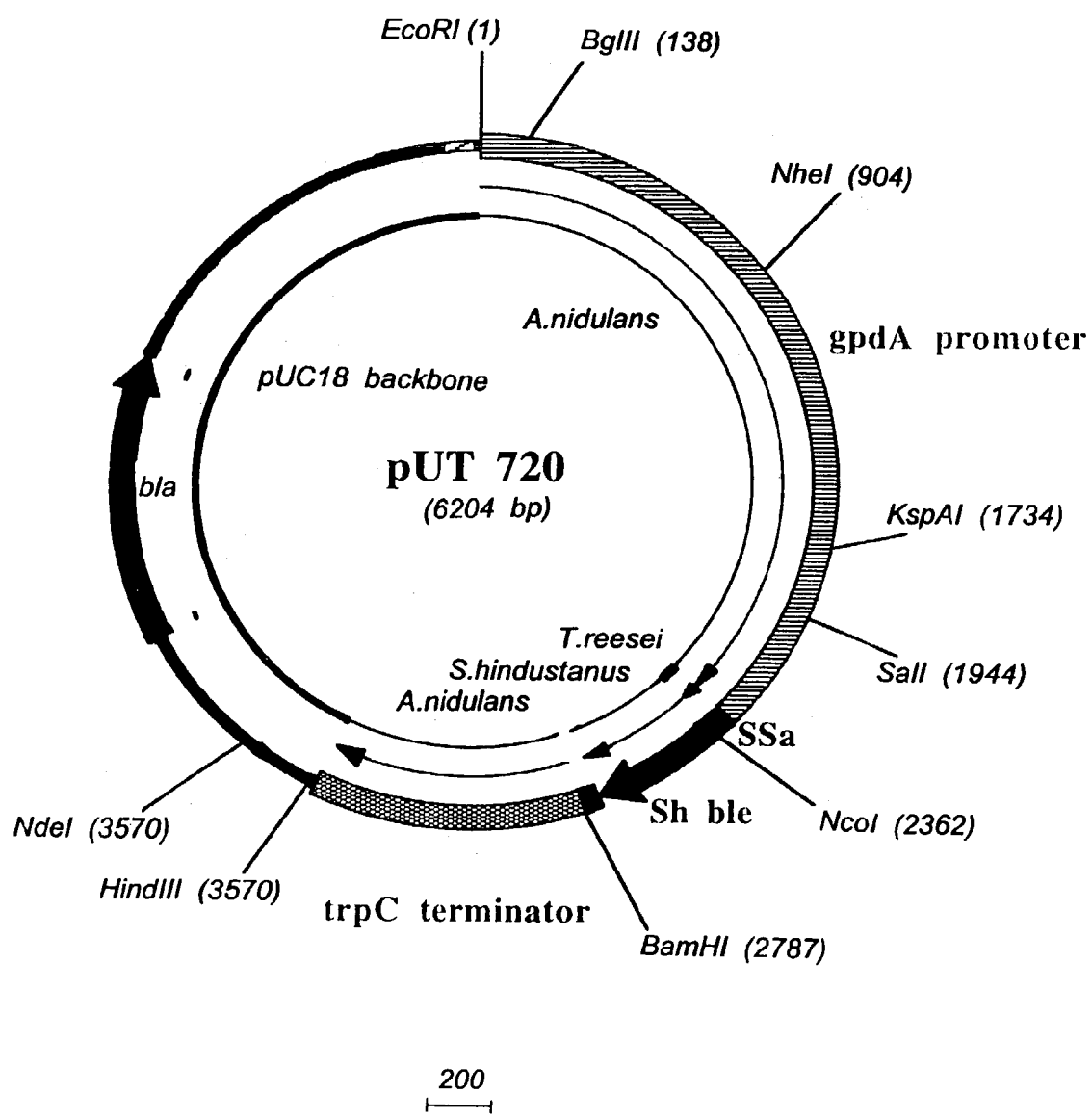
FIG. 2 is a pUT720 map

The vector also carries the beta-lactamase gene (bla) and *E. coli* replication origin from plasmid pUC18[6] The detailed plasmid map is provided in FIG. 2.

C1 protoplasts were transformed according to Durand et al.[7] adapted to C1 (media & solutions composition is given elsewhere): All spores from one 90 mm PDA plate of untransformed C1 strain were recovered in 8 ml IC1 and transferred into a shake flask with 50 ml IC1 medium for incubation 15 hours at 35° C. and 150 rpm. Thereupon, the culture was spun down, the pellet washed in MnP, resolved in 10 ml MnP+10 mg/ml Caylase $C_3$, and incubated 30 min at 35° C. with agitation (150 rpm). The solution was filtered and the filtrate was centrifuged 10 min at 3500 rpm. The pellet was washed with 10 ml $MnPCa^{2+}$. This was spun down 10 min at 3500 rpm and the pellet was taken up into 1 ml $MnPCa^{2+}$. 10 μg of pUT720 DNA were added to 200 μl of protoplast solution and incubated 10 min at room temperature (~20° C.). Then, 50 μl of cold MPC was added. The mixture was kept on ice for 30 min whereupon 2.5 ml PMC was added. After 15 min at room temperature 500 μl of the treated protoplasts were mixed to 3 ml of MnR Soft and immediately plated out on a MnR plate containing phleomycin (50 μg/ml at pH6.5) as selection agent. After 5 days incubation at 30° C., transformants were analysed (clones start to be visible after 48 hours).

The Sh ble production of C1 transformants (phleomycin-resistant clones) was analysed as follows: Primary transformants were toothpicked to GS+phleomycin (5 μg/ml) plates and grown for 5 days at 32° C. for resistance verification. Each validated resistant clone was subcloned onto GS plates. Two subclones per transformant were used to inoculate PDA plates in order to get spores for liquid culture initiation. The liquid cultures in IC1 were grown 5 days at 27° C. (shaking 200 rpm). Then, the cultures were centrifuged (5000 g, 10 min.) and 500 μl of supernatant were collected. From these samples, the proteins were precipitated with TCA and resuspended in Western Sample Buffer to 4 mg/ml of total proteins (Lowry Method[8]). 10 μl (about 40 μg of total proteins) were loaded on a 12% acrylamide/SDS gel and run (BioRad Mini Trans-Blot system). Western blotting was conducted according to BioRad instructions (Schleicher & Schull 0.2 μm membrane) using rabbit anti-Sh ble antiserum (Cayla Cat. Ref. #ANTI-0010) as primary antibody.

The results are shown in FIG. 1 and Table F:

TABLE F

Sh ble estimated production levels in C1

|  | Estimated Sh ble quantity on the Western blot | Estimated Sh ble concentration in the production media |
|---|---|---|
| UntransformedNG7C-19 | Not detectable |  |
| NG7C-19::720clone 4-1 | 25 ng | 0.25 mg/l |
| NG7C-19::720clone 5-1 | 25 ng | 0.25 mg/l |
| NG7C-19::720clone 2-2 | 250 ng | 2.5 mg/l |
| Untransformed UV18-25 | Not detectable |  |
| UV18-25::720clone 1-2 | 500 ng | 5 mg/l |
| UV18-25::720clone 3-1 | 250 ng | 2.5 mg/l |

These data show that:
1) The heterologous transcription/translation signals from pUT720 are functional in *Chrysosporium*.
2) The heterologous signal sequence of pUT720 is functional in *Chrysosporium*.
3) *Chrysosporium* can be used a host for the secretion of an heterologous bacterial protein.

[2] C1 Secretion of the Human Lysozyme (HLZ).

C1 strains NG7C-19 and UV18-25 have been transformed by the plasmid pUT970G 9. This vector presents the following fungal expression cassette:

*Aspergillus nidulans* lyceraldehyde-3-phosphate dehydrogenase (gpdA) promoter[2]

A synthetic *Trichoderma reesei* cellobiohydrolase I (cbh1) signal sequence[1,3]

*Streptoalloteichus hindustanus* phleomycin-resistance gene Sh ble[4] used as carrier-protein[10]

*Aspergillus niger* glucoamylase (glaA2) hinge domain cloned from plasmid pAN56-2[11,12]

A linker peptide (LGERK) featuring a KEX2-like protease cleavage site[1]

A synthetic human lysozyme gene (hlz)[10]

*Aspergillus nidulans* tryptophan-synthase (trpC) terminator[5]

Figure 3:
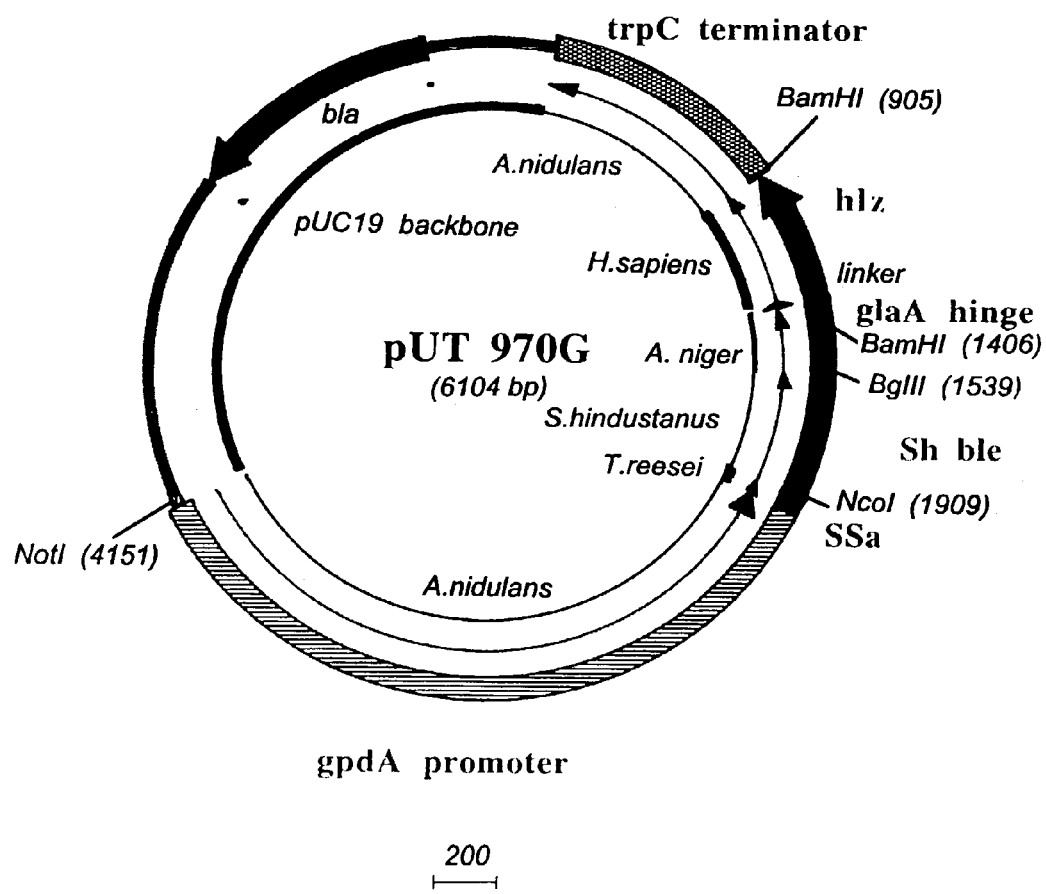
FIG. 3 is a pUT970G map

The vector also carries the beta-lactamase gene (bla) and *E. coli* replication origin from plasmid pUC18[6]. The detailed plasmid map is provided in FIG. 3.

C1 protoplasts were transformed with plasmid pUT970G following the same procedure already described in example 1. The fusion protein (Sh ble::GAM hinge::HLZ) is functional with respect to the phleomycin-resistance thus allowing easy selection of the C1 transformants. Moreover, the level of phleomycin resistance correlates roughly with the level of hlz expression.

The HLZ production of C1 transformants (phleomycin-resistant clones) was analysed by lysozyme-activity assay as follow: Primary transformants were toothpicked to GS+phleomycin (51 g/ml) plates (resistance verification) and also on LYSO plates (HLZ activity detection by clearing zone visualisation[1,10]). Plates were grown for 5 days at 32° C. Each validated clone was subcloned onto LYSO plates. Two subclones per transformant were used to inoculate PDA plates in order to get spores for liquid culture initiation. The liquid cultures in IC1 were grown 5 days at 27° C. (shaking 180 rpm). Then, the cultures were centrifuged (5000 g, 10 min.). From these samples, lysozyme activity was measured according to Mörsky et al.[13].

TABLE G

Active HLZ production levels in C1

| | Active HLZ concentration in culture media |
|---|---|
| UntransformedNG7C-19 | 0 mg/l |
| NG7C-19::970G clone 4 | 4 mg/l |
| NG7C-19::970G clone 5 | 11 mg/l |
| UntransformedUV18-25 | 0 mg/l |
| UV18-25::970G clone 1 | 8 mg/l |
| UV18-25::970G clone 2 | 4 mg/l |
| UV18-25::970G clone 3 | 2 mg/l |
| UV18-25::970G clone 2 | 2.5 mg/l |

These data show that:
1) Points 1 & 2 from example 1 are confirmed.
2) Sh ble is functional in *Chrysosporium* as resistance-marker.
3) Sh ble is functional in *Chrysosporium* as carrier-protein.
4) The KEX2-like protease cleavage site is functional in *Chrysosporium* (otherwise HLZ wouldn't be active).
5) *Chrysosporium* can be used as host for the secretion of a heterologous mammalian protein.

[3] C1 Secretion of *Trichoderma reesei* Xylanase II (XYN2).

C1 strain UV18-25 has been transformed by the plasmids pUT1064 and pUT1065.

pUT1064 presents the two following fungal expression cassettes:

The first cassette allows the selection of phleomycin-resistant transformants:

*Neurospora crassa* cross-pathway control gene 1 (cpc-1) promoter[14]

*Streptoalloteichus hindustanus* phleomycin-resistance gene Sh ble[4]

*Aspergillus nidulans* tryptophan-synthase (trpC) terminator[5]

The second cassette is the xylanase production cassette:

*T. reesei*_strain TR2 cbh1 promoter[15]

*T. reesei*_strain TR2 xyn2 gene (including its signal sequence)[16]

*T. reesei*_strain TR2 cbh1 terminator[15]

Figure 4:
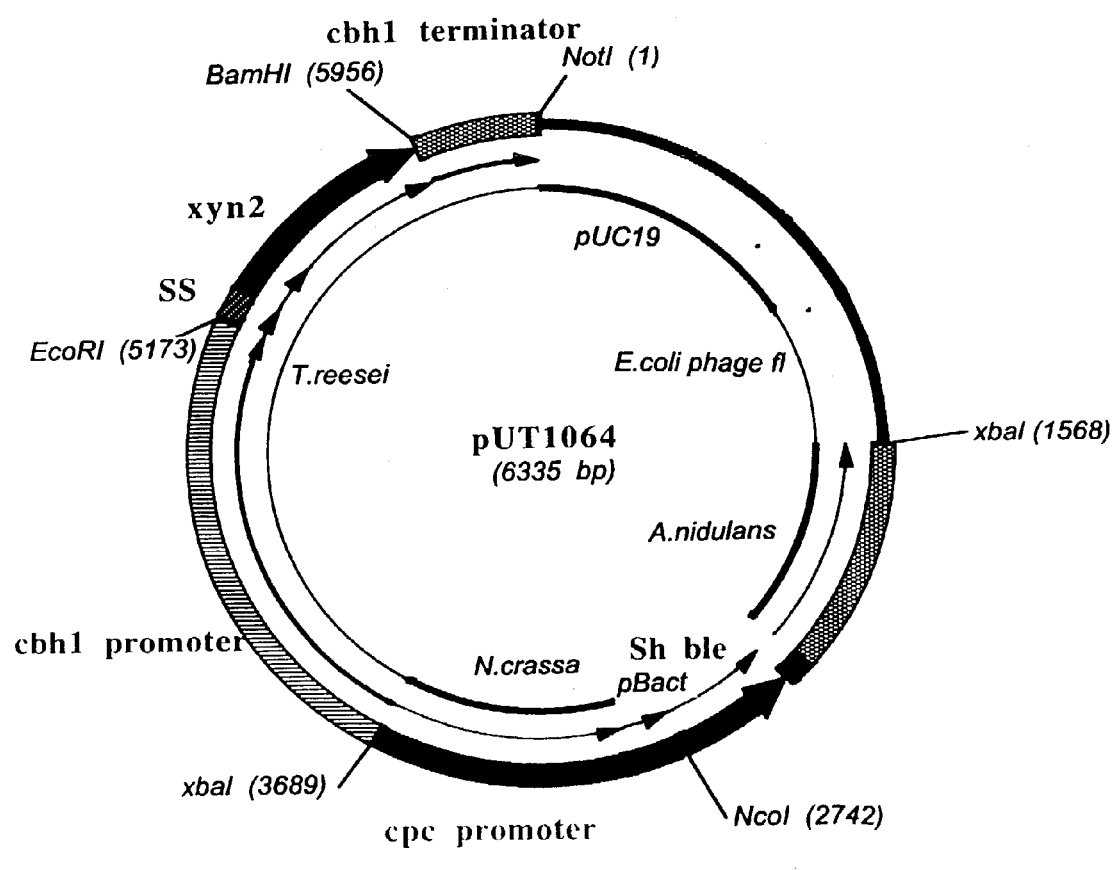
FIG. 4 is a pUT1064 map

The vector also carries an *E. coli* replication origin from plasmid pUC 19[6]. The plasmid detailed map is provided in FIG. 4.

pUT1065 presents the following fungal expression cassette:

*A. nidulans*_glyceraldehyde-3-phosphate dehydrogenase (gpdA) promoter[2]

A synthetic *T._reesei* cellobiohydrolase I (cbh1) signal sequence[1,3]

*S. hindustanus* phleomycin-resistance gene Sh ble[4] used as carrier-protein[10]

A linker peptide (SGERK) featuring a KEX2-like protease cleavage site[1]

*T. reesei*_strain TR2xyn2 gene (without signal sequence)[16]

*A. nidulans* tryptophan-synthase (trpC) terminator[5]

Figure 5:
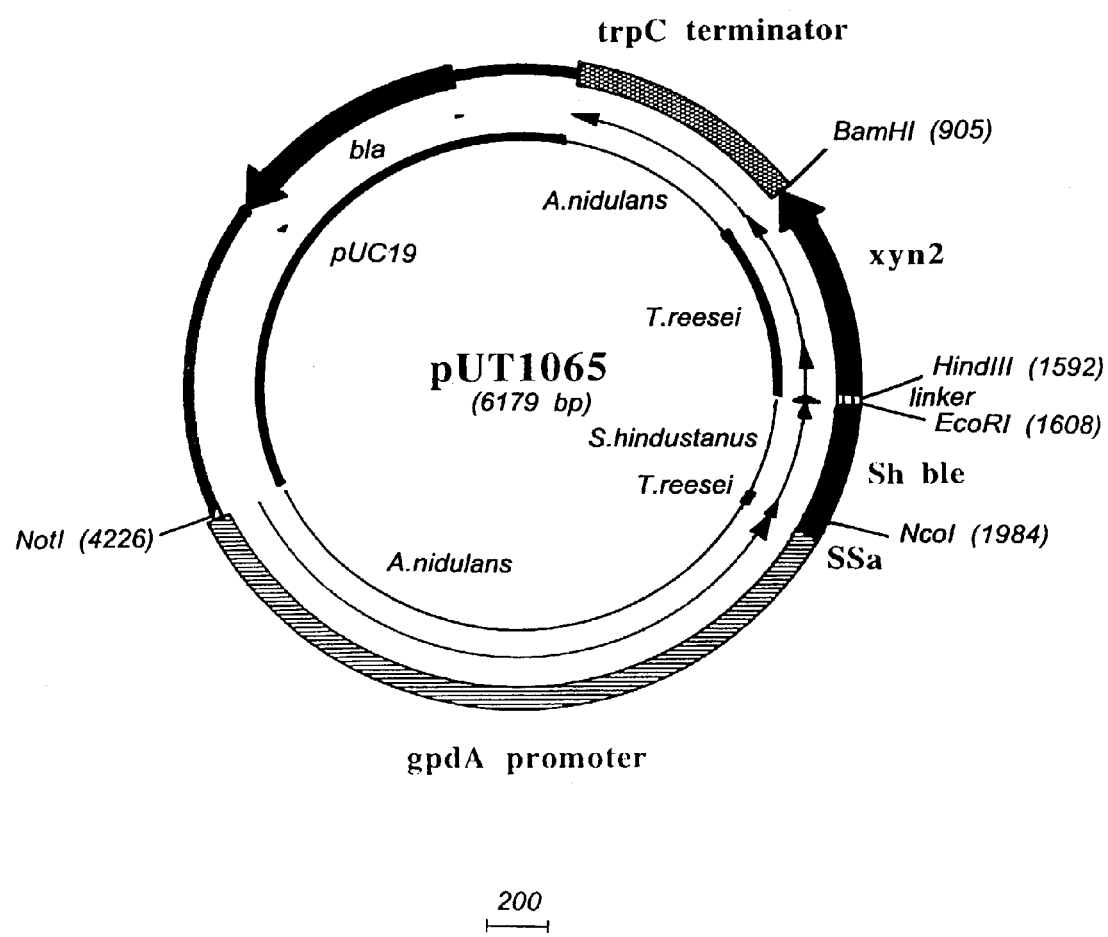
FIG. 5 is apUT1065 map
Figure 6:
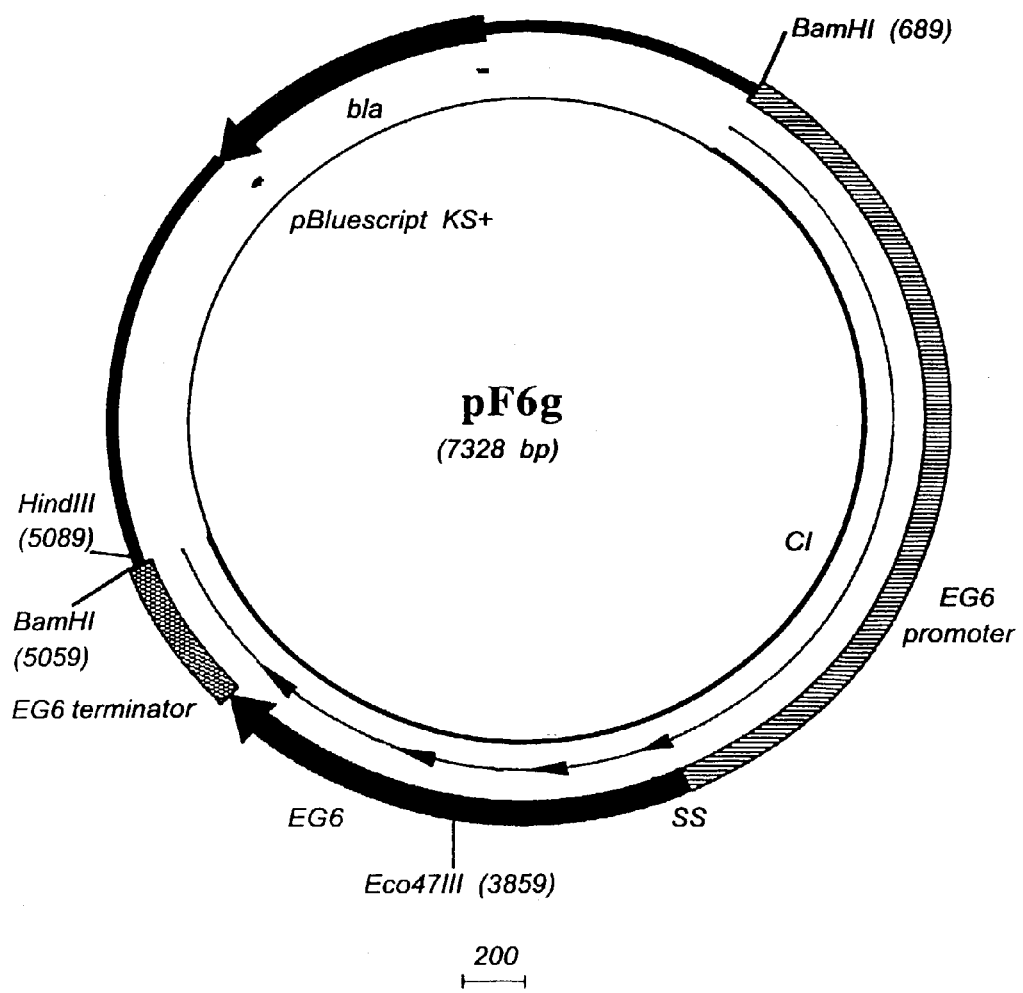
FIG. 6 is a pF6g map
Figure 7:
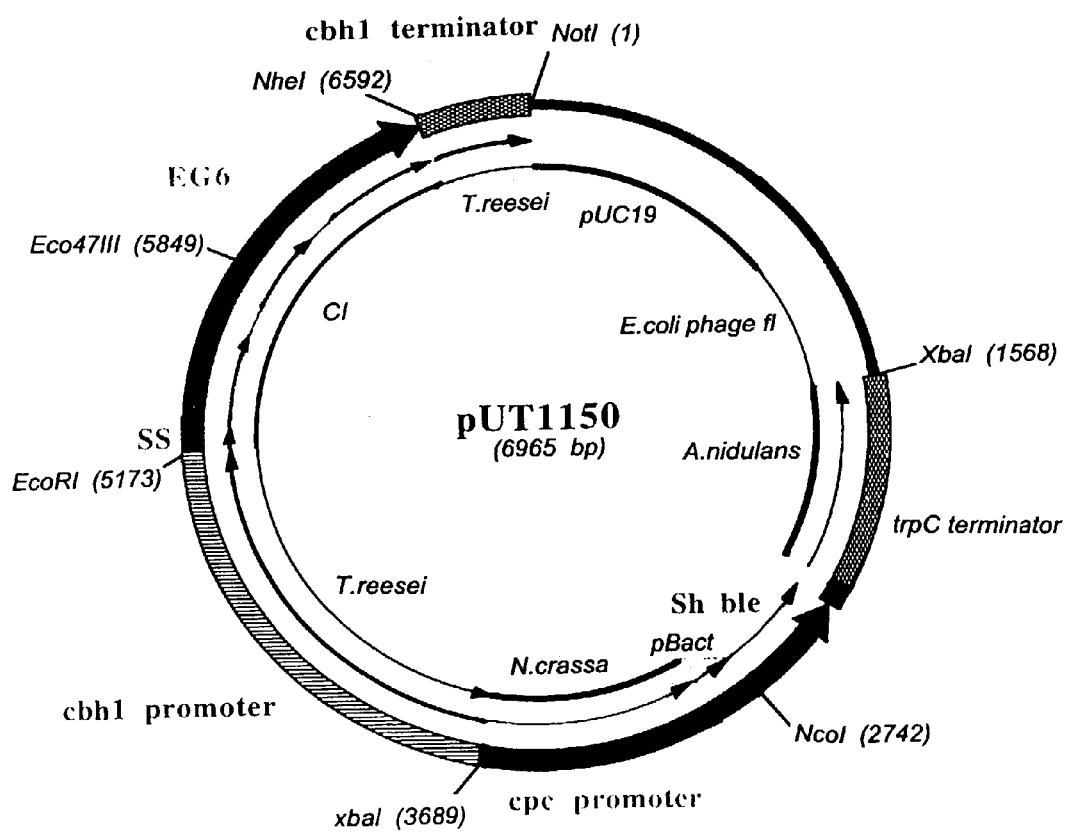
FIG. 7 is a pUT1150 map
Figure 8:
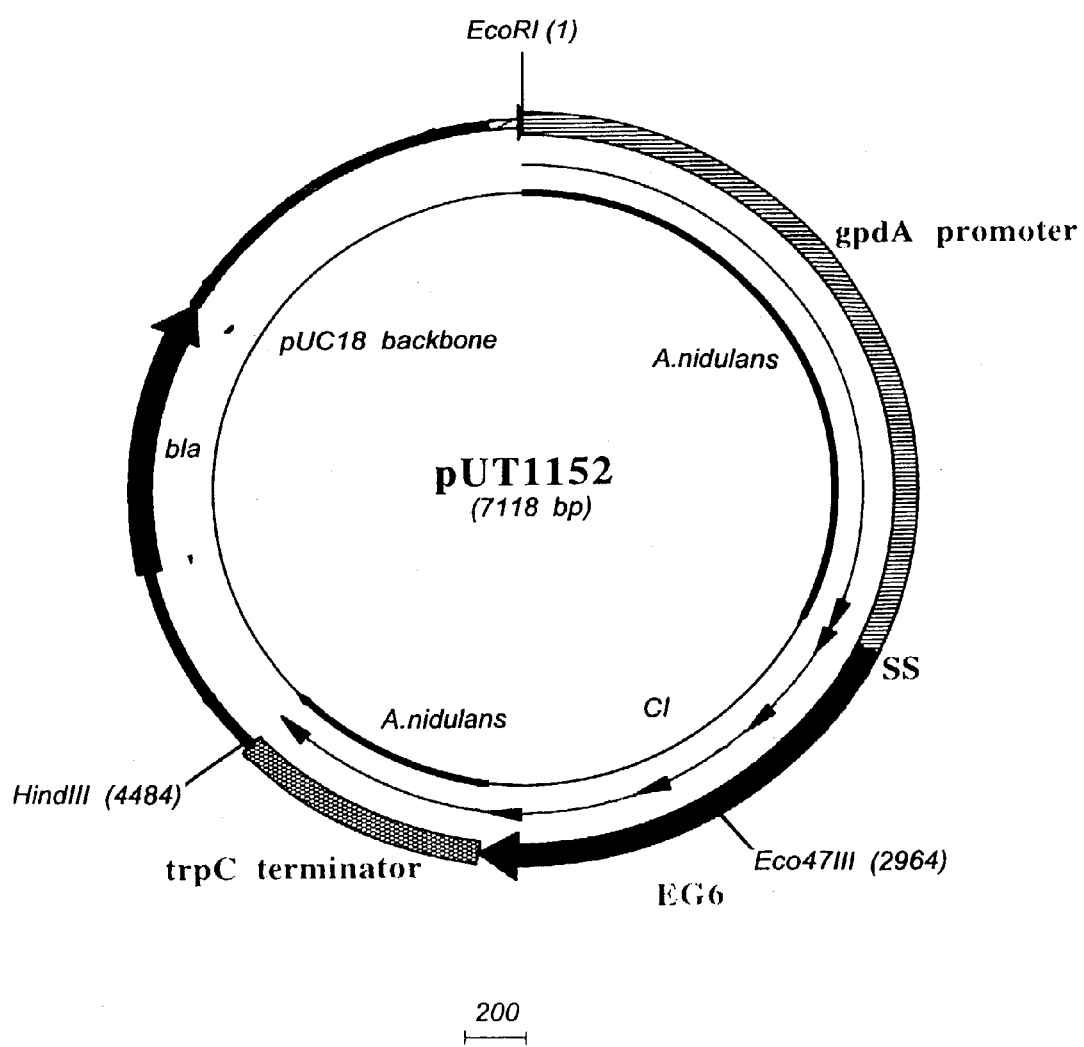
FIG. 8 is a pUT1152 map
Figure 9:
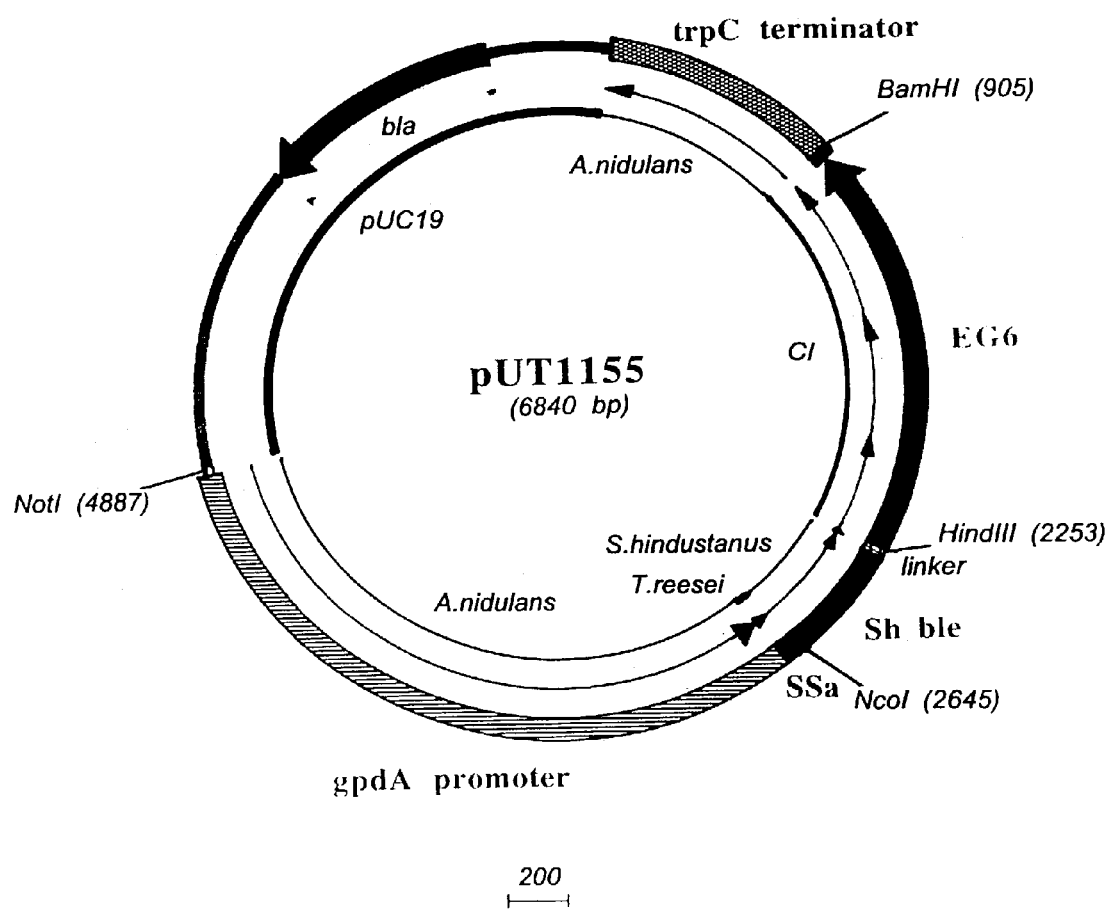
FIG. 9 is a pUT1155 map
Figure 10:
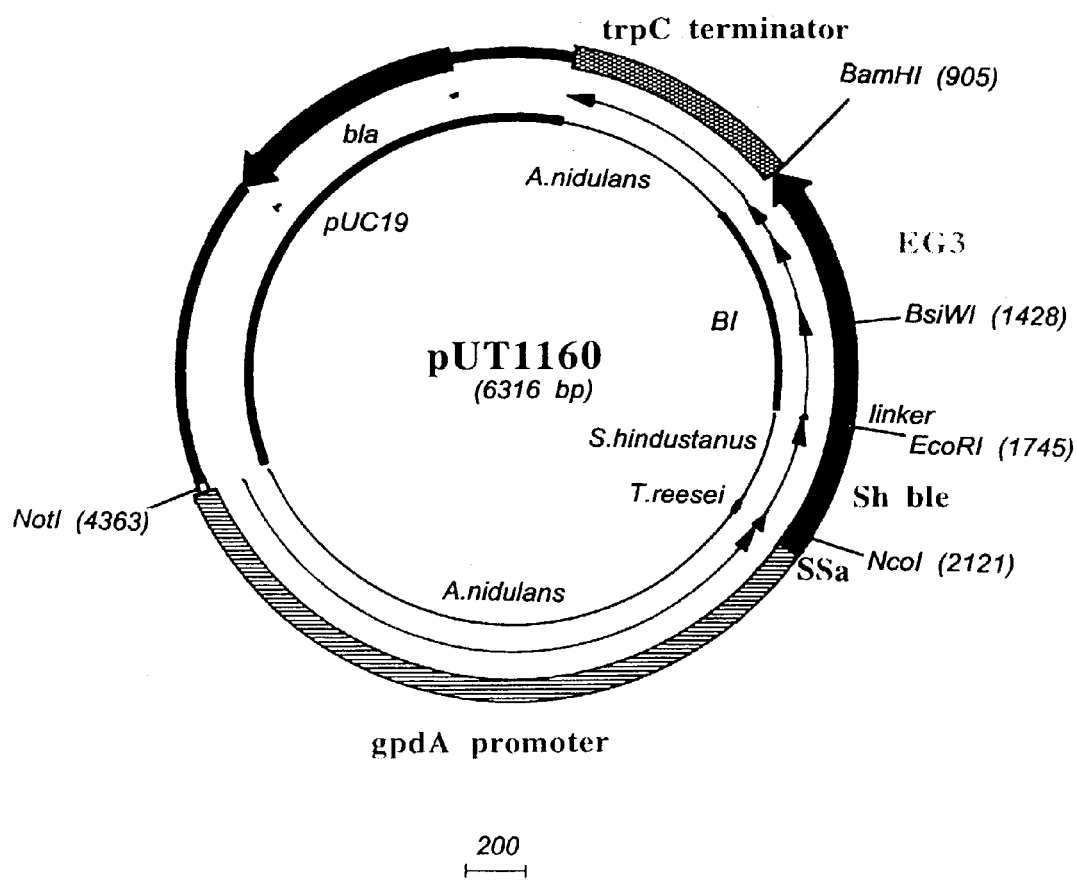
FIG. 10 is a pUT1160 map
Figure 11:
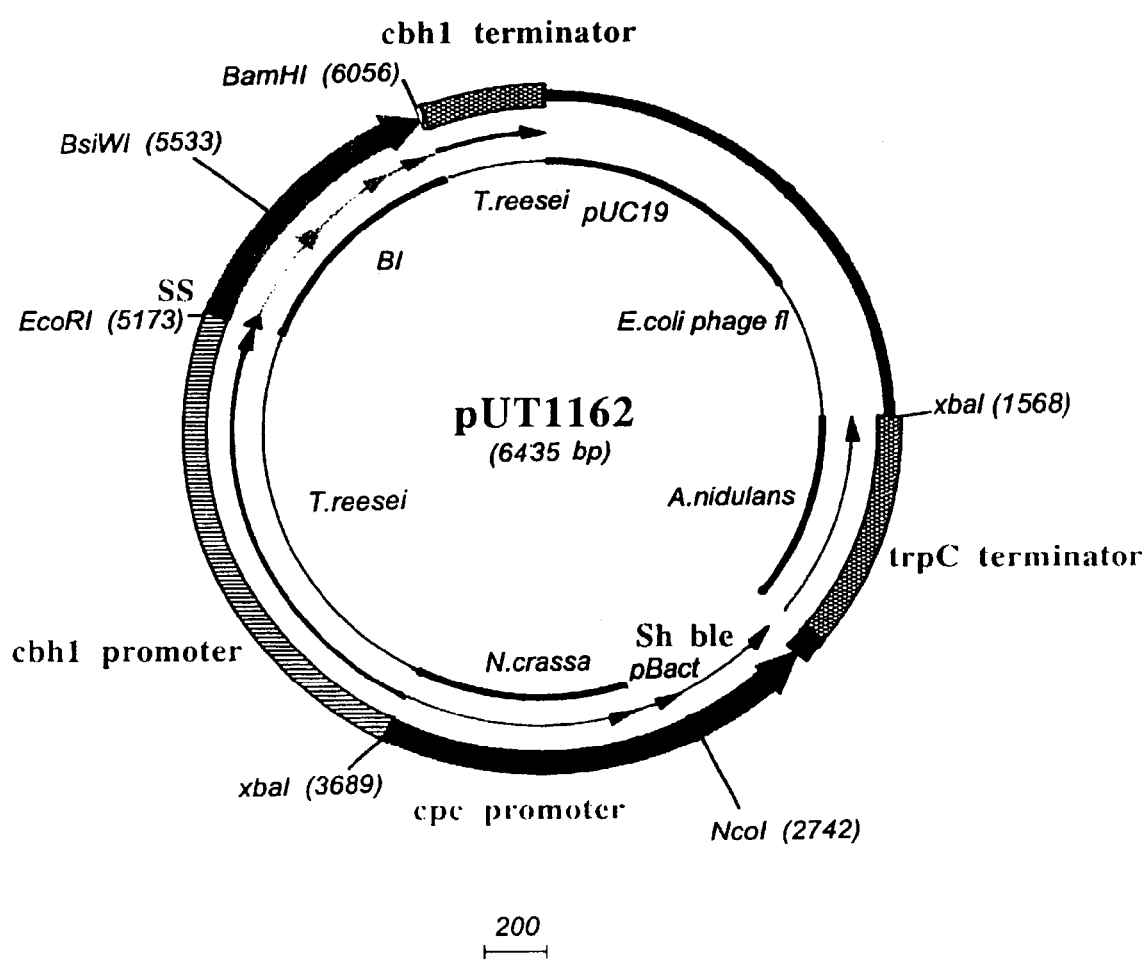
FIG. 11 is a pUT1162 map
Figure 14A:
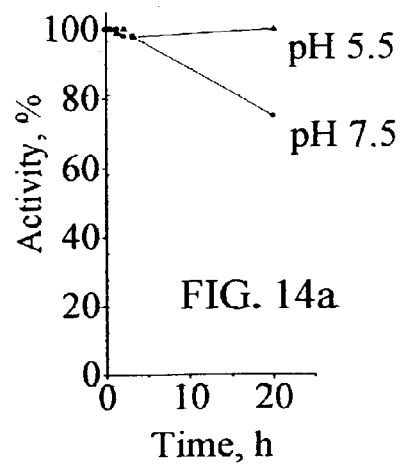
FIG. 14: Stability of enzymes from non-bound fraction of F-60-31 CF sample at pH 5.5 and 7.5 (60° C.).
Figure 14B:
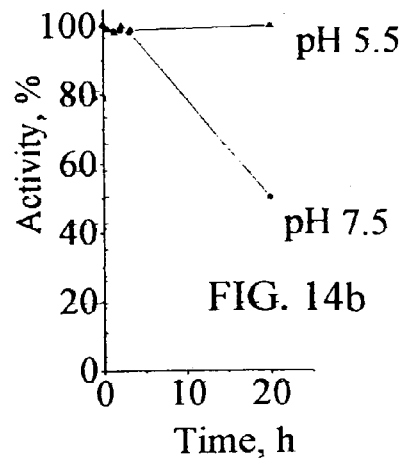
Figure 14C:
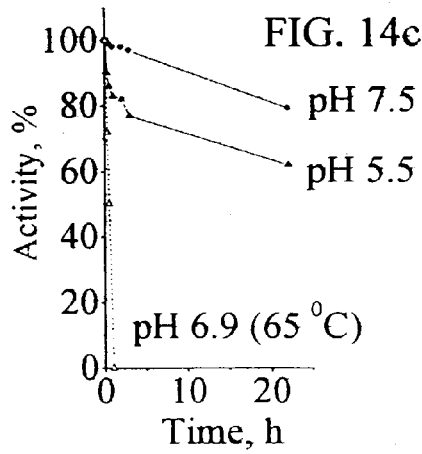
Figure 14D:
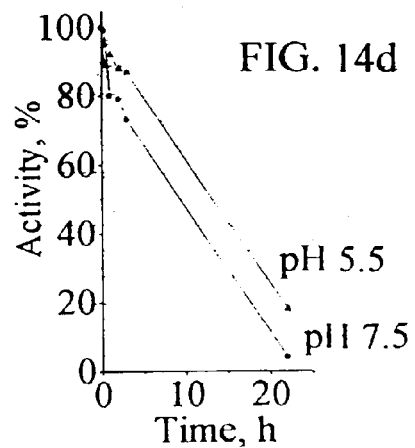
Figure 15A:
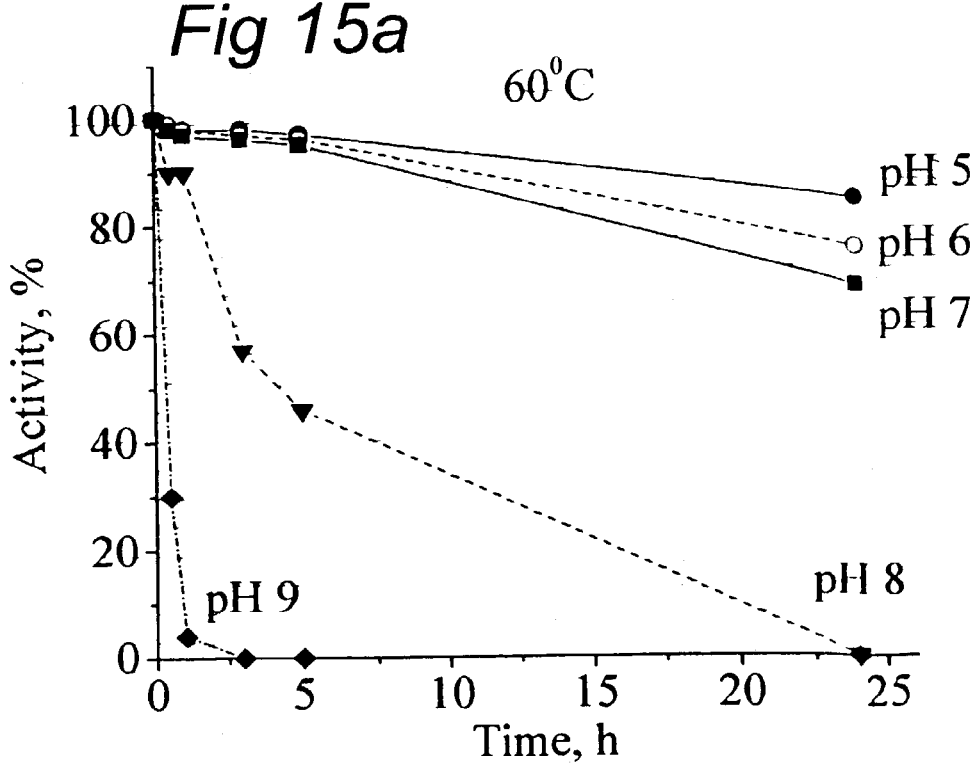
FIG. 15: pH stability at 60° C. and 50° C. of 60 kD Xyl (pI 4.7) from non-bound fraction of F-60-31 sample.
Figure 15B:
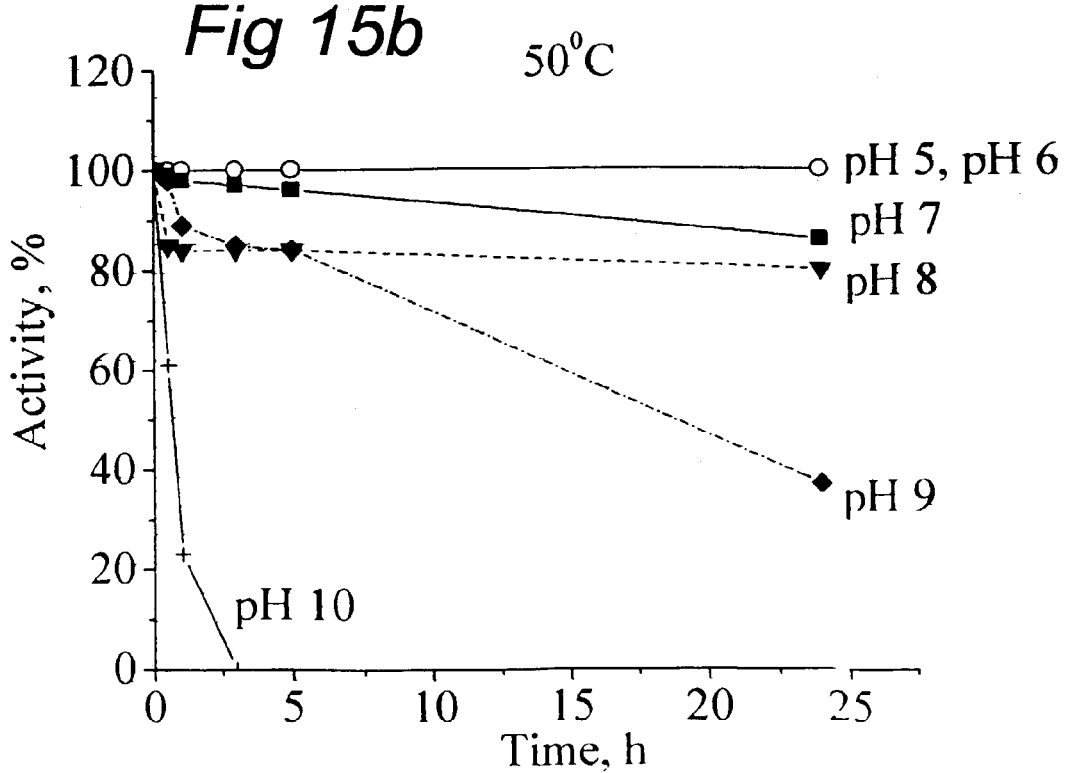
Figure 18A:
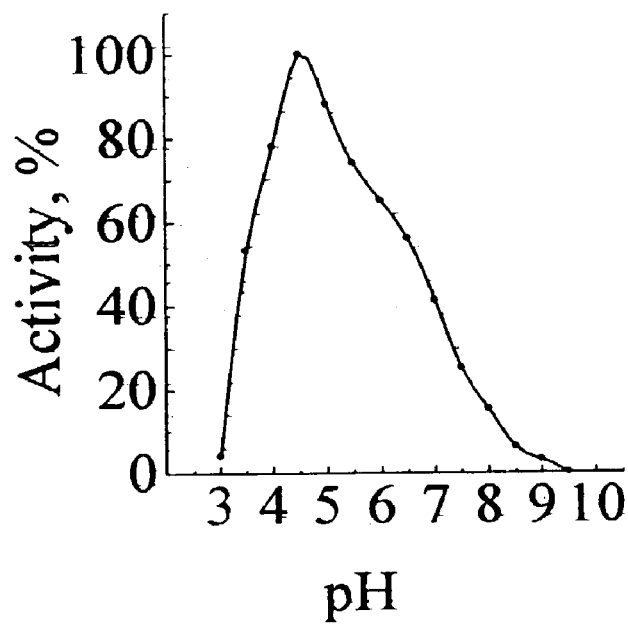
FIG. 18: pH and temperature dependencies of α-galactosidase activity of F-60-43, UF-conc.
Figure 18B:
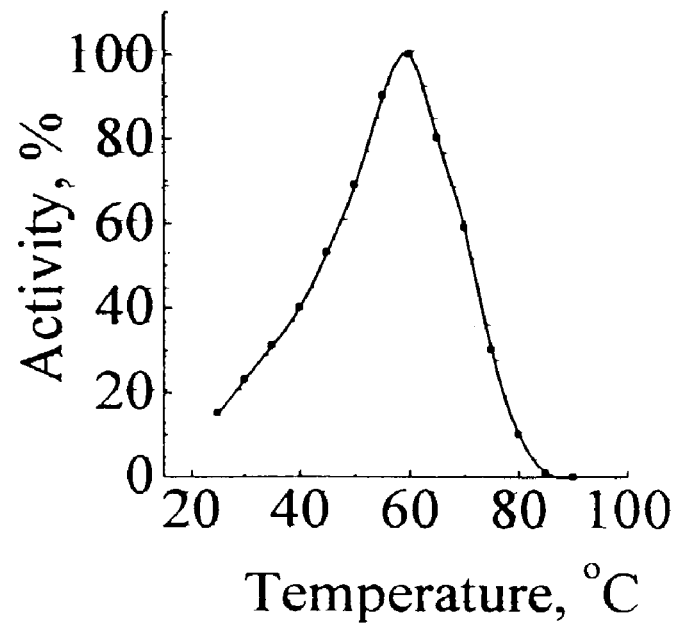
Figure 20:
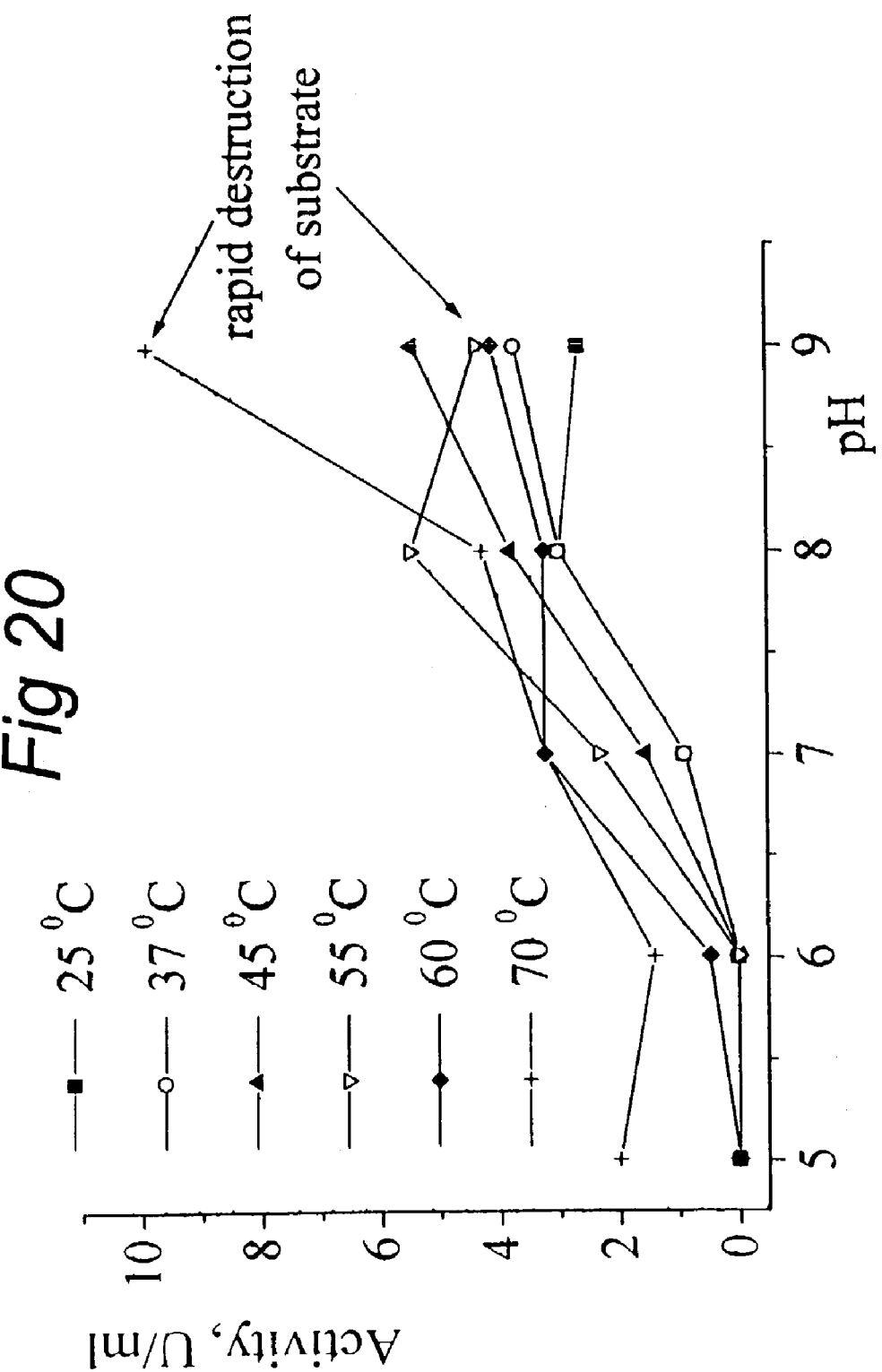
FIG. 20: Temperature dependencies of activity towards p-nitrophenyl butyrate of F-60-8 UF-conc.
Figure 21:
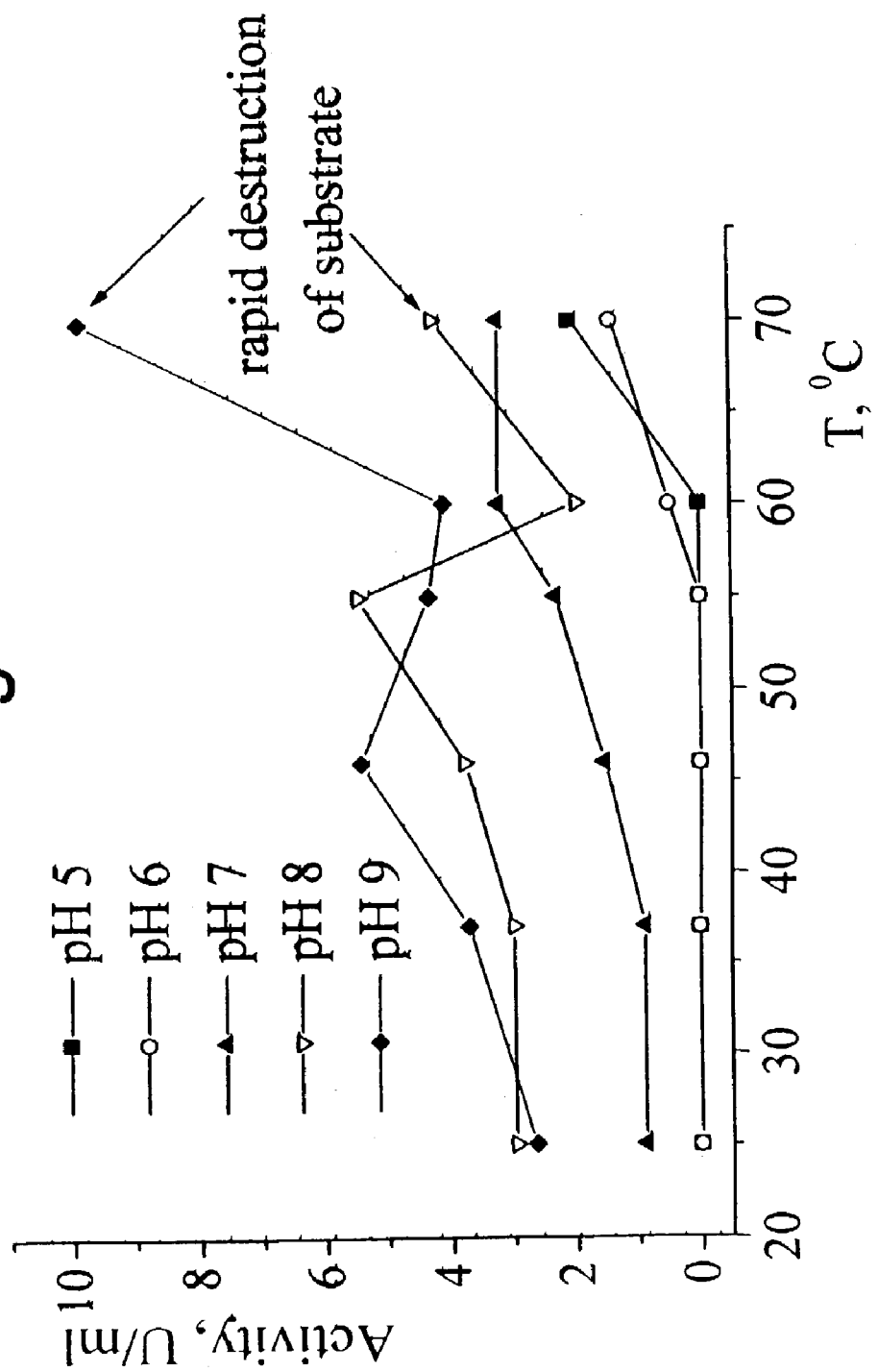
FIG. 21: pH dependencies of activity towards p-nitrophenyl butyrate of F-60-8 UF-conc.
Figure 23A:
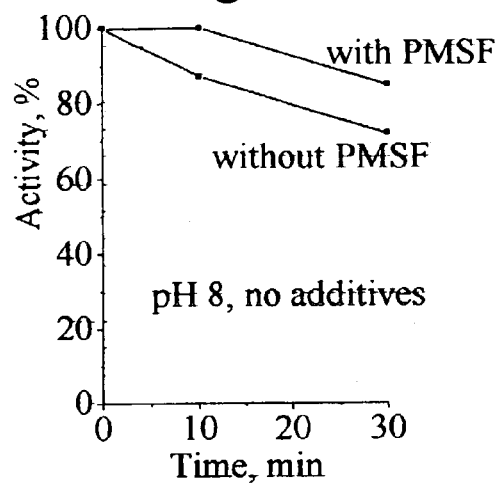
FIG. 23: Effect of 30 kD (pI 8.9) "alkaline" protease on xylanase activity of the non-bound-fraction (Macro Prep Q(™)) of F 60-31 CF at 50° C.
Figure 23B:
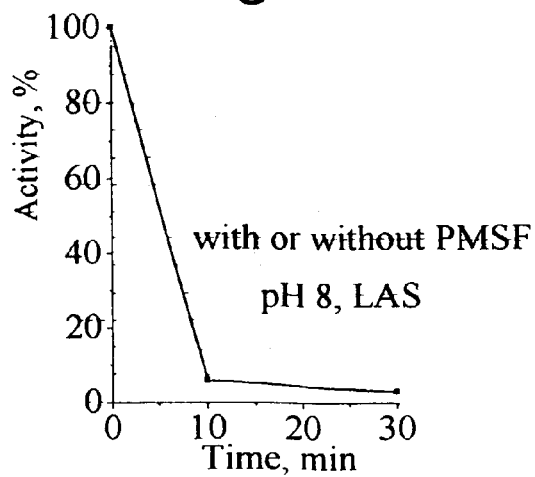
Figure 23C:
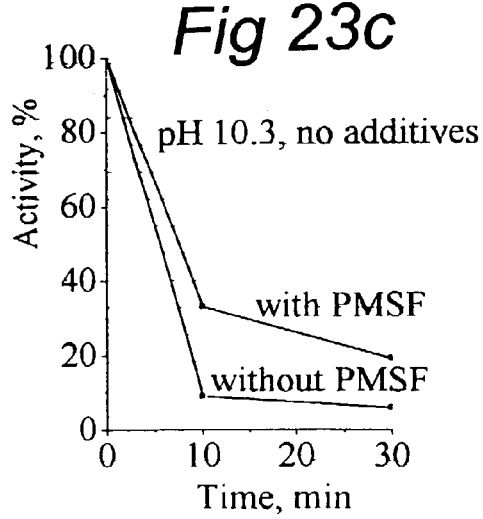
Figure 23D:
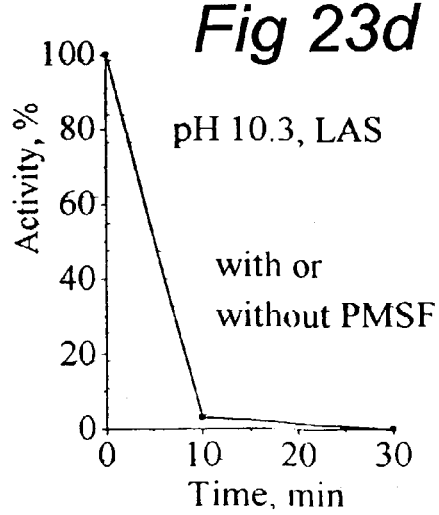
Figure 25:
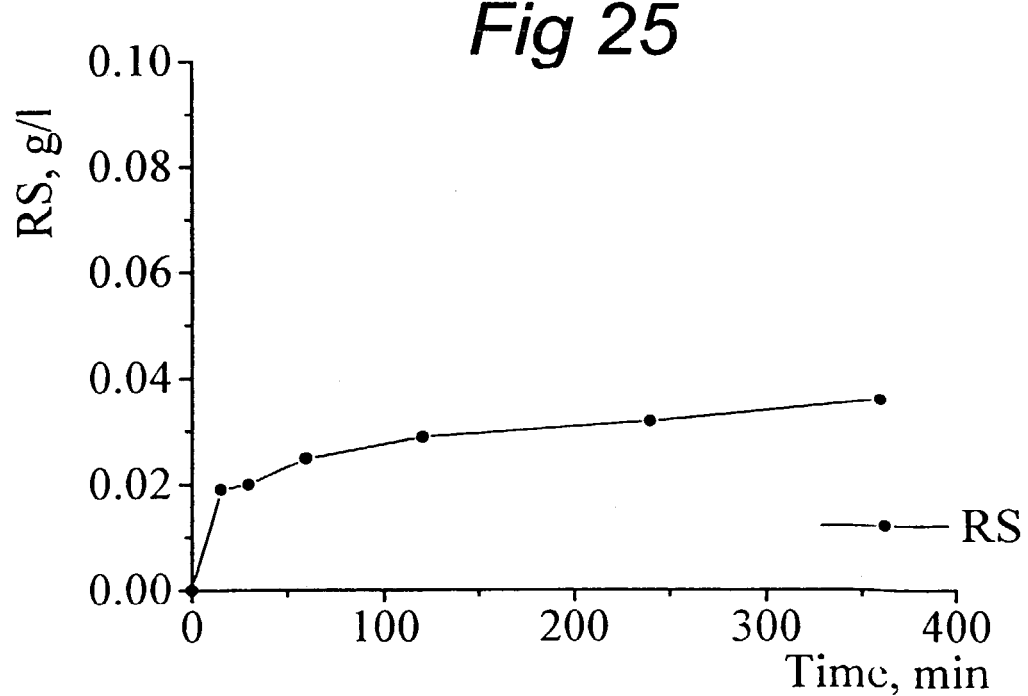
FIG. 25: Complete hydrolysis of polygalacturonic acid by 65 kD polygalacturonase (pI 4.4): 50° C., pH 4.5; concentration of PGA=5 g/l, concentration of protein=0.1 g/l.
Figure 29A:
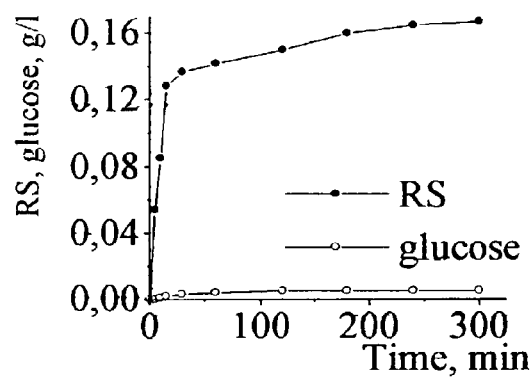
FIG. 29: Complete hydrolysis of CMC (a and c) and avicel (b and d) by the enzymes isolated from bound fractions of F-60-8 UF-conc. sample (50° C., pH 5): concentration of CMC and avicel=5 g/l, concentration of 25 kD Endo=0.01 g/l, concentration of 43 kD Endo=0.02 g/l; (a and b) 25 kD Endo (pI 4.1), (c and d) 43 kD Endo (pI 4.2).
Figure 29B:
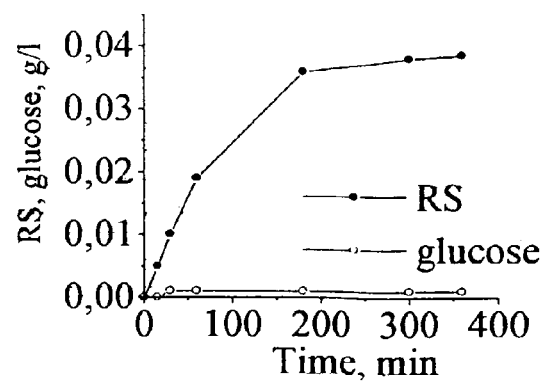
Figure 29C:
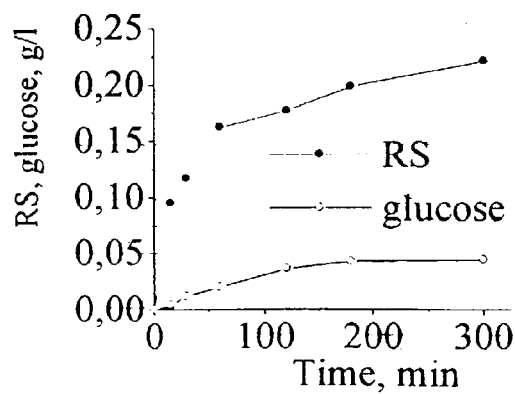
Figure 29D:
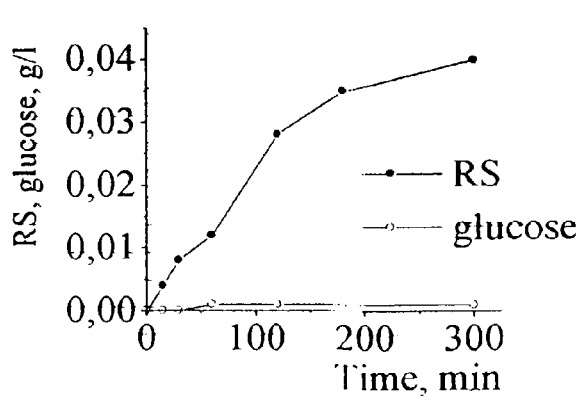
Figure 30B:
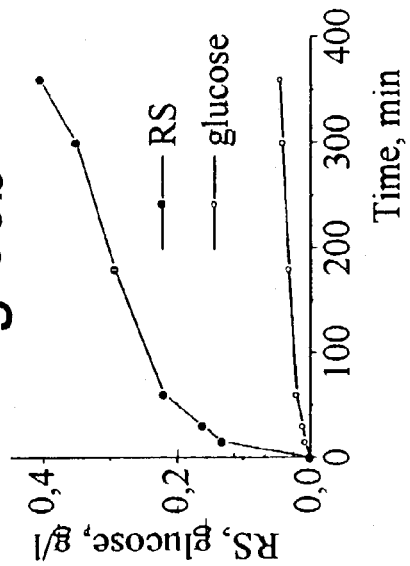
FIG. 30: Complete hydrolysis of CMC (a and b) and avicel (c and d) by 55 kD CBH (pI 4.4) without (a and c) and with (b and d) glucono- -lactone (50° C., pH 4.5): concentration of CMC and avicel=5 g/l, concentration of protein=0.1 g/l, concentration of glucono- -lactone=5 µl.
Figure 30D:
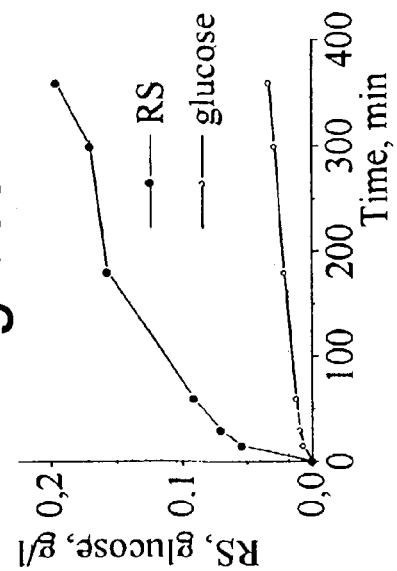
Figure 30A:
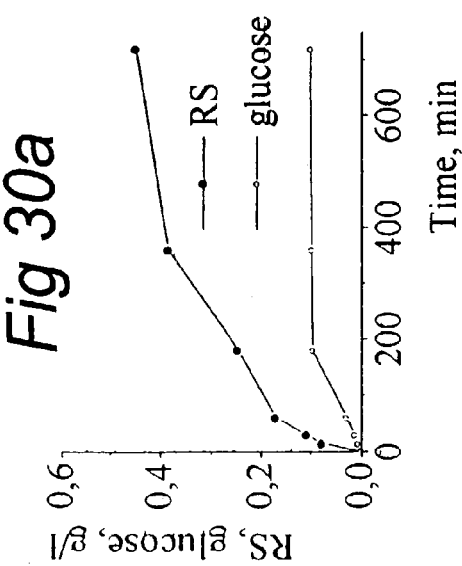
Figure 30C:
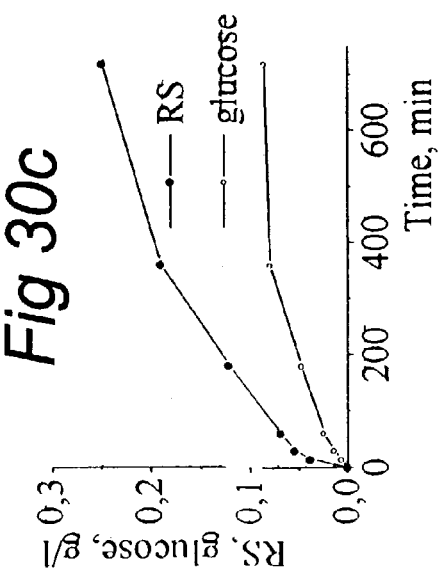
Figure 31A:
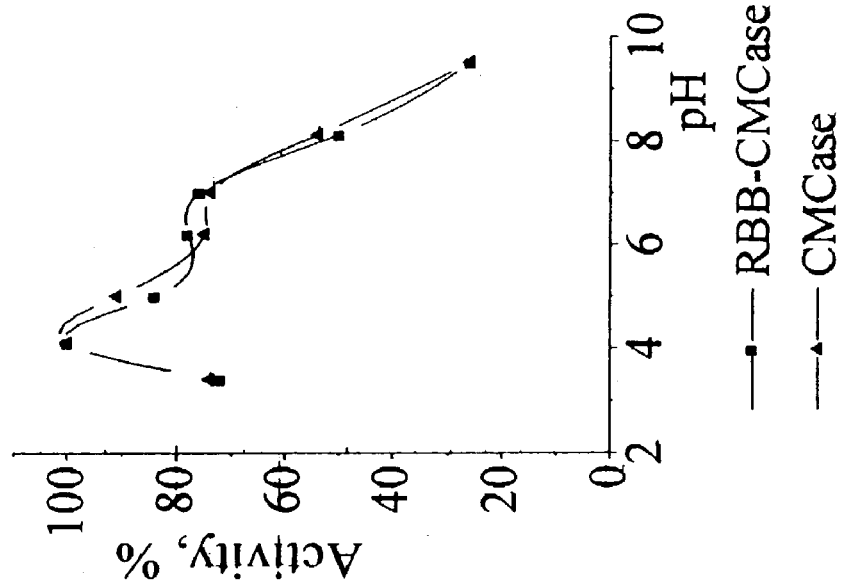
FIG. 31: pH-Dependence of CMCase and RBB-CMCase activities of the enzymes isolated from F-60-8 UF-conc. sample: (a) 25 kD Endo (pI 4.1), (b) 43 kD Endo (pI 4.2).
Figure 31B:
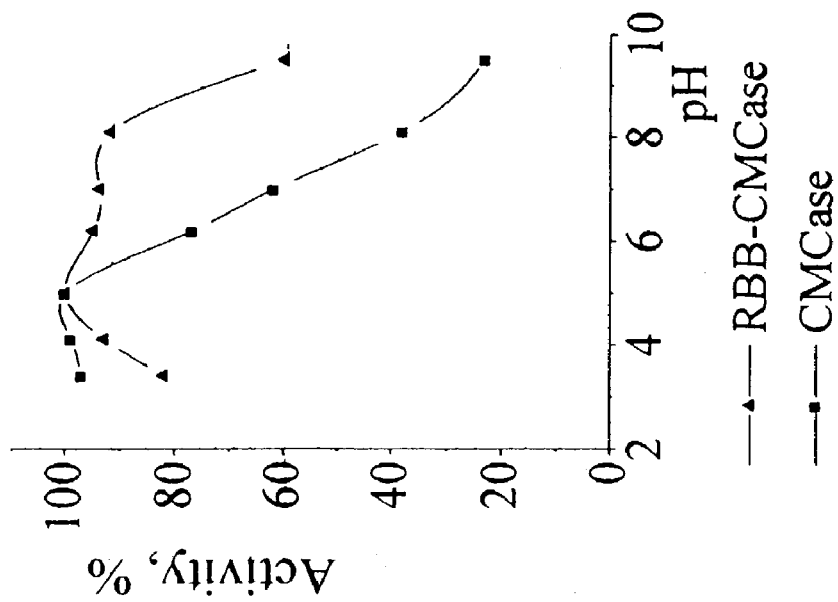
Figure 33A:
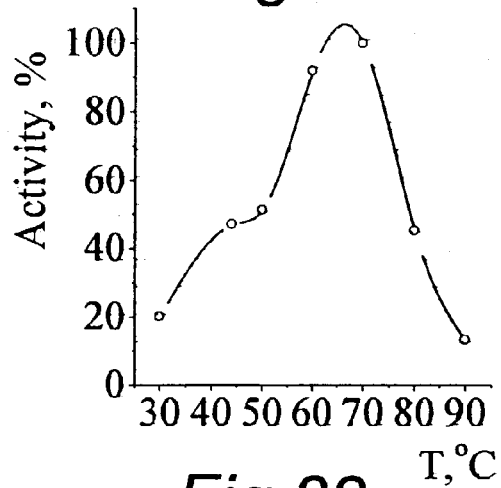
FIG. 33: Temperature dependencies of CMCase activity (pH 4.5) of the enzymes isolated from bound fractions of F-60-8 UF-conc. sample: (a) 55 kD CBH (pI 4.4), (b) 25 kD Endo (pI 4.1), (c) 43 kD Endo (pI 4.2).
Figure 33B:
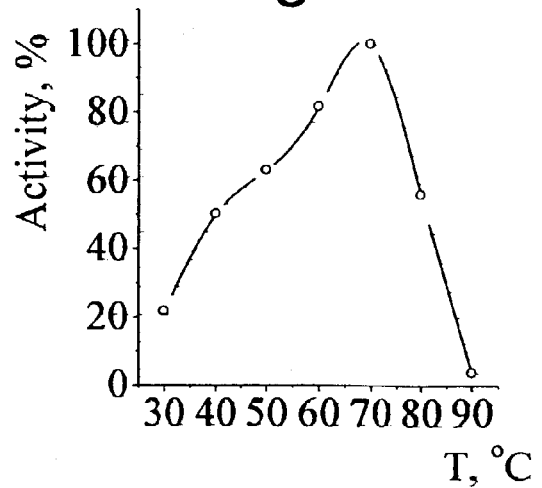
Figure 33C:
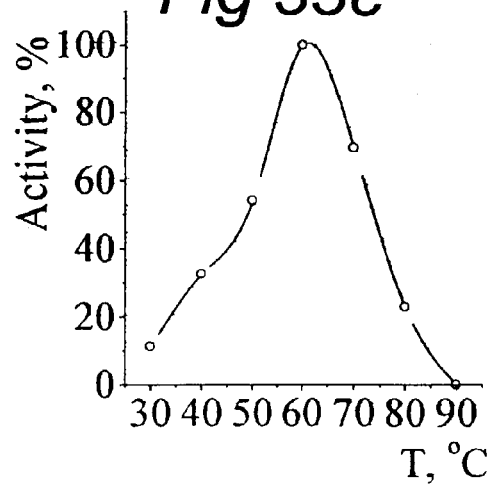
Figure 34A:
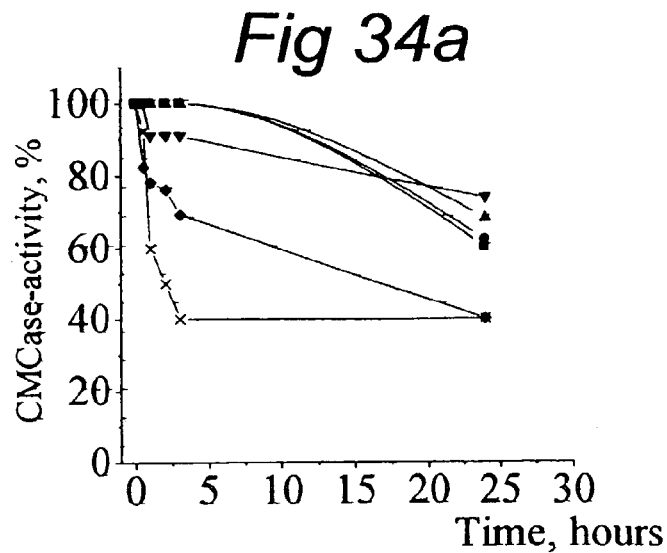
FIG. 34: pH-stability (50° C.) of the enzymes isolated from bound fractions of F-60-8 UF-conc. sample: (a) 55 kD CBH (pI 4.4), (b) 25 kD Endo (pI 4.1), (c) 43 kD Endo (pI 4.2).
Figure 34B:
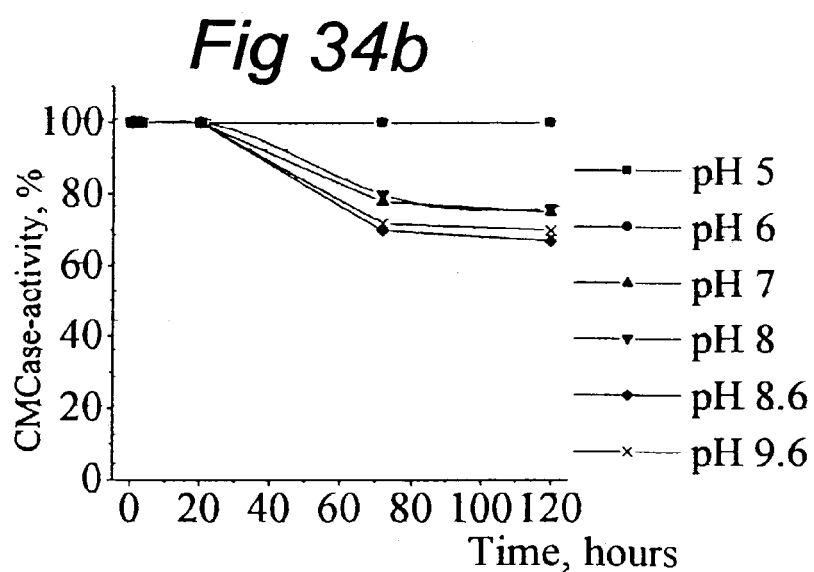
Figure 34C:
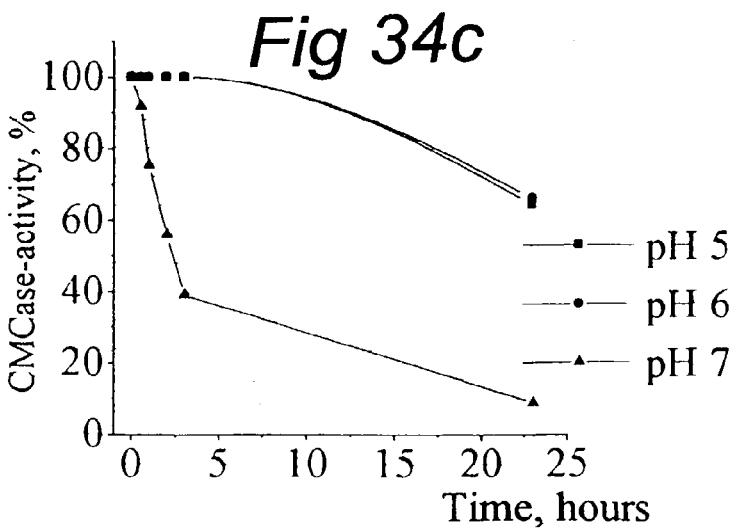

The vector also carries the beta-lactamase gene (bla) and an *E. coli* replication origin from plasmid pUC18[6]. The plasmid detailed map is provided in FIG. 5.

C1 protoplasts were transformed with plasmid pUT1064 or pUT1065 following the same procedure already described in example 1. The fusion protein in plasmid pUT1065 (Sh ble::XYN2) is functional with respect to the phleomycin-resistance thus allowing easy selection of the C1 transformants. Moreover, the level of phleomycin resistance correlates roughly with the level of xyn2 expression. In pUT1064, xyn2 was cloned with its own signal sequence.

The xylanase production of C1 transformants (phleomycin-resistant clones) was analysed by xylanase-activity assay as follow: Primary transformants were toothpicked to GS+phleomycin (5 µg/ml) plates (resistance verification) and also on XYLAN plates (xylanase activity detection by clearing zone visualisation[17]). Plates were grown for 5 days at 32° C. Each validated clone was subcloned onto XYLAN plates. Two subclones per transformant were used to inoculate PDA plates in order to get spores for liquid culture initiation. The liquid cultures in IC+5 g/l KPhtalate were grown 5 days at 27° C. (shaking 180 rpm). Then, the cultures were centrifuged (5000 g, 10 min.). From these samples, xylanase activity was measured by DNS Technique according to Miller et al.[18]

TABLE H

Active XYN2 production levels in C1 (best producers)

|  | Active xylanase II concentration in culture media | Xylanase II specific activity in culture media |
|---|---|---|
| Untransformed UV 18-25 | 3.9 U./ml | 3.8 U./mg total prot. |
| UV18-25::1064 clone 7-1 | 4.7 U./ml | 4.7 U./mg total prot. |
| UV18-25::1064 clone 7-2 | 4.4 U./ml | 4.3 U./mg total prot. |
| UV18-25::1065 clone 1-1 | 29.7 U./ml | 25.6 U./mg total prot. |
| UV18-25::1065 clone 1-2 | 30.8 U./ml | 39.4 U./mg total prot. |

These data show that:

1) Points 1 to 4 from example 2 are confirmed.)

2) C1 can be used as host for the secretion of a heterologous fungal protein.

[4] We also illustrate data from expression of transformed UV18-25 wherein the table I shows the results for the plasmids with which transformation was carried out. The Table shows good expression levels for endoglucanase and cellobiohydrolase using heterologous expression regulating sequences and signal sequences but also with homologous expression regulating sequences and signal sequences. The details of the various plasmids can be derived elsewhere in the description and from the figures. The production occurs at alkaline pH at a temperature of 35° C.

TABLE I

Expression data of transformed UV18-25 strain

| Culture | Total proteins mg/ml | CMCase u/ml | CMCase u/mg | β-glucanase u/ml | β-glucanase u/mg | pH value |
|---|---|---|---|---|---|---|
| *UV 18-25 | 100% | 100% | 100% | 100% | 100% | 7.90 |
| 1150-23 | 94% | 105% | 111% | 140% | 149% | 7.90 |
| -30 | 96% | 105% | 110% | 145% | 151% | 8.10 |
| 1152-3 | 94% | 112% | 120% | 147% | 156% | 7.85 |
| -4 | 100% | 105% | 105% | 132% | 132% | 7.90 |
| 1160-2 | 69% | 81% | 118% | 90% | 131% | 7.90 |
| -4 | 73% | 72% | 98% | 83% | 114% | 8.35 |
| -1 | 92% | 95% | 103% | 120% | 130% | 8.45 |
| 1162-1 | 102% | 105% | 103% | 145% | 142% | 8.20 |
| -11 | 112% | 109% | 98% | 115% | 103% | 8.20 |
| F6g-20 | 104% | 102% | 98% | 130% | 125% | 7.90 |
| -25 | — | — | — | — | — | — |

Culture conditions (shake flask): 88 h, 35° C., 230 rpm
*all above figures are in relative % to parent UV 18-25 strain Appendix to the Examples: Media
Transformation Media:

| Mandels Base: | | MnP Medium: | | |
|---|---|---|---|---|
| KH$_2$PO$_4$ | 2.0 g/l | Mandels Base with | | |
| (NH$_4$)$_2$SO$_4$ | 1.4 g/l | Peptone 1 g/l | | |
| MgSO$_4$.7H$_2$O | 0.3 g/l | MES 2 g/l | | |
| CaCl$_2$ | 0.3 g/l | Sucrose 100 g/l | | |
| Oligoelements | 1.0 ml/l | Adjust pH to 5 | | |
| MnR | | MnP CA$^{2+}$: | | |
| MnP + sucrose | 130 g/l | MnP Medium + | 50 mM | |
| Yeast extract | 2.5 g/l | CaCl$_2$ 2H$_2$O | | |
| Glucose | 2.5 g/l | Adjust pH to 6.5 | | |

-continued

| Agar | 15 g/l | |
| MnR Soft: | MnR with only 7.5 g/l of agar. | |
| MPC: | | |
| CaCl$_2$ | 50 mM | pH 5.8 |
| MOPS | 10 mM | |
| PEG | 40% | |

For Selection and Culture

| GS: | | |
|---|---|---|
| Glucose | 10 g/l | [Merieux] |
| Biosoyase | 5 g/l | pH should be 6.8 |
| Agar | 15 g/l | |
| PDA: | | |
| Potato Dextrose Agar | 39 g/l | [Difco] |
| | | pH should be 5.5 |
| MPG: | | |
| Mandels Base with | | |
| K. Phtalate | 5 g/l | |
| Glucose | 30 g/l | |
| Yeast extract | 5 g/l | |

The regeneration media (MnR) supplemented with 50 µg/ml phleomycin or 100-150 µg/ml hygromycin is used to select transformants. GS medium, supplemented with 5 µg/ml phleomycin is used to confirm antibiotic resistance.

PDA is a complete medium for fast growth and good sporulation. Liquid media are inoculated with 1/20th of spore suspension (all spores from one 90 mm PDA plate in 5 ml 0.1% Tween). Such cultures are grown at 27° C. in shake flasks (200 rpm).

Isolation and Characterisation of C1 Proteins

Figure 36:
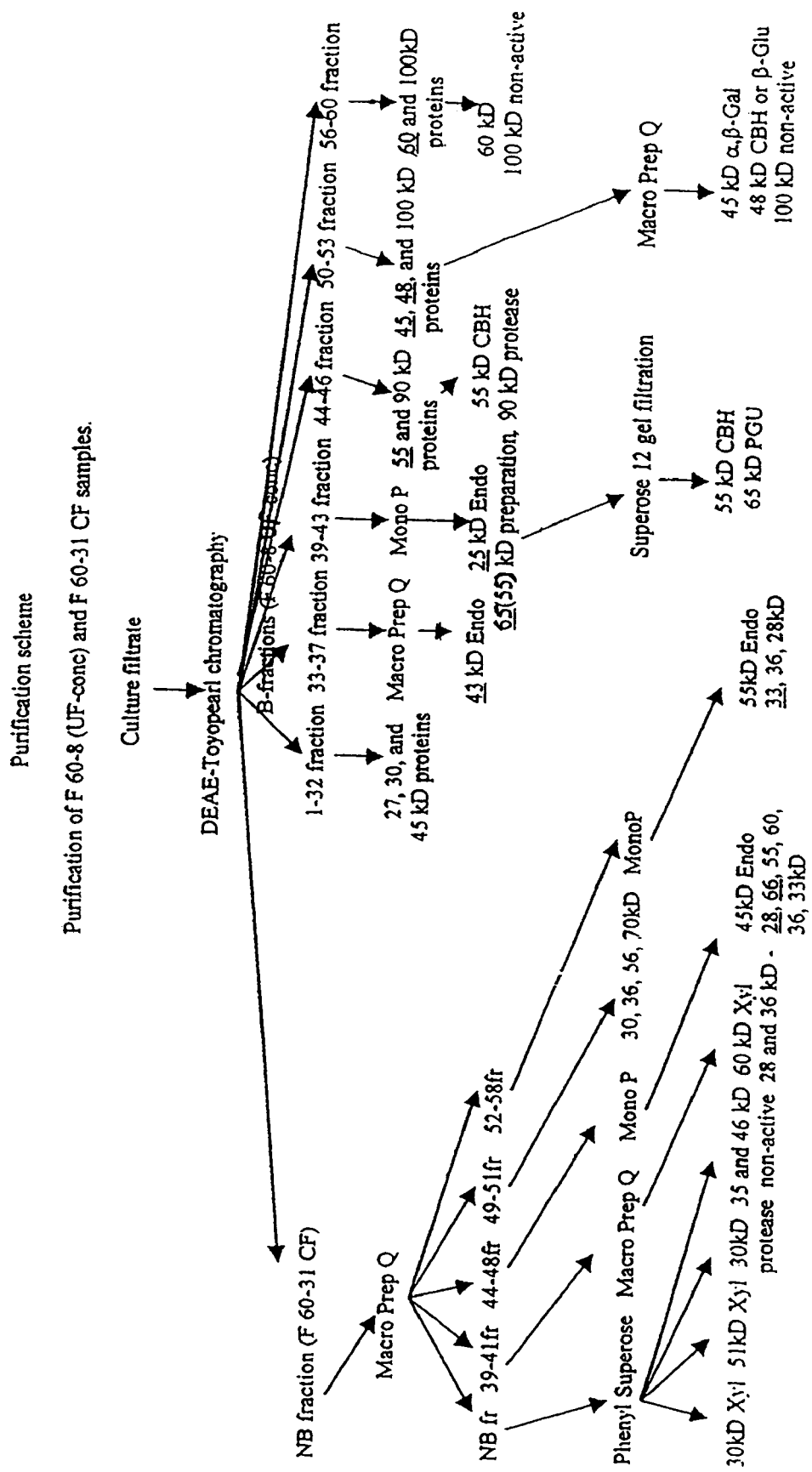
FIG. 36: Purification scheme of F-60-8 (UF-conc) and F-60-31 CF Samples for C1 Protein Isolation.

The process for obtaining various proteins is described as are a number of characteristics of the proteins. Tables A and B and FIG. 36 provide details of purification scheme and activities. Isolation occurs from the *Chrysosporium* culture filtrate using DEAE-Toyopearl ion exchange chromatography analogously to the method described in WO 98/15633, which is incorporated herein by reference. The non-bound fraction (F 60-31 CF) obtained from this chromatography was purified using Macro Prep Q (TM) ion exchange chromatography after equilibration to pH 7,6. The non-bound fraction (NB) was pooled and bound proteins were eluted in 0-1 M NaCl gradient. The NB fraction provided major protein bands of 19, 30, 35 and 46 kD and a minor one of 51 kD. In 0-1 M NaCl gradient protein peaks were eluted from various fractions. 39-41 included 28, 36 and 60 kD proteins, 44-48 included 28, 45 and 66 kD as major protein bands with 33, 36, 55, 60 and 67 kD proteins, the 49-51 fraction gave 30, 36, 56 and 68 kD proteins and the 52-59 fraction included major 33 and 55 kD proteins and minor 28 and 36 kD proteins. The pooled NB fraction was further purified by hydrophobic chromatography on Phenyl Superose (TM). The NB fraction was equilibrated with 0,03M Na-phosphate buffer pH 7,0 containing 1,2 M (NH4)2SO4 and applied to a column. Adsorbed proteins were eluted in 1,2-0,6 M (NH4)$_2$SO4 gradient. Thus homogeneous xylanase with MW 30 and 51 kD and pI 9.1 and 8.7 respectively were obtained as was a 30 kD protease with pI 8,9.

The xylanases did not possess MUF cellobiase activity and are thus true xylanases. The alkaline 30 kD xylanase (pI 9.1)

possessed high activity within a very broad pH range from 5-8 maintaining 65% of maximum activity at pH 9-10; it is a member of the xylanase F family; its partial nucleotide and amino acid sequences are depicted in SEQ ID No. 7. The partial amino acid sequence depicted corresponds to about amino acids 50-170 from the N terminus of the mature protein. Xylanases according to invention have at least 60%, preferably at least 70%, most preferably at least 80% sequence identity of the partial amino acid sequence of SEQ ID No. 7. The corresponding xylanase promoter, which is a preferred embodiment of the invention, can be identified using the partial nucleotide sequence of SEQ ID No. 7. The 51 kD xylanase (pI 8.7) possessed maximum activity at pH 6 and retained at least 70% of its activity at pH 7,5 and it retained at least 50% of its activity at pH 8.0. It was not very stable with only 15% activity at pH 5.5 and 4% at pH 7,5. The Michaelis constant toward birch xylan was 4.2 g/l for 30 kD xylanase and 3.4 g/l for 51 kD xylanase. Temperature optimum was high and equal to 70° C. for both xylanases.

The 30 kD protease activity measured towards proteins of the NB fraction appeared to be equal to $0,4 \times 10^{-3}$ units/ml at 50° C. and pH 7.90 kD. The fraction exhibited activity toward dyed casein of 0.4 arbitrary units/mg (pH 7). Addition of urea as chaotropic agent resulted in 2-3 times increase of protease activity. The effect of the protease on xylanase activity was significant. Only 30% xylanase activity remained at pH 10.3 and 50° C. after 30 minutes of incubation. At pH 8 95% of the xylanase activity remained. Linear alkylbenzene sulfonate (LAS) addition resulted in a dramatic decrease of xylanase activity at pH 8 and 10.3 with only 50% xylanase activity after 10 minutes of incubation with or without protease inhibitor PMSF. The 30 kD protease was alkaline with pH optimum at pH 10-11. The activity is inhibited by phenylmethylsulfonyl fluoride (PMSF) and not by iodoacetic acid, pepstatin A and EDTA which characterises it as a serine type protease. The protease is not active towards C1 proteins at neutral pH and 50° C. without chaotropic agents. Increase of pH and the addition of chaotropic agents such as LAS, SDS and urea significantly increase proteolysis.

The 39-41 fraction was purified by hydrophobic chromatography on phenyl superose. Fractions were equilibrated with 0.03M Na phosphate buffer pH 7.2 containing 1.5M (NH4)2SO4 and applied to a column. Adsorbed proteins were eluted in 1, 5-0 M (NH4)2SO4 gradient. Thus homogeneous xylanase with MW 60 kD and pI 4,7 was obtained. This xylanase possessed activities towards xylan, MUF-cellobioside, MUF-xyloside and MUF-lactoside. This xylanase probably belongs to family 10 (family F). This xylanase was stable at pH from 5 to 8 during 24 hours and retained more than 80% activity at 50° C. It retained 70% activity at pH 5-7 at 60° C. It kept 80% activity during 5 hours and 35% during 24 hours at 50° C. and pH 9. At pH 10 60% activity was retained at 50° C. and 0.5 hours of incubation. After 5 hours of incubation at pH 8 and 60° C. 45% activity was found decreasing to 0 after 24 hours. It had a pH optimum within the pH range of 6-7 and kept 70% activity at pH 9 and 50% of its activity at pH 9,5. The Michaelis constant toward birch xylan was 0,5 g/l. Temperature optimum was high and equal to 80° C.

Fraction 44-48 was then purified by chromatofocusing on Mono P. A pH gradient from 7.63-5.96 was used for the elution of the proteins. As a result 45 kD endoglucanase was isolated with a pI of 6. The 45 kD endo had maximum activity at pH 5 toward CMC and at pH 5-7 toward RBB-CMC. The 45 kD endo retained 70% of its maximal activity toward CMC at pH 6.5 and 70% of its maximal activity toward RBB-CMC was retained at pH 7.0; 50% of its maximal activity toward CMC was retained at pH 7 and 50% of its maximal activity toward RBB-CMC was retained at pH 8. The Michaelis constant toward CMC was 4.8 µl. Temperature optimum was high and equal to 80° C. Other proteins 28, 33, 36, 55, 60 and 66 kD were eluted mixed together.

Fraction 52-58 was purified by chromatofocusing on Mono P too with a pH gradient 7.6-4.5. Individual 55 kD endoglucanase with pI 4.9 was obtained. The 55 kD endo was neutral. It has a broad pH optimum from 4.5-6 and 70% activity was retained at pH 7.0 both for CMC and RBB-CMC and 50% activity was retained at pH 8 for both CMC and RBB-CMC. The Michaelis constant toward CMC was 1 g/l. Temperature optimum was high and equal to 80° C. A number of fractions also held proteins with MW of 28, 33 and 36 kD.

45, 48 and 100 kD proteins were isolated from bound DEAE Toyopearl fraction of F 60-8 UF conc of *Chrysosporium* culture from fractions 50-53 using Macro Prep Q chromatography.

Fraction 50-53 was equilibrated with 0.03 M imidazole HCL buffer, pH 5.75 and was applied to a column and the adsorbed proteins were eluted in 0,1-0,25 M NaCl gradient for 4 h. As a result 45 kD (pI 4.2), 48 kD (pI 4.4) and 100 kD (pI 4.5) proteins were isolated in homogenous states.

The 45 kD protein is supposedly an alpha, beta-galactosidase by virtue of its activity toward p-nitrophenyl alpha-galactoside and p-nitrophenyl beta-galactoside. The pH optimum was 4,5 70% activity was maintained at pH 5.7 and 50% of its activity was retained at pH 6.8. The temperature optimum was 60° C.

The 48 kD protein was a cellobiohydrolase having high activity toward p-nitrophenyl beta-glucoside and also activities toward MUF cellobioside, MUF lactoside and p-nitrophenyl butyrate. The 48 kD protein had a pH optimum of 5 toward CMC and 5-6 toward RBB-CMC.

The 100 kD protein with pI 4.5 possessed activity only toward p-nitrophenyl butyrate. It is probably an esterase but is not a feruloyl esterase as it had no activity against the methyl ester of ferulic acid. It had neutral/alkaline pH optimum (pH 8-9) and optimal temperature of 55-60° C.

The 90 kD protease with pI 4,2 was isolated from the bound fraction and the activity measured towards proteins of the NB fraction appeared to be equal to $12 \times 10^{-3}$ units/ml at 50° C. and pH 7.90 kD. The fraction exhibited activity toward dyed casein of 0.01 arbitrary units/mg (pH 7). Addition of urea as chaotropic agent resulted in 2-3 fold increase of protease activity as did addition of LAS at both pH 7 and 9 (50° C.). The 90 kD protease was neutral with pH optimum at pH 8. The activity is inhibited by phenylmethylsulfonyl fluoride (PMSF) and not by iodoacetic acid, pepstatin A and EDTA which characterises it as a serine type protease.

Also isolated from the bound fraction were 43 kD endoglucanase with pI 4.2 (fraction 33-37) and 25 kD endoglucanase with pI 4.1 (fraction 39-43), 55 kD cellobiohydrolase with pI 4.9 (fraction 39-43) and 65 kD polygalacturonase with pI 4.4 (fraction 39-43). The endoglucanases did not possess activity towards avicel or MUF cellobioside and possessed high activity toward MC, RBB-CMC, CMC41, beta-glucan and endoglucanase. The 25 kD endo did not produce glucose from CMC and the 43 kD endo did. No glucose was formed from avicel. The pH optimum for the 43 kD protein was 4,5 with 70% maximum activity maintained at pH 7.2 and 50% at pH 8. The 43 kD endo kept 70% activity at pH 5 and 6 during 25 hours of incubation. It kept only 10% at pH 7 during this incubation period. The 25 kD endo had pH optimum of activity at pH 5 toward CMC and broad pH optimum of activity toward RBB-CMC with 70% of the maximum activity being kept at pH 9 and with 50% of the maximum activity being at pH 10. It kept 100% activity at pH 5 and 6 and 80% at pH 7, 8, 8.6 and 9.6 during 120 hours of incubation. The 25 kD endo had a temperature optimum of activity at 70° C. The 43 kD endo had a temperature optimum of activity at 60° C. The Michaelis constants towards CMC were 62 and 12.7 g/l for 25 and 43 kD endo respectively. The polygalacturonase is a pectinase. The Michaelis constant toward PGA was 3.8 g/l. The pH optimum of PGU activity is within pH range 5-7 and T optimum within 50-65° C.

Genes encoding *C. lucknowense* proteins were obtained using PCR and characterised by sequence analysis. The corresponding full genes were obtained by screening (partial) gene libraries using the isolated PCR fragments. The full gene of the 43 kD endoglucanase (EG6, Family 6) of the C1 strain has been cloned, sequenced and analysed (including 2.5 kb promoter region and 0.5 kb terminator region). Its nucleotide and amino acid sequences are depicted in SEQ ID No. 6. Predicted molecular weight of the mature protein is 39,427 Da and predicted pI is 4.53, which values correspond well with the measured values. Protein alignment analysis with other glycosyl hydrolases of the family 6.2 shows that C1-EG6 does not include a cellulose-binding domain (CBD) Homology analysis using SwissProt SAMBA software (Smith & Waterman algorithm, Gap penalty 12/2, alignment 10, Blosum62 matrix) shows that C1-EG6 has 51.6% identity with *Fusarium oxysporum* EG-B (over 376 amino acids), 51.0% identity with *Agaricus bisporus* CBH3 (over 353 amino acids), and 50.7% identity with *Trichoderma reesei* CBH2 (over 367 amino acids). The putative signal sequence runs Met 1 to Arg 28. The promoter contains several potential CreA binding sites, so it is very likely that this promoter would be subject to glucose repression in a fungal strain with working CreA regulation.

Similarly, the full gene of the 25 kD endoglucanase (EG5, Family 45) of the C1 strain has been cloned, sequenced and analysed (including 3.3 kb promoter region and 0.7 kb terminator region). The nucleotide and amino acid sequences are depicted in SEQ ID No. 5. Predicted molecular weight of the mature protein is 21,858 Da and predicted pI is 4.66, which values correspond well with the measured values. This is the smallest fungal endoglucanase known to date. Protein alignment analysis with other glycosyl hydrolases of the family 45 shows that C1-EG5 does not include a cellulose-binding domain (CBD), nor a cohesin/dockerin domain. Homology analysis using NCBI-BLASTP2 software (Gap penalty 11/1, alignment 10, Blosum62 matrix) shows that the closest homologous protein to C1-EG5 is *Fusarium oxysporum* EG-K with 63% identity. The putative signal sequence runs Met 1 to Ala 18. The promoter contains many potential CreA binding sites, so it is very likely that this promoter would be subject to glucose repression in a fungal strain with working CreA regulation.

Furthermore, an additional endoglucanase was found by PCR based on family 12 cellulases homology analysis. The partial nucleotide and amino acid sequence of this additional endoglucanase (EG3, Family 12) is given in SEQ ID No. 8.

The 55 kD protein was a cellobiohydrolase (referred to herein as CBH1) with activity against MUF-cellobioside, MUF lactoside, filter paper and avicel, also against p-nitrophenyl -glucoside, cellobiose and p-nitrophenyl lactoside. Its activity toward MUF cellobioside is inhibited by cellobiose. The inhibition constant 0.4 mM was determined. The Michaelis constant toward MUF cellobioside was 0.14 mM, toward MUF lactoside was 4 mM and toward CMC was 3.6 g/l. The pH optimum is rather broad from 4.5 to 7.50% of maximum activity toward CMC and 80% activity toward RBB-CMC is kept at pH 8. 70-80% activity within pH 5-8 is kept during 25 hours of incubation. The temperature optimum is 60-70° C. CBH1 is probably a member of the cellobiohydrolase family 7; its partial nucleotide and amino acid sequences are depicted in SEQ ID No. 9. The partial amino acid sequence depicted corresponds to about amino acids 300-450 from the N terminus of the mature protein. A cellobiohydrolase according to the invention has at least 60%, preferably at least 70%, most preferably at least 80% sequence identity of the partial amino acid sequence of SEQ ID No. 9. The corresponding CBH promoter, which is a preferred embodiment of the invention, can be identified using the partial nucleotide sequence of SEQ ID No. 9. A synergistic effect was observed between 25 kD endo and 55 kD CBH during avicel hydrolysis. Synergism coefficient was maximal at the ratio of 25 kD endo to 55 kD CBH 80:20. The $K_{syn}$ was 1.3 at its maximum.

The expression level of five main *Chrysosporium* genes was studied by Northern analysis. Various strains of *C. lucknowense* were grown in rich medium containing Pharmamedia with cellulose and lactose (medium 1) or rich medium containing Pharmamedia and glucose (medium 2) at 33 C. After 48 h, mycelium was harvested and RNA was isolated. The RNA was hybridised with 5 different probes: EG5, EG6, EG3, XylF and CBH. After exposure, the Northern blots were stripped and hybridised again with a probe for ribosomal L3 as a control for the amount of mRNA on the blot. Most strains showed very high response for CBH and high response for XylF in medium 1; in medium 2, half of the strain showed high response for all genes, and the other half showed low response. The order of expression strength was deduced from these data as CBH>XylF>EG5>EG3>EG6.

Tables A and B and FIG. 36 illustrate the details of the above.

Advanced Isolation and Characterisation of C1 Genes and Gene Expression Sequences of CBH1 XYL1 EG3 and GPD Construction of a BlueSTAR Gene Library of UV18-25

Chromosomal DNA of UV 18-25 was partially digested with Sau3A, fragments of 12-15 kb were isolated and ligated in a BamHI site of cloning vector BlueSTAR. Packaging of 20% of the ligation mixture resulted in a gene library of $4.6 \times 10^4$ independent clones. This library was multiplied and stored at 4° C. and −80° C. The rest of the ligation mixture was also stored at 4° C.

Screening the Gene Library of UV18-25 for Isolation of the Genes for cbh1, eg3, xyl1 and gpd1

For the isolation of the different genes, in total $\pm 7.5 \times 10^4$ individual BlueSTAR phages per probe were hybridized in duplicate. Hybridisation was carried out with the PCR fragments of cbh1, eg3 and xyl1 (as described in PCT/NL99/00618) at homologous conditions (65° C.; 0.2×SSC) and with the gpd1 gene of *A. niger* at heterologous conditions (53° C.; 0.5×SSC). The number of positive signals is given in Table K. The positive clones were rescreened and for each clone two individual phages were used for further experiments. DNA of the different clones was analysed by restriction analysis to determine the number of different clones isolated from each gene (results are given in Table K).

As for each of the 4 genes, 4-6 different clones were isolated, we conclude that the primary gene library ($\pm 4$–$5 \times 10^4$ clones) represents about 5× genome of UV18-25. From this result we conclude that the complete genome of UV 18-25 is represented in $9 \times 10^3$ clones. Based on an average genomic insert of 13 kb, this would indicate a genome size of ±120 Mb, which is 3 times the size of the *Aspergillus* genome.

PCR reactions with specific primers for the gene present on the plasmid (based on previous sequence determination from the isolated PCR fragments) and the T7 and T3 primer present in the polylinker of pBlueSTAR we were able to determine the location of the genes in a number of clones. From each gene a plasmid was used for sequence determination of the gene.

Sequence Analysis of the Cloned Genes

For the cbh1, xyl1, eg3 and the gpd1 gene, the results of the sequence determination are represented in SEQ ID No's 1, 2, 3 and 4 respectively. Also the deduced amino acid sequences of the proteins are represented in these SEQ ID No's 1-4. Some properties of the proteins are given in Table L. It should be mentioned that the position of the start of the translation and the introns is based on homology with genes from the same family (i.e. paper genetics).

CBH1

From the amino acid sequences of CBH1, we concluded that the protein is about 63 kD in size and that a cellulose binding domain (CBD) is present at the C-terminal part of the protein. Interestingly, no evidence was found for the presence of a CBD in the isolated 55 kD major protein. However, the presence of the isolated peptides from this 55 kD major protein in the encoded CBH1 protein (SEQ ID No.1), confirms that the 55 kD protein is encoded by the cloned gene. A possible explanation of these results is that the 55 kD protein is a truncated version of the CBH1 protein lacking the CBD.

Xyl1

From the amino acid sequences of xyl1 we conclude that also here a CBD is present, in this protein at the N-terminal side. In the literature only two more xylanases with a CBD are known (*Fusarium oxysporum* and *Neocallimastix patriciarum*). The estimated size of the Xyl1 protein is 43 kD and several peptides isolated from a 30 kD xylanase originate from this protein (SEQ ID No. 2). It should be noted that a considerable number of the isolated peptides could not be found in the encoded sequence. This could indicate that alternative xylanase proteins are present in UV18-25. In previous analysis, no evidence was found for the presence of CBD in this 30 kD protein. Also from these results we hypothesized that the CBD of the protein is cleaved of by proteolysis. This hypothesis will be analysed further (by determination of activities, N-terminal sequences and sizes of the different proteins in the different C1 strains: C1 wild type, NG7C, UV13-6, UV18-25 and protease mutants of UV18-25) Also the effect of the presence or absence of the CBD on enzymatic activities has to be analysed in detail further. Overexpression of the full length genes in various C1 hosts may be considered. The presence of a cellulose binding domain (CBD) is a particular feature of this enzyme; the only other known family 10 glycolytic enzyme (xylanase) having a CBD is the *Fusarium oxysporum* XylF. The invention thus pertains to fungal xylanases having a CBD other than the *Fusarium oxysporum* xylanase.

EG3

From the amino acid sequence of EG3 it could be concluded that EG3 is a family 12 protein. The gene encodes a preproprotein with a dibasic (K-R) propeptide processing site. The C1EG3 protein is 62% similar and 54% identical to the B1 EG3 protein. One putative glycosylation site is present at the C-terminal part of the protein (SEQ ID No. 3).

Gpd1

The DNA sequence of the C-terminal part of the gpd1 gene is not determined, since we are primarily interested in the promoter sequences of this gene (SEQ ID No. 4).

The proteins XYL1 and EG3 of *C. lucknowense* are 54-70% identical to their closest homologue in the Genbank DATABASE (Table L). Notable is the strong homology of the CBH1 and the EG5 proteins to their related *Humicola grisea* proteins (74-82% identical). Interestingly the closest related proteins to the EG6 protein are only 46-48% identical.

Also notable is that in most cases the closest homologues originate from *Fusarium, Humicola* or other Pyrenomycetous fungi (Table L), whereas *Chrysosporium* belongs to the Plectomycetous fingi according to the NCBI taxonomy database (Table L).

TABLE K

Screening of 7.5 × 10$^4$ phages of the gene library of UV18-25 with PCR fragments of UV 18-25 for the cbh1 gene, the eg3 gene and the xyl1 gene (homologous conditions) and with the gpdA gene of *A. niger* (heterologous conditions). DNA isolation and restriction analysis was used to determine the number of different clones.

| Gene | Positive in first screening | positive in rescreening | different clones | clone used for sequencing |
|---|---|---|---|---|
| cbh1 | 8 | 7 | 4 | pCBH7 |
| eg3 | 6 | 6 | 4 | pEG3-3 |
| xyl1 | 9 | 6 | 5 | pXyl5 |
| gpd1 | 12 | 12 | 6 | pGPD4 |

TABLE L

| | glycosidase family | isolated from C1 | number of amino acids | introns | remarks | related sequences (% identity/% homology) |
|---|---|---|---|---|---|---|
| CBH1 | 7 | 70 kD 55 kD | 526 (63 kD) | 1 | CBD | *Humicola grisea* (74/82) (CBH1: P15828) *Fusarium oxysporum* (58/68) (CBH: P46238) *Neurospora crassa* (60/69) (CBH1: P38676) |
| XYL1 | 10 | 30 kD | 333 (43 kD) | 3 | CBD | *Fusarium oxysporum* (67/72) (XylF: P46239) *Penicillium simplissicum* (63/72) (XylF: P56588) *Aspergillus aculeatus* (61/70) (XylF: O59859) |
| EG3 | 12 | — | 247 (30 kD + glycos) | 2 | prepro peptide | *Aspergillus aculeatus* (60/71) (F1-CMCase: P22669) *Hypocrea jecorina* (56/73) |

TABLE L-continued

| glycosidase family | isolated from C1 | number of amino acids | introns | remarks | related sequences (% identity/% homology) |
|---|---|---|---|---|---|
| EG6 | 6(2) | 43 kD 395 | 2 | no CBD | (EG: BAA20140)<br>Aspergillus kawachii (54/69)<br>(CMCase: Q12679)<br>Fusarium oxysporum (48/59)<br>(EGLB: P46236)<br>Acremonium cellulolyticus (48/58)<br>(CBHII: BAA74458)<br>Agaricus bisporus (46/59)<br>(CBH3: P49075) |
| EG5 | 45 | 25 kD 225 | 3 | no CBD | Humicola grisea (82/91)<br>(EG: BAA74957)<br>Fusarium oxysporum (63/78)<br>(EGL-K: P45699)<br>Humicola grisea (62/78)<br>(EG: BAA74956) |
| GPD1 | — | — In-complete | 2+? | — | Podospora anserina (85/89)<br>(GPD: P32637)<br>Neurospora crassa 80/86)<br>(GPD: U67457)<br>Cryphonectria parasitica 80/85)<br>(GPD: P19089) |

REFERENCES

The Contents Hereof are Incorporated

1. Calmels T. P., Martin F., Durand H., and Tiraby G. (1991) *Proteolytic events in the processing of secreted proteins in fungi. J Biotechnol* 17(1): p. 51-66.
2. Punt P. J., Dingemanse M. A., Jacobs-Meijsing B. J., Pouwels P. H., and van den Hondel C. A. (1988) *Isolation and characterization of the glyceraldehyde-3-phosphate dehydrogenase gene of Aspergillus nidulans.* Gene 69(1): p. 49-57.
3. Shoemaker S., Schweickart V., Ladner M., Gelfand D., Kwok S., Myambo K., and Innis M. (1983) *Molecular cloning of exo-cellobiohydrolase I derived from Trichoderma reesei strain L27.* Bio/Technology Oct.:691-696.
4. Drocourt D., Calmels T., Reynes J. P., Baron M., and Tiraby G. (1990) *Cassettes of the Streptoalloteichus hindustanus ble gene for transformation of lower and higher eukaryotes to phleomycin resistance.* Nucleic Acids Res 18(13): p. 4009.
5. Mullaney E. J., Hamer J. E., Roberti K. A., Yelton M. M., and Timberlake W. E. (1985) *Primary structure of the trpC gene from Aspergillus nidulans.* Mol Gen Genet. 199(1): p. 37-45.
6. Yanisch-Perron C., Vieira J., and Messing J. (1987) *Improved M13 phage cloning vectors and host strains: nucleotide sequences of the M13 mp18 and pUC19 vectors.* Gene 33:103-119.
7. Durand H., Baron M., Calmels T., and Tiraby G. (1988) *Classical and molecular genetics applied to Trichoderma reesei for the selection of improved cellulolytic industrial strains,* in Biochemistry and genetics of cellulose degradation, J. P. Aubert, Editor. Academic Press. p. 135-151.
8. Lowry O. H., Rosebrough N. J., Farr A. L., and Randall R. J. (1951) *Protein measurements with the folin phenol reagent.* J. Biol. Chem. ?:193-265.
9. Parriche M., Bousson J. C., Baron M., and Tiraby G. *Development of heterologous protein secretion systems in filamentous fungi.* in 3rd European Conference on Fungal Genetics. 1996. Münster, Germany.
10. Baron M., Tiraby G., Calmels T., Parriche M., and Durand H. (1992) *Efficient secretion of human lysozyme fused to the Sh ble phleomycin resistance protein by the fungus Tolypocladium geodes.* J Biotechnol 24(3): p. 253-266.
11. Jeenes D. J., Marczinke B., MacKenzie D. A., and Archer D. B. (1993) *A truncated glucoamylase gene fusion for heterologous protein secretion from Aspergillus niger.* FEMS Microbiol. Lett. 107(2-3): p. 267-271.
12. Stone P. J., Makoff A. J., Parish J. H., and Radford A. (1993) *Cloning and sequence-analysis of the glucoamylase gene of neurospora-crassa.* Current Genetics 24(3): p. 205-211.
13. Mörsky P. (1983) *Turbidimetric determination of lysozyme with Micrococcus lysodeikticus cells: Reexamination of reaction conditions.* Analytical Biochem. 128: 77-85.
14. Paluh J. L., Orbach M. J., Legerton T. L., and Yanofsky C. (1988) *The cross-pathway control gene of Neurospora crassa, cpc-1, encodes a protein similar to GCN4 of yeast and the DNA-binding domain of the oncogene v-jun-encoded protein.* Proc Natl Acad Sci USA 85(11): p. 3728-32.
15. Nakari T., Onnela M. L., Ilmen M., Nevalainen K., and Penttilä M. (1994) *Fungal promoters active in the presence of glucose,* patent #WO 94/04673, Alko.
16. Torronen A., Mach R. L., Messner R., Gonzalez R., Kalkkinen N., Harkki A., and Kubicek C. P. (1992) *The two major xylanases from Trichoderma reesei: characterization of both enzymes and genes.* Biotechnology (N Y) 10(11): p. 1461-5.
17. Farkas V. (1985) *Novel media for detection of microbial producers of cellulase and xylanase.* FEMS Microbiol. Letters 28:137-140.
18. Miller G. L. (1959) *Use of dinitrosalicylic acid reagent for determination of reducing sugar.* Anal. Chem. 31:426-428.
19. Punt P. J., Mattern I. E., van den Hondel C. A. M. J. J. (1988) *A vector for Aspergillus transformation conferring phleomycin resistance.* Fungal Genetics Newsletter 35, 25-30.

SEQ ID No. 1:

DNA sequence and amino acid of complete *Chrysosporium* CBH1 gene including promoter and terminator sequences. Promoter, terminator and intron sequences are given in small case. The putative signal peptide is shown in italic letters and the cellulose binding domain (CBD) is shown in bold underlined letters.

```
aaggtatccgatttggggaacgtcgatgaaagtattgcaaaagtgacgagagttgcgcaa      60 ctaactcgctgccgaagaagctgcggaagaaagagaacaccgaaagtggaataacgttac     120 ggatgtcctgacctcaaagttgaaaccagcccttcctgctctatttgggaaagcggcttg     180 cccttgaatgcgctgcactgtggcacgactaccagtgatcgggaggagcaaactaccctg     240 gtccgttccttggtggggcggcactaggcccaacttagggtgatcggaggtcgatgccgc     300 ggtcctcgttggtctgggctcttctcatttcccggtttgcaccccccgttgcacctgctg     360 atcgcccgccaacgccgatgaggttgcgcccagaccgacaatcaccgcggctgcattccc     420 aagtatattgaagatggcaccaggtacccggttttgcgtcccagtcgtttggtgccaaat     480 ttgggagttttgagcctcaagatctggggaaatcgacctcaacttccatacaagttaaa     540 gtcgcacacacggcgagttccacgaagagacacattttttctgaaggcctctctcccg     600 cacatcagaaaccaccaaataccaagactgcagaagccggggtaagtgggccaccgggac     660 tacactaaaatgcggggagaagcgagatccgttgcgaagggaagggatggggtgtgctgc     720 ggctttctccgctctcgtgcgccttttgcttgaatctagtgtacaccagggtaggctccg     780 aaggagtatctacggcagcgctgttcgtgctgcgttgagagtcagggcggagacgagcag     840 gcgacaggagcctcgcaccggcacttcggatcgcatttgcgcggagcgtcaaatacgctc     900 ttctgcggtcatcagagagcatcgtgaaccaaggttcttccgcagggcggcctgggcttc     960 gcagagtcgcactcggcggacgccttccgtgtcacccctgataacctggctgccgcgccc    1020 agactcctccaatgaggtgtgtggttgccctcgccgaccccttcagcaaccttaatcgctt    1080 ccatcgcacggctccacgtcctcgaacgatgccctcagtccgtgcccggccgtggcaacc    1140 ataacgtgacatcgccgcccagcctactagccgctatcgaccggttaggcttgtcaccgc    1200 agcgcccattctccatcgggcctctactctgatccacctcacccaccgcaagcactagcg    1260 agcctcaccagagtgcaagcgacacgacccgcttggcccttcgtccttgactatctccca    1320 gacctcttgccatcttgccgacgccgcccccttttttttctcctcccccctgccggcaggt    1380 cggtggccccagtcccgagatggcattgctccgttgtccatgacgacccatcattcgatg    1440 gctgactggcacactcgtcttgtttgagcatcgacggcccgcggcccgtctcccacggta    1500 cggaacctcgttgtacagtacctctcgtaatgatacccaacaccggggccgagcgctggg    1560 agggcggcgttcccgagaagccgggaaggcggctggccggctgacctttgtgacttggcg    1620 atggatgcggccatggagaatgtccgtccgaagcgacgcgacaattagcctggctaccat    1680 cgatataaattgggtgattcccagctcttgatgggcgtgtcttctgcctggcagccctcg    1740 tcttcagatcaagcaactgtgtgctgatcctcttccgccATGTACGCCAAGTTCGCGACC    1800
                                         M  Y  A  K  F  A  T CTCGCCGCCCTTGTGGCTGGCGCCGCTGCTCAGAACGCCTGCACTCTGACCGCTGAGAAC    1860
 L  A  A  L  V  A  G  A  A  A  Q  N  A  C  T  L  T  A  E  N CACCCCTCGCTGACGTGGTCCAAGTGCACGTCTGGCGGCAGCTGCACCAGCGTCCAGGGT    1920
 H  P  S  L  T  W  S  K  C  T  S  G  G  S  C  T  S  V  Q  G TCCATCACCATCGACGCCAACTGGCGGTGGACTCACCGGACCGATAGCGCCACCAACTGC    1980
 S  I  T  I  D  A  N  W  R  W  T  H  R  T  D  S  A  T  N  C TACGAGGGCAACAAGTGGGATACTTCGTACTGCAGCGATGGTCCTTCTTGCGCCTCCAAG    2040
 Y  E  G  N  K  W  D  T  S  Y  C  S  D  G  P  S  C  A  S  K TGCTGCATCGACGGCGCTGACTACTCGAGCACCTATGGCATCACCACGAGCGGTAACTCC    2100
 C  C  I  D  G  A  D  Y  S  S  T  Y  G  I  T  T  S  G  N  S CTGAACCTCAAGTTCGTCACCAAGGGCCAGTACTCGACCAACATCGGCTCGCGTACCTAC    2160
 L  N  L  K  F  V  T  K  G  Q  Y  S  T  N  I  G  S  R  T  Y CTGATGGAGAGCGACACCAAGTACCAGAgtaagttcctctcgcacccggccgccgggaga    2220
 L  M  E  S  D  T  K  Y  Q
```

```
                           -continued
 L   M   E   S   D   T   K   Y   Q   M
tgatggcgcccagcccgctgacgcgaatgacacaGTGTTCCAGCTCCTCGGCAACGAGTT   2280
                                    F   Q   L   L   G   N   E   F CACCTTCGATGTCGACGTCTCCAACCTCGGCTGCGGCCTCAATGGCGCCCTCTACTTCGT   2340
 T   F   D   V   D   V   S   N   L   G   C   G   L   N   G   A   L   Y   F   V GTCCATGGATGCCGATGGTGGCATGTCCAAGTACTCGGGCAACAAGGCAGGTGCCAAGTA   2400
 S   M   D   A   D   G   G   M   S   K   Y   S   G   N   K   A   G   A   K   Y CGGTACCGGCTACTGTGATTCTCAGTGCCCCCGCGACCTCAAGTTCATCAACGGCGAGGC   2460
 G   T   G   Y   C   D   S   Q   C   P   R   D   L   K   F   I   N   G   E   A CAACGTAGAGAACTGGCAGAGCTCGACCAACGATGCCAACGCCGGCACGGGCAAGTACGG   2520
 N   V   E   N   W   Q   S   S   T   N   D   A   N   A   G   T   G   K   Y   G CAGCTGCTGCTCCGAGATGGACGTCTGGGAGGCCAACAACATGGCCGCCGCCTTCACTCC   2580
 S   C   C   S   E   M   D   V   W   E   A   N   N   M   A   A   A   F   T   P CCACCCTTGCACCGTGATCGGCCAGTCGCGCTGCGAGGGCGACTCGTGCGGCGGTACCTA   2640
 H   P   C   T   V   I   G   Q   S   R   C   E   G   D   S   C   G   G   T   Y CAGCACCGACCGCTATGCCGGCATCTGCGACCCCGACGGATGCGACTTCAACTCGTACCG   2700
 S   T   D   R   Y   A   G   I   C   D   P   D   G   C   D   F   N   S   Y   R CCAGGGCAACAAGACCTTCTACGGCAAGGGCATGACGGTCGACACGACCAAGAAGATCAC   2760
 Q   G   N   K   T   F   Y   G   K   G   M   T   V   D   T   T   K   K   I   T GGTCGTCACCCAGTTCCTCAAGAACTCGGCCGGCGAGCTCTCCGAGATCAAGCGGTTCTA   2820
 V   V   T   Q   F   L   K   N   S   A   G   E   L   S   E   I   K   R   F   Y CGTCCAGAACGGCAAGGTCATCCCCAACTCCGAGTCCACCATCCCGGGCGTCGAGGGCAA   2880
 V   Q   N   G   K   V   I   P   N   S   E   S   T   I   P   G   V   E   G   N CTCCATCACCCAGGACTGGTGCGACCGCCAGAAGGCCGCCTTCGGCGACGTGACCGACTT   2940
 S   I   T   Q   D   W   C   D   R   Q   K   A   A   F   G   D   V   T   D   ?

NCAGGACAAGGGCGGCATGGTCCAGATGGGCAAGGCCCTCGCGGGGCCCATGGTCCTCGT   3000
 Q   D   K   G   G   M   V   Q   M   G   K   A   L   A   G   P   M   V   L   V

CATGTCCATCTGGGACGACCACGCCGTCAACATGCTCTGGCTCGACTCCACCTGGCCCAT   3060
 M   S   I   W   D   D   H   A   V   N   M   L   W   L   D   S   T   W   P   I

CGACGGCGCCGGCAAGCCGGGCGCCGAGCGCGGTGCCTGCCCCACCACCTCGGGCGTCCC   3120
 D   G   A   G   K   P   G   A   E   R   G   A   C   P   T   T   S   G   V   P

CGCTGAGGTCGAGGCCGAGGCCCCCAACTCCAACGTCATCTTCTCCAACATCCGCTTCGG   3180
 A   E   V   E   A   E   A   P   N   S   N   V   I   F   S   N   I   R   F   G

CCCCATCGGCTCCACCGTCTCCGGCCTGCCCGACGGCGGCAGCGGCAACCCCAACCCGCC   3240
 P   I   G   S   T   V   S   G   L   P   D   G   G   S   G   N   P   N   P   P

CGTCAGCTCGTCCACCCCGGTCCCCTCCTCGTCCACCACATCCTCCGGTTCCTCCGGCCC   3300
 V   S   S   S   T   P   V   P   S   S   S   T   T   S   S   G   S   S   G   P

GACTGGCGGCACGGGTGTCGCTAAGCACTATGAGCAATGCGGAGGAATCGGGTTCACTGG   3360
 T   G   G   T   G   V   A   K   H   Y   E   Q   C   G   G   I   G   F   T   G

CCCTACCCAGTGCGAGAGCCCCTACACTTGCACCAAGCTGAATGACTGGTACTCGCAGTG   3420
 P   T   Q   C   E   S   P   Y   T   C   T   K   L   N   D   W   Y   S   Q   C

CCTGTAAacgaacctctctgaaggaggttctgagacacgcgcgattcttctgtatatagt   3480
 L   * tttattttcactctggagtgcttcgctccaccagtacataaacctttttttcacgtaa     3540 caaaatggcttcttttcagaccatgtgaaccatcttgatgccttgacctcttcagttctc   3600 actttaacgtagttcgcgttagtctgtatgtcccagttgcatgtagttgagataaatacc   3660 cctggaagtgggtctgggcctttgtgggacggagccctctttctgtggtctggagagccc   3720 gctctctaccgcctaccttcttaccacagtacactactcacacattgctgaactgaccca   3780 tcataccgtactttatcctgttaattcgtggtgctgtcgactattctatttgctcaaatg   3840 gagagcacattcatcggcgcagggatacacggtttatggaccccaagagtgtaaggacta   3900 ttattagtaatattatatgcctctaggcgccttaacttcaacaggcgagcactactaatc   3960
```

```
                                   -continued
aacttttggtagacccaattacaaacgaccatacgtgccggaaattttgggattccgtcc    4020 gctctccccaaccaagctagaagaggcaacgaacagccaatcccggtgctaattaaatta    4080 tatggttcattttttttaaaaaaattttttcttcccattttcctctcgcttttcttttc    4140 gcatcgtagttgatcaaagtccaagtcaagcgagctatttgtgctatagctcggtggcta    4200 taatcagtacagcttagagaggctgtaaaggtatgataccacagcagtattcgcgctata    4260 agcggcactcctagactaattgttacggtctacagaagtaggtaataaaagcgttaattg    4320 ttctaaatactagaggcacttagagaagctatctaaatatatattgaccctagcttatta    4380 tccctattagtaagttagttagctctaacctatagatagccaaatgctataataggtacc    4440 agggttcaaaa                                                     4451
```

SEQ ID No. 10
CBH1 protein sequence. Signal sequence is given in italic,
the CBD underlined in bold.

```
MYAKFATLAA  LVAGAAAQNA  CTLTAENHPS  LTWSKCTSGG  SCTSVQGSIT    50

IDANWRWTHR  TDSATNCYEG  NKWDTSYCSD  GPSCASKCCI  DGADYSSTYG   100

ITTSGNSLNL  KFVTKGQYST  NIGSRTYLME  SDTKYQMFQL  LGNEFTFDVD   150

VSNLGCGLNG  ALYFVSMDAD  GGMSKYSGNK  AGAKYGTGYC  DSQCPRDLKF   200

INGEANVENW  QSSTNDANAG  TGKYGSCCSE  MDVWEANNMA  AAFTPHPC?V   250

IGQSRCEGDS  CGGTYSTDRY  AGICDPDGCD  FNSYRQGNKT  FYGKGMTVDT   300

TKKITVVTQF  LKNSAGELSE  IKRFYVQNGK  VIPNSESTIP  GVEGNSITQD   350

WCDRQKAAFG  DVTD?QDKGG  MVQMGKALAG  PMVLVMSIWD  DHAVNMLWLD   400

STWPIDGAGK  PGAERGACPT  TSGVPAEVEA  EAPNSNVIFS  NIRFGPIGST   450

VSGLPDGGSG  NPNPPVSSST  PVPSSSTTSS  GSSGPTGGTG  VAKHYEQCGG   500

IGFTGPTQCE  SPYTCTKLND  WYSQCL       *                   526
```

SEQ ID No. 2
DNA sequence and amino acid sequence of complete *Chrysosporium* XylF (Xyl1) gene including promoter and terminator sequences. Position of the protein encoding part of the gene is indicated in bold with aminoacid translation below the sequence. Promoter, terminator and intron sequences are given in small case. The signal peptide is shown in italic letters and the cellulose binding domain (CBD) is shown in bold underlined letters.

```
tcatcaacttggcgtttggatgtactaatattacacgtcgtttgcnnagcggagtctgtg     60 tcatctccgtggggtcgggtgctccagacgacgcttcgggccgatcctgaattcgggaag    120 gaaacggttcggctaatcaggtcctctaaaatataacgaagcactacagagggagttcct    180 cagaggacatcgtatcaaccgaagaacgaagcgccgaaaggactgatcaaaacaggagta    240 ggtagggatgtgtgagtacctaaactttccatacctgacataaaatcatcatggtgcttc    300 agacctgtttgatgaggcgagggcggaggccgcattgtattttcgttccttccttctttt    360 tgttagtatatctnagggttccatcgtaaaatggaatcttccagctctactagtaattag    420 aacaatagttctgatgtcgtgcgccaagctttttcagatgactgccaaaaacccatcatg    480 ggtatggacaaaagcagtaatcggagtcacaacgccgcattttccttcatgatttccgtc    540 aaccggagaggtcggaggaggactccggccacatgtgatgcgaagaagtacatggcgcca    600 tggttctaacctcttatagtctgaaaatgcgcggaggccagcgaagccaagcccgggaac    660
```

-continued

```
cgttcttgtcatggtttcagtattgtttcgctaaacattctatccgattcgcgataggtg    720 cggctgccaccgaaggttgtatccttaaagctttggtaagtacggagtacggaaatggaa    780 acgcgccgcagtcctggttccatcggtatcctccgcatgctccgccaaaaaagaaaacc    840 cgggtatgtttacaaagg<u>atataag</u>agacaagatgcaccacccgcccccttcccatctgc    900 cggttgcccacgtcgccgtcgactgcttgtccgcttcctacctgcagcctcttcagaga    960 ccatcaaacATGCGTACTCTTACGTTCGTGCTGGCAGCCGCCCCGGTGGCTGTGCTTGCC   1020
          M  R  T  L  T  F  V  L  A  A  A  P  V  A  V  L  A CAATCTCCTCTGTGGGGCCAGTgtatgtaattgccttactcggaaaatagtcaccactag   1080
 Q  S  P  L  W  G  Q  C agggacttaagctcactacttcctgtttcacaatagGCGGCGGTCAAGGCTGGACAGGTC   1140
                                     G  G  Q  G  W  T  G CCACGACCTGCGTTTCtGGCGCAGTATGCCAATTCGTCAAgtcagtaactgcttttatt   1200
P  T  T  C  V  S  G  A  V  C  Q  F  V  N tcttttctctctgggattacgatttcgttttgcacttagcttggttctgcatttcattgt   1260 tgtattgttctcttttttgtgtgtgagaggttttattaccacctaaaggccatttgctaac   1320 aaatctccccagTGACTGGTACTCCCAATGCGTGCCCGGATCGAGCAACCCTCCTACGGG   1380
             D  W  Y  S  Q  C  V  P  G  S  S  N  P  P  T  G CACCACCAGCAGCACCACTGGAAGCACCCCGGCTCCTACTGGCGGCGGCGGCAGCGGAAC   1440
 T  T  S  S  T  T  G  S  T  P  A  P  T  G  G  G  S  G  T CGGCCTCCACGACAAATTCAAGGCCAAGGGCAAGCTCTACTTCGGAACCGAGATCGATCA   1500
 G  L  H  D  K  F  K  A  K  G  K  L  Y  F  G  T  E  I  D  H CTACCATCTCAACAACAATGCCTTGACCAACATTGTCAAGAAAGACTTTGGTCAAGTCAC   1560
 Y  H  L  N  N  N  A  L  T  N  I  V  K  K  D  F  G  Q  V  T TCACGAGAACAGCTTGAAGTGGGATGCTACTGAGCgtgagtgacctctcctccttctccc   1620
 H  E  N  S  L  K  W  D  A  T  E  P gacaataatagataattacgagccggttcgaggctgacattgcgcgattctagCGAGCC   1680
                                                       S  R GCAATCAATTCAACTTTGCCAACGCCGACGCGGTTGTCAACTTTGCCCAGGCCAACGGCA   1740
 N  Q  F  N  F  A  N  A  D  A  V  V  N  F  A  Q  A  N  G  K AGCTCATCCGCGGCCACACCCTCCTCTGGCACTCTCAGCTGCCGCAGTGGGTGCAGAACA   1800
 L  I  R  G  H  T  L  L  W  H  S  Q  L  P  Q  W  V  Q  N  I TCAACGACCGCAACACCTTGACCCAGGTCATCGAGAACCACGTCACCACCCTTGTCACTC   1860
 N  D  R  N  T  L  T  Q  V  I  E  N  H  V  T  T  L  V  T  R GCTACAAGGGCAAGATCCTCCACTGGGACGTCGTTAACGAGATCTTTGCCGAGGACGGCT   1920
 Y  K  G  K  I  L  H  W  D  V  V  N  E  I  F  A  E  D  G  S CGCTCCGCGACAGCGTCTTCAGCCGCGTCCTCGGCGAGGACTTTGTCGGCATCGCCTTCC   1980
 L  R  D  S  V  F  S  R  V  L  G  E  D  F  V  G  I  A  F  R GCGCCGCCCGCGCCGCCGATCCCAACGCCAAGCTCTACATCAACGACTACAACCTCGACA   2040
 A  A  R  A  A  D  P  N  A  K  L  Y  I  N  D  Y  N  L  D  I TTGCCAACTACGCCAAGGTGACCCGGGGCATGGTCGAGAAGGTCAACAAGTGGATCGCCC   2100
 A  N  Y  A  K  V  T  R  G  M  V  E  K  V  N  K  W  I  A  Q AGGGCATCCCGATCGACGGCATCGGCACCCAGTGCCACCTGGCCGGGCCCGGCGGGTGGA   2160
 G  I  P  I  D  G  I  G  T  Q  C  H  L  A  G  P  G  G  W  N ACACGGCCGCCGGCGTCCCCGACGCCCTCAAGGCCCTCGCCGCGGCCAACGTCAAGGAGA   2220
 T  A  A  G  V  P  D  A  L  K  A  L  A  A  A  N  V  K  E  I TCGCCATCACCGAGCTCGACATCGCCGGCGCCTCCGCCAACGACTACCTCACCGTCATGA   2280
 A  I  T  E  L  D  I  A  G  A  S  A  N  D  Y  L  T  V  M  N ACGCCTGCCTCCAGGTCTCCAAGTGCGTCGGCATCACCGTCTGGGGCGTCTCTGACAAGG   2340
 A  C  L  Q  V  S  K  C  V  G  I  T  V  W  G  V  S  D  K  D ACAGCTGGAGGTCGAGCAGCAACCCGCTCCTCTTCGACAGCAACTACCAGCCAAAGGCGG   2400
 S  W  R  S  S  S  N  P  L  L  F  D  S  N  Y  Q  P  K  A  A
```

-continued

```
CATACAATGCTCTGATTAATGCCTTGTAAgaggaggtatattattttagaggcaatgaa    2460
 Y  N  A  L  I  N  A  L  * gctaggaggaaagaggggaagtgaggtaattagctaggacaggcaaatctagcagcaatt    2520 ataagtcaacactatataaaatattcctataatggcttgtgcttcggtgtgcaaaaaaaa    2580 aaaaaaaaaaaaaaaaaaaaaaaaaaaaaaactcaaaaacaaaaatgatccaacatgatt    2640 cgaaatggcgaccttgcaaatgcacacctcagataataccactatacaatacaccttaaa    2700 tggcacctaaatccatttgtctgcggtcatagacggggcttaagaagcctgggatgcagg    2760 tgtcgatgcaagggttacgtcagtgtatgatatgagtatgaaccatgctgtctgggtaat    2820 tctccactttccctccccttacgactcttcgggtgtgcctctctagaaagtcgactcctg    2880 gcgcctcagatcgccctttggctctgttcggtacaatgacgtccgctggtttcttccaaa    2940 gaccaggtatttctcccgtggcaacaaagaataccaaatacctatatcgaaccgtagtct    3000 tctgataattagatgtctctcaaggcgcgg                                3030
```

SEQ ID No. 11
XylF protein sequence. Signal sequence is given in italic, the CBD is underlined in bold.

```
  1 MRTLTFVLAA APVAVLAQSP LWGQCGGQGW TGPTTCVSGA VCQFVNDWYS

51 QCVPGSSNPP TGTTSSTTGS TPAPTGGGGS GTGLHDKFKA KGKLYFGTEI

101 DHYHLNNNAL TNIVKKDFGQ VTENSLKWDA TEPSRNQFNF ANADAVVNFA

151 QANGKLIRGH TLLWHSQLPQ WVQNINDRNT LTQVIENHVT TLVTRYKGKI

201 LHWDVVNEIF AEDGSLRDSV FSRVLGEDFV GIAFRAARAA DPNAKLYIND

251 YNLDIANYAK VTRGMVEKVN KWIAQGIPID GIGTQCHLAG PGGWNTAAGV

301 PDALKALAAA NVKEIAITEL DIAGASANDY LTVMNACLQV SKCVGITVWG

351 VSDKDSWRSS SNPLLFDSNY QPKAAYNALI NAL*
```

SEQ ID No. 3
DNA sequence and amino acid sequence of complete *Chrysosporium* EG3 gene including promoter and terminator sequences. Promoter, terminator and intron sequences are given in small case. Putative glycosylation site is given with an asterisk (*). The signal peptide is shown in italic letters and the propeptide is shown in underlined letters.

```
ccgccctggagcgtggaccgtggggacaggcggcaaatgagaccctattggggcgcatcg     60 acggtgcagaaccgaggttccgggaccttggcagagcggcccagggaccccgccatccag    120 ctatgcgcctccacagaagccgaccgatgctcgggttgcatcccgagatcgtcggtatta    180 aggagaggggagaagaagaagggggggggggggggggaatgagacaacaacactcaggcg    240 cgccaattagaacttcaacgagcctccttcctgcatccagacaagaccgaggtcgagccg    300 ggtactatgcaagcgtcccgtgccgcgtgatgtcgctcgtaggtgttgacaggttctcag    360 ctgtttcttgaatccccggaggtggactaaaggggcaagagaccatggtaagctccgtc     420 gccagccctcccgttgcggagcggaagccgaggaccgaccttcttctggagaacccgggc    480 tgcccggggcggaggcgggttccgccttttttttaaccagtccgagttgttgtcgcgaact    540 gcgctcggttgcaacgtcagtgtccaatcggcaggcgtatcgcgacccggtaaggggggtt    600 acggcatgtgttctcggcttccgcacatcaaaacttactcgtattcgtcctgaccttggt    660 aattaattatgtcgcaagacaaggagttgtttgagacgactccggcgcgcataattacac    720
```

-continued

```
agtggtgcagtattatatatctttctcccgtagggacgacgacaaagacccgtcagtgat    780 taataataattagtagcagtttctttctttcaagactcaagaatactcctttccgccatc    840 gtggcagcgtttagattcatcATGCAGCCGTTTCTGCTCTTGTTCCTCTCGTCGGTCACG    900
                      M  Q  P  F  L  L  L  F  L  S  S  V  T GCGGCGAGCCCCCTGACGGCGCTCGACAAGCGGCAGCAGGCGACGTTGTGCGAGCAGTAC    960
 A  A  S  P  L  T  A  L  D  K  R  Q  Q  A  T  L  C  E  Q  Y GGCTACTGGTCGGGCAACGGTTACGAGGTCAACAACAACAACTGGGGCAAGGATTCGGCC   1020
 G  Y  W  S  G  N  G  Y  E  V  N  N  N  N  W  G  K  D  S  A TCGGGCGGCCATCAGTGCACCTACGTCGACAGCAGCAGCTCCAGCGGCGTCGCCTGGCAC   1080
 S  G  G  H  Q  C  T  Y  V  D  S  S  S  S  S  G  V  A  W  H ACGACCTGGCAGTGGGAAGGAGGCCAGAACCAGGTCAAGAGCTTCGCCAACTGCGGCCTG   1140
 T  T  W  Q  W  E  G  G  Q  N  Q  V  K  S  F  A  N  C  G  L CAGGTGCCCAAGGGCAGGACCATCTCGTCCATCAGCAACCTGCAGACCTCCATCTCGTGG   1200
 Q  V  P  K  G  R  T  I  S  S  I  S  N  L  Q  T  S  I  S  W TCCTACAGCAACACCAACATCCGCGCCAACGTGGCCTACGACCTCTTCACCGCGGCAGAC   1260
 S  Y  S  N  T  N  I  R  A  N  V  A  Y  D  L  F  T  A  A  D CCGAACCACGCGACCAGCAGCGGCGACTACGAGCTCATGATCTGgtcagttttttttttc   1320
 P  N  H  A  T  S  S  G  D  Y  E  L  M  I  W tttttttcttttcttctctttttcttttcttttcctttctcctgttttattttcttatccat   1380 tgcttcgccctctttccttaaccctgctgactctctcttcttgtcaatgatactgtaata   1440 gGCTGGCGAGATTCGGCGACGTCTACCCCATCGGCTCGTCCCAGGGCCACGTCAACGTGG   1500
  L  A  R  F  G  D  V  Y  P  I  G  S  S  Q  G  H  V  N  V

CCGGCCAGGACTGGGAGCTGTGGACGGGCTTCAACGGCAACATGCGGGTCTACAGCTTCG   1560
 A  G  Q  D  W  E  L  W  T  G  F  N  G  N  M  R  V  Y  S  F

TAGCGCCCAGCCCCCGCAACAGCTTCAGCGCCAACGTCAAGGACTTCTTCAACTATCTCC   1620
 V  A  P  S  P  R  N  S  F  S  A  N  V  K  D  F  F  N  Y  L

AGTCCAACCAGGGCTTCCCGGCCAGCAGCCAATACCTTCTCAgtaaggagacgagatctc   1680
 Q  S  N  Q  G  F  P  A  S  S  Q  Y  L  L  I gaacagcataccatatatgcgtgcggtacaagtgcactaaccccctttttttttcccgttc   1740 gcagTCTTCCAGGCGGGCACCGAGCCCTTCACCGGCGGCGAGACCACCCTTACCGTCAAC   1800
    F  Q  A  G  T  E  P  F  T  G  G  E  T  T  L  T  V  N AACTACTCTGCAAGGGTTGCTTAAacaggaaggccgaggatggcccccaaggccgttgcg   1860
 N  Y  S  A  R  V  A  * ggttcacgagctctcttcttttcaagtgctgtacatacataattagcgtaccaagtcata   1920 gctgtttgtcagcttcaaactaagtgctcgcccacaaaagagggggggaggggaaaataac   1980 aaattgccgaacgcagtgataagcttctgggagcgttgaaagcagtctacagtaggtggc   2040 tgyacgaaggaaaagagtgccttattaaagctatctacaaaggagacaaaacgactgata   2100 tttatggacaaagggactggccaatgcgttaaacagcctcatacagctgtagcatatata   2160 tggctaatacgtttggaagctctatagcttccgacacaccccctagttaaacgtagtagt   2220 cgtttaactacgctttgyggtgatactgttcttggtattatatccttttgtcgctcttacc   2280 tcgatagctccttcagggggcctgccttctgtattcggaagtctaaaagagtcgagtata   2340 gtagagcgattcctttaaagctatagatcaaatatggccattataactatagtagtaata   2400 gtattactagttttaatcataatagtaataataggatgacgcctcttatgcttgaatcaa   2460 tagatgactcgttaggtctacctattacaaacactataactgctagtaggtcgactcctg   2520 ctcctataacacctcgtaagtataagtatactaaagcttctataccgtaagtgttcctat   2580 tgtcccatttgattaactttattactagttttgtagttttcttagtagttctagcgatt   2640 taagcgagtttacgtggttcggcttcttctggttaatttgatagcgactctatcacagtt   2700
```

-continued

```
tctagcgctttactagtcacgtctagatcgtttaagctgactaaatatagcaacatcgaa    2760 gctagcgagctttgtaaggtaccctatagaatatatatacggtcggctctagtaggacgt    2820 tcttttagcaaatgtcacgatcattccggcgttagctcctactattactattatacctat    2880 agttcctataagtgtagggagatatacgttaatcgcctatacgtctaatagctcttataa    2940 tacttatactaactataatggtagtcttgcttcttatattaggtcggctaaggacttaac    3000 gaaggctctaatggatagagctaaggcttctataag                           3036
```

SEQ ID No. 12
EG3 protein sequence. Signal (prepro)sequence is given in italic, the putative pro sequence underlined italic

```
  1  MQPFLLLFLS SVTAASPLTA LDKRQQATLC EQYGYWSGNG YEVNNNNWGK

51  DSASGGHQCT YVDSSSSSGV AWHTTWQWEG GQNQVKSFAN CGLQVPKGRT

101  ISSISNLQTS ISWSYSNTNI RANVAYDLFT AADPNHATSS GDYELMIWLA

151  RFGDVYPIGS SQGHVNVAGQ DWELWTGFNG NMRVYSFVAP SPRNSFSANV
                                                          *

201  KDFFNYLQSN QGFPASSQYL LIFQAGTEPF TGGETTLTVN NYSARVA*
```

SEQ ID No. 4
DNA sequence and amino acid of partial *Chrysosporium* GPD gene including promoter sequences. Promoter and intron sequences are given in small case. The 3' end of the gene is lacking.

```
tgagcagcaatgagcagcaatgagcattcctgggccaccgagtctgagtgccagtacgga     60 gtatcgtacttcgtaccggggtttgatttggtgacggtgcttttcacctctcgatgcccg    120 aaatcgggtctaagctgagtttgatcaaatatgtgactccaacatcgccccttcggcaa    180 accccgtcgacacgtgtgtcatccttccattgcaagcgatcactcgcagggcgtgacgat    240 gaacgagattttgcccggaccgattcgcggatatagcggcagccgaccagccctaccac    300 actgatggccgtgtcactagtgtatgctcccagaaccgcaagcatacactgggcaatgct    360 tggtatgcagttgaggcagctttatgtttccatacccttccacttcggctcggggactcg    420 gcggggtcgcggaagtttgacggcagccgtcgggccttaggccgagattaccgtggttgt    480 ggcccagttttagccgttcccgtccgtttcctaccggaccatgattttcgtgaaccattg    540 caatcccgaagcgcatttccgacgttaaggagttacctccgctgcccagaattcatgatc    600 gtggccggctcaaggcagcgtggcggggcatccgtgtcaagctcccaggaggaggtgcgc    660 gatttcaaatccgggccaaaacaggccaagactggctggccaaaaaaggagcgtagacg    720 gcccgggacatcggacgtcagctcgcagccacccaaaaccggtccgatctactcgcttac    780 tgtggtagttcaggtacttttgagtagtaaaaacgctacggcagggccgggggttcccc    840 ggtgacggaggtgcctctgcggtggcgaacatcccacgcactctcgagctacggtgacac    900 ctcgtgtcctgttggtcttgcaatgctggggcggcaggaaatgcgtcgcgctcctcccgg    960 ccaagacctaaaacagacagcgccgcaaagtcgctcactagcaccgcgaaacgaagatgc   1020 cccacctcaacgcaatctgtgatgcaagcaattgggaaggctcaccccacctcagcgagg   1080 ggctcaaccatttttattatcagctcatgccaccacaacatgactgttttctttccttgc   1140
```

```
                        -continued
tcatcccacatttgacaaaaatcgtcgattaatctctttccatacaggccgtccgcgctc  1200 tgataaccacataaaagtctcttcagtcaacagctcaaagctccctcatccctccaggta  1260 agcagccaaagagctcccccacggaccccgcactgcctcatcccgcctgtatcggacctg  1320 cgcgacccagcagagaatcccaaacctttgctgcttgctgcccggttccggactgagctg  1380 caacccaagcctttaaaaagcttttcccttctcccacggtgtcaactctgtcctatccct  1440 ccgacatccgttgagctcaacaactccccgaaccttttaccccgcgccgagctacccctc  1500 catcaaaccaccctgacagctcgctcactcacctccccacatcacagaaatcaaaATGAC  1560
                                                         M  T  —

TATCAAGGTCGGCATCAACGGTTTCGGCCGTATCGGCCGTATCGTCTTCCGCAACTCCAT  1620
  I  K  V  G  I  N  G  F  G  R  I  G  R  I  V  F  R  N  S  I  —

CGAGCACTCGGATGTCGAGATCGTTGCCGTCAACGACCCCTTCATTGAGCCCAAGTACGC  1680
  E  H  S  D  V  E  I  V  A  V  N  D  P  F  I  E  P  K  Y  A  —

Tgtaagtagtttttttttccttcctcgcgttctttcctgttccatcgacagtacgagat  1740

GatcttgcaggcggatcggagctaaccgcgattgtcgtacagGAGTACATGCTCAAGTAT  1800
                                            E  Y  M  L  K  Y  —

GACTCGACCCACGGTATCTTCAACGGCACCATCGCCGTCGAGGGCAACGACCTCATTGTC  1860
  D  S  T  H  G  I  F  N  G  T  I  A  V  E  G  N  D  L  I  V  —

AACGGCAAGAGGGTCAAGTTCTACACTGAGCGGGMCCCCGCCAACATTCCCTGGARGGAA  1920
  N  G  K  R  V  K  F  Y  T  E  R  ?  P  A  N  I  P  W  ?  E  —

ACTGGTGCCGAGTACATMRTCGAGTCGACCGGTGTGTTCACCAMCACCSAGAAGGCTAGC  1980
  T  G  A  E  Y  I  ?  E  S  T  G  V  F  T  ?  T  ?  K  A  S  —

GCCCACCTCAAGGGCGGCGCCAAGCGCGTCATCATCTCTGCTCCCTCGGCCGATGCCCCC  2040
  A  H  L  K  G  G  A  K  R  V  I  I  S  A  P  S  A  D  A  P  —

ATGTACGTCATGGGCGTCAACGAGAAGACCTACGACGGCAAGGCCCAGGTCATCTCTAAC  2100
  M  Y  V  M  G  V  N  E  K  T  Y  D  G  K  A  Q  V  I  S  N  —

GCCTCGTGCACCACCAACTGCCTGGCTCCCCTCGCCAAGGTCATCCACGACAAGTTCGGC  2160
  A  S  C  T  T  N  C  L  A  P  L  A  K  V  I  H  D  K  F  G  —

CTCGTTGAGGGTCTCATGACCACCGTCCACTCCTACACTGCCACCCAGAAGACCGTCGAT  2220
  L  V  E  G  L  M  T  T  V  H  S  Y  T  A  T  Q  K  T  V  D  —

GGTCCCTCTGCCAAGGACTGGCGTGGTGGCCGTGGTGCTGCTCAGAACATCATCCCCAGC  2280
  G  P  S  A  K  D  W  R  G  G  R  G  A  A  Q  N  I  I  P  S  —

AGCACTGGCGCCGCCAAGGCCGTCGGCAAGGTCATCCCTGAGCTCAACGGCAAGCTCACC  2340
  S  T  G  A  A  K  A  V  G  K  V  I  P  E  L  N  G  K  L  T  —

GGCATGTCCCTCCGTGTCCCCACCCCCAACGTTTCCGTTGTCGACCTCACCTGCCGCCTC  2400
  G  M  S  L  R  V  P  T  P  N  V  S  V  V  D  L  T  C  R  L  —

GAGAAGGAGGCTACCTACGACGACATCAAGGCCGCCATCAAGGAGGCCGCCGCCGGCCCC  2460
  E  K  E  A  T  Y  D  D  I  K  A  A  I  K  E  A  A  A  G  P  —

CTCAAGGgtgagttatctggttccttttttttttttggagaacgacacatgctgataaa  2520
  L  K  G acccagGCATCCTCGACTACACTGAGG                                   2547
       I  L  D  Y  T  E
```

SEQ ID No. 13
  GPD protein sequence (the C-terminus is lacking in the sequence available).

MTIKVGINGF GRIGRIVFRN SIEHSDVEIV AVNDPFIEPK YAEYMLKYDS

THGIFNGTIA VEGNDLIVNG KRVKFYTER? PANIPW?ETG AEYI?ESTGV

FT?T?KASAH LKGGAKRVII SAPSADAPMY VMGVNEKTYD GKAQVISNAS

CTTNCLAPLA KVIHDKFGLV EGLMTTVHSY TATQKTVDGP SAKDWRGGRG

-continued

```
AAQNIIPSST GAAKAVGKVI PELNGKLTGM SLRVPTPNVS VVDLTCRLEK

EATYDDIKAA IKEAAAGPLK GILDYTE
```

SEQ ID No. 5:
C1-EG5 "25 kD" (Family 45) gene obtained by PCR based on "25 kD Endo" protein sequencing and family 45 homology analysis.

```
-3309                                           GCTTAGGAG    -3301

AATCACGAGAAGCTAATTGGGCTCTATAGTATCCGACAAGATGACCCAGAGCGAGATTGA   -3241

GGATCTCGAGGGAACCCTGAAGCAGAGCAGCAACAACGACACCAGCCTCCTCCGCGACCT   -3181

GCTCGACAAGATTCCCGATGGCCTCCTCGGCGGCAACAACAAATCCAAGCTGGACGATAT   -3121

CCAGAGCAACGCGCAGGCCGCGCAGATGGAGAACCTGAGCGTCTCGCCGCGGGAACCCGA   -3061

GGAGCTGACCAGATACGTCCAGGAAGTGTTCCGTCAGATCATGCCCGCCATCAAGTTCCA   -3001

TGACCAGCTTCTCCAGGACATCTCGGAGGCCATCGACAAGATCCCGGTGCTGCCCAAGAT   -2941

TGTGGAGCAGCTGGAGGAGCAGATGTCCATCTTTGTATTCCAGATCATGGCCCCGTTCGT   -2881
creA

GGTTCCGCTTATCGAGCAGATCAAGAACGAGCTCGCGACTGGCTCCAGCGAGATCATCCA   -2821

GAGCAGCAGGGCTGAGCAGCACAACGTCTTTGAGGACGACAACGCCACCGACCCGACTCA   -2761

CTCGATGTTGGCCAAGGACCACTTTAGTAACGTAAAGCCGACCCTAATCAGAAGCTCGCA   -2701

TGTAGAATTGAGTTAGACTGACGCGACTTGTTTCCCGTCTCTGTAGATCCTCAACGAGAT   -2641

CGGCGGTCGCGCCGCCTCCAAGGTCGTCTCCTGGGTCGTCCCGCAGCTCATGGAGGCCTG   -2581

GGACGATGACAGCGTCGACGTGGACCGCCTGCTTGACAAGATCATTTACGGAGTGTTCCA   -2521

CCATCCCGCGCAGCGCACCATGGGCCCTGAGGGGGCGTCCGAGGGCCGGGAGCTCATCTT   -2461

CAACATGGTGCGCGAGTGGTGGGAGGACATGAGCGACGGGCAGCGCGACGAGTACCGGGG   -2401
creA

CAAGCTGAGCCGCGAGGGAGTCGAGAGAGGCGACAACCACCGCGAGGGCCAGCACGACTG   -2341

CGGCCACGGCTGCGGGGGCAAGCTCAAGATGCACAAGAACTTCCGGAACGAGGCGCCCCA   -2281
creA

GACGGTAGAGGACCAGATCGCGGGCGCCGCCGCGGAGGCCATCATGGGAGGCGTCAAGCA   -2221
creA

GGGCCTGTCGCAGGCCGTGCAGAACGCCGCCGGCCGCCAGGAGTCGTCGGAGAGCAGCGG   -2161

CCTGGGTGGGTTCATCAGCAGCGTCGCGGGCGGCCTCCTGGGCGGCGCCCTCAAGAGGGA   -2101

CGAGACAGAGTCGTACCAGGCCGGCGGCCGCACCGAGGACGGCGGGTACACGCAGACCAC   -2041

GACCGAGTACGGCTACTCCGGAGGCCGCTACGGCCAGGCCCAGTACACGGAGACGCAGTA   -1981

CGGCGGCGGCGGCGGCCGCAGCGAGTACCGCCGCTACGAGCAGCGCGAGGATGATGA     -1921

CGGCCGGGTCCAGAGCTACGGATACACGGAACAGCGCACCGAGACGCGCTACGACAGCTA   -1861

CTCGGGTGGCTATGGCGGCCGCGAGGAGACCAGCAGCTATGGCGGCGGCGGCAGCGCGAG   -1801

CGAATACATTCGTAGCTCCCAGCAGAGTAGCTACGGTGGCAGCGGCTATGGCAGTGGGTA   -1741

CGGTCGTCGTGATGAAGAAGAGCAGCGGCTATGGAAGTGGTTACGGTCGTCGTGATGA    -1681

AGAGGAGAGTGGTGGTTATGGTGGCGGCTATGGCCGCCGTCAGGAAGAAGAGAGTAGCAG   -1621

CTATGGAAGCGGTTATGGTCGTCGTCGTGATGAAGAAGAGAGCGGCGGTTATGGTGGTGG   -1561

CTACGGCCGCCGTCAGGAAGAAGAGAGTAGCGGCTATGGAAGTGGTTACGGTCGTCGTGA   -1501
```

```
                                                             -continued
TGAAGAAGGGAGCGGCGGTTATGGTGGTGGCTACGGCCGCCGTCATGAGGAAGAGAGCAG    -1441

TGGTTACGGCAGCGGCTATGGTCGTCGCCATGAAGAGGAGGGCGGTGGCTACGGCAGTGG    -1381

TTACGGCCGCCGGCGCAACGACGAGGAGGAAGAGGAGGATGGCGGACGCCGGAGGTGGGG    -1321
creA

TTACTAGGGTGAACTCTTCCGGCCGGTCTCTTGTTGTGAACCTTGCTGTTGCATGGGCAG    -1261

GACCGGTGCATCATGAACAGGACGGTGCGCTGTGTTTTTTTTTCTCGGGGTCTTGATTG    -1201

TTTGTTGAATCTCCCTTTTCGAGGATACGAGCTCTCTCGGGGACGAATAGATGAAGGCAA    -1141

TCTGACAGATTTGCTCTCAAAAAAAGACTGATATCTCTTCCACCATGCACTGTATGTACA    -1081
nit2

TTACATACATTATCCCCCTCCACTGGATTCGCACAACGGAAAGCAATGGCGCGCTGATTC    -1021

AAGAACCATCAGGGCTGTCATTGGCTTGTTTTGTGCCGTGGCCGCGGTGACGCCCACTAT    -961

GACTCTCTGGGCAGGCGGCAACTGGGTGCCAGATATATTAATCCGGGGCATAGCGCATAT    -901
creA

CTTCCTTGATTTGTAGAGTACTAGTACACTAACCCCCTTCTCCACATGGGGCCACTGTTC    -841
nit2

GGTAGATCTGCCCGAAGTGCAAGTGCGGGGGGGCCAAACTAGGTAATATCCTCCCGCTC    -781
creA

TCCCGAGTGCGCGGACTAACCGTCATTGCTCCCAGAGGCTTGCACTCTATCGCAGGCCTT    -721
nit2

TTCCAATAAGGATGGGCGTTCGGCGGTGATGATGCCGGTCGTGCGGGGCATACGGGGAG    -661
creA

GGTAGATAGAAAATAACGACGCTGGTGTTTTGGAGAGGGGAGGGGGACTATTAGGGGAGG    -601
creA    nit2

GAAATACAGGGGCAGGGGGTGAGACGGGTGACGTTCCGGCGGAACCTCGCGCTTGTCAAA    -541

CAAGCAGCCCTGTTAGGTTGCTCTAGACTAGTGTACATACATACATATGTACATACTGTA    -481

TGTACTGCACATACTTTAACTTGGTGCTTCCCTGTGAGCCGCCAGGAACATCACAACTGC    -421

AAGCGGAAAAGGCCCCATATACGGGGCGGCTTGTCGGGATGGCTCCCCCCTTCGGAACGG    -361

GTCTGACTTCCGAGGATTTTACCTGCTTCATTTGGGTATTCTGCGATGGCCTGTTCAACC    -301

CTTCCCCTGGCCGAACCGTTTCTTGGCTCGATCCTAGTGTACACTACACTACTCGTAGAC    -241

TGCCTGCCCGACGATCCGCGGGAACGGGCCAGGAGTGTGGAGTGGAGACGGGCGGCGGTG    -181
creA

ATGTCGTGTAATTAAATATATAAGTGAGAGTGTTTTTTGACTGCCCCGGGTTCTGGTAGT    -121
TATA box

TGAAGGGAAGTTCGATGCTCTCTGCTGTCGTCGCTCTCGTCGCTCTCGTCGGCATCCTCC    -61

ATCCGTCCGCCTTTGATAACCCGCTCCCCGACTCAGTCAAGACGACGCATACTTGGCACC    -1

ATGCATCTCTCCGCCACCACCGGGTTCCTCGCCCTCCCGGCCCTGGCCCTGGCCCAGCTC    +60
Put.SS

M   H   L   S   A   T   T   G   F   L   A   L   P   A   L   A   L   A   Q   L    20

TCGGGCAGCGGCCAGACGACCCGGTACTGGGACTGCTGCAAGCCGAGCTGCGCCTGGCCC    +120
 S   G   S   G   Q   T   T   R   Y   W   D   C   C   K   P   S   C   A   W   P     40

GGCAAGGGCCCCTCGTCTCCGGTGCAGGCCTGCGACAAGAACGACAACCCGCTCAACGAC    +180
 G   K   G   P   S   S   P   V   Q   A   C   D   K   N   D   N   P   L   N   D     60

GGCGGCTCCACCCGGTCCGGCTGCGACGGGGCGGCAGCGCCTACATGTGCTCCTCCCAG    +240
 G   G   S   T   R   S   G   C   D   A   G   G   S   A   Y   M   C   S   S   Q     80

AGCCCCTGGGCCGTCAGCGACGAGCTGTCGTACGGCTGGGCGGCCGTCAAGCTCGCCGGC    +300
 S   P   W   A   V   S   D   E   L   S   Y   G   W   A   A   V   K   L   A   G    100

AGCTCCGAGTCGCAGTGGTGCTGCGCCTGCTACGAGCTGACCTTCACCAGCGGGCCGGTC    +360
 S   S   E   S   Q   W   C   C   A   C   Y   E   L   T   F   T   S   G   P   V    120
```

```
                                          -continued
GCGGGCAAGAAGATGATTGTGCAGGCGACCAACACCGGTGGCGACCTGGGCGACAACCAC    +420
 A  G  K  K  M  I  V  Q  A  T  N  T  G  G  D  L  G  D  N  H    140

TTTGACCTGGCCgtgagttgcctccccttctccccggaccgctcagattagatgagatta    +480
       Intron 1
 F  D  L  A                                                     144 gactttgctcgtaaatcggtccaagattcccttgactgaccaacaaacatcatacgggca    +540 gATCCCCGGTGGCGGTGTCGGTATTTTCAACGgtaagctggtgccccggacccctcccc     +600
                             Intron 2
 I  P  G  G  V  G  I  F  N                                     154 ggacccctccccttttcctccagcgagccgagttgggatcgccgagatcgagaactcac    +660 acaacttctctctcgacagCCTGCACCGACCAGTACGGCGCTCCCCCGAACGGCTGGGGC    +720
                    A  C  T  D  Q  Y  G  A  P  P  N  G  W  G   168

GACCGCTACGGCGGCATCCATTCCAAGGAAGAGTGCGAATCCTTCCCGGAGGCCCTCAAG    +780
 D  R  Y  G  G  I  H  S  K  E  E  C  E  S  F  P  E  A  L  K   188

CCCGGCTGCAACTGGCGCTTCGACTGgtacgttgctttgacataccggaacccaattcct    +840
                          Intron 3
 P  G  C  N  W  R  F  D  W                                    197 ccaaccccccccttttctccccaactccgggggtagtcggaatgtcgcgactgaccct      +900 atttcagGTTCCAAAACGCCGACAACCCGTCGGTCACCTTCCAGGAGGTGGCCTGCCCGT    +960
        F  Q  N  A  D  N  P  S  V  T  F  Q  E  V  A  C  P    214

CGGAGCTCACGTCCAAGAGCGGCTGCTCCCGTTAAGAGGGAAGAGAGGGGGCTGGAAGGA   +1020
t25
 S  E  L  T  S  K  S  G  C  S  R  *                            225

CCGAAAGATTCAACCTCTGCTCCTGCTGGGGAAGCTCGGGCGCGAGTGTGAAACTGGTGT   +1080
t85

AAATATTGTGGCACACACAAGCTACTACAGTCCGTCTCGCCGTCCGGCTAACTAGCCTTG   +1140
t145

CTGCGGATCTGTCCATCTTCGGTCCGAACTGTCCGTTGCTGTTTTGGCTCGGTGCCTCAT   +1200
t205

CTTCTCCCAACCTAGTCAAGAATGAATCGTGAGAGAGGCTGAGAGAGATAAGATCGACTT   +1260
t265

CAGAAATCCAGGGTTGAAAGCAATAAAAAAAAATTCCTGTGGGATGAATATCTCGTGATGC  +1320
polyA site

AACGACCCTCCTAGGAAACCTTGACGAAATTTGCTGACGGCAAATTCTTCAAAGACTCGT   +1380
t385

TAACCGGTCGCCCGTAGTGGTCCTGTTGCCCCAATCCGTTTGTGTTGAAATGACATTGCG   +1440
t445

CGTAACGCCGGACTCATATCAACTGCGTACCGAAAGCCAATCCCTCCCCAAACACGCCCT   +1500
t505

CTCTAATAAGCTCTCCCAAACAAGACCTCTTGAGACAGAAAATACGCCCAGATGCTGAGG   +1560
t565

ACTTGACAAGCCGGGGGGGGGGGGGCTTGTCAAGTGCAAAAACTTGCCCATTTCATGC     +1620
t625

TGGTATCAAAAAAACAAAAAAAAAAAAAAAACATTTCAAGTCGCGGATGCCCCATTTACAT  +1680
t685

TGCTTGCGTGCGCCAATAGAAACTTGCAACACGTCAGTGTCATCTTGCACGCCTTGG      +1737
t742
```

SEQ ID No. 14
 C1-EG5 "25 kD" Protein sequence

MHLSATTGFL ALPALALAQL SGSGQTTRYW DCCKPSCAWP GKGPSSPVQA CDKNDNPLND

GGSTRSGCDA GGSAYMCSSQ SPWAVSDELS YGWAAVKLAG SSESQWCCAC YELTFTSGPV

-continued

AGKKMIVQAT NTGGDLGDNH FDLAIPGGGV GIFNACTDQY GAPPNGWGDR YGGIHSKEEC

ESFPEALKPG CNWRFDWFQN ADNPSVTFQE VACPSELTSK SGCSR

SEQ ID No. 6:
C1-EG6 "43 kD" (Family 6) was obtained by PCR based on "43 kD Endo" protein sequencing and family 6 cellulases homology analysis.

```
-2508        GGATCCACACCTACCATACCGGATAGTATGCTACCCAAGTGACATAGG  -2461

GTTGGTAAAGTAATACGAGAACTCAGAGAGCACTGCCCATATGGCTCGCCAATGACCTCA  -2401

AGTGCCAGGTCAGCTTTGCGAGACAGACCTGAGCGCGTCGGATGTGTGACATGGAACGCG  -2341

CCGGATCGCCTTGTTGATTAATTATAGGGAAGTAGCGAGGAAGGTTTCAGCAATTGACGT  -2281

GAGCGTACATTAAAAGCTGTATGATTTCAGGAAGACGAGCCATGGACCAGGTTTCAAGGC  -2221

TGAATGGCTTGACGACTTAAGCACCGAACGAGGAATGAAAGAATGAAAAGTGGGGGATCA  -2161
creA

TTCTGGCCCCTCCTCGTATGTCGAGTGTTAAAGAAGGCGGTTCTACGGAGGACCTAAAGA  -2101

GCTCCAATTTGCTCTGTTGAGCTTAAGCCACATATCTCAAGATGAATACATGTCAGGCAT  -2041

AGTCACCCTGATCTTGTTCATCAGTCCACACACTTTTCAGTTCAGCATGTTGATTCCTCA  -1981

TCCATATCACTTTCCATTACTATCTCTTTATGTCCTTGGTCAAGACTCCAAGGAACCGAT  -1921

AGGTGAGCATCGGTGAGGCTCCCTCAAGGTACCAAAGTAGCCATCATCACCGAGGTCTGG  -1861

GAATGGCGCCGTGCCCGATCTGAGTCCTCCAACTCCACGGTACGACGACAGCACGTCACA  -1801

TTGACGCACCACGGTTGAACAAGCAGAGAGGGACACGTCTTGCTACGCGAATCCTGGCAC  -1741

TGGATGGAGACGCGTGTGAGCAGGTTTCCGGAACCATGACGGCCTGGTCCGGCTTCTCGA  -1681

ACAAAGAAGTGGAACACAAAAAGAACCGAAACGGAAACGCAGGCACGGCATCGACGACCG  -1621

GATTGTCCCACGGGGACCTCGGCCAGTCAAGCGTTGCCCTGGCCGTCAGCTCCCTGGCGA  -1561

CGGGGATTCAGCACATCTCACGTTATAGGCGACCTCATCCCCCTTCCGTCTTGTGCGGTC  -1501

GTTGCTCCGTGCCGAGTACCCAGGCGTGCCGGGGCCTTTAGCCGGGGCGGAATCAGAGTC  -1441
creA

AAGATGCGGCCGAATTGGACGGCAGACGAAGTTTCGTAGAGGGTCATGATCGGCACTGAC  -1381

GACACCCACCCCTGCGTGATCCCGTGGCCCTGGGCTGGGAATTGCCGGCTAATAATCTAC  -1321

GGCTTAATAGATATGCACTTTGCACGCGGTGCAGATAAATAAGCTGTGGTTTCAAACACT  -1261

GGCCTCCGTACTTTACCCACCAACTGCCGCTTAGCGCCGGGACCTGAGTCTTGGGAGTGC  -1201

GCGGAGCGGCAGCCACCTCGGGTTAGCGTACACACGACGGCTGCATGCGGGGATGCCGCG  -1141
creA

TGCATGGCTTCATAGTGTACGACAGACCGTCAAGTCCAAATCTGGGTGATGCTTGATGAG  -1081
creA

ATGACAGCGAGCCCCGTCGGCGGCACCCCGGCTATGCATCGCGAATTGACAACACTCTCA  -1021

GCTCTATTGCGACCCATCGGATAAAAGAAGAAGAAAAAAATGGACCTTGAGTACGGGCGT   -961

CAGAAACCAAAAAAAAACTCCGGAACCAAATATGTCGGGCATGGCCGGGGTGAACGACCG   -901

CTACTCCCCGTTCCCTTCTTCGCAAACAGAACGCTACAGAGGGTTTTCTGGTTTGTCAAA   -841

GAGTTCGGAGGTCCTCTGCTCCGCGAATGCGTGGTGAACCCACCAGCAGCCATTGTTCTT   -781

GCATGCGTGGCGGACCGTTAGCCGCTGATCGACATGGCGAGCTTCCCACCTCAGACCTGG   -721
creA

AGCAGACGGTTGCGAGGAGCAAGGGGCTGCCCTCCCCCTGACGGTCGGACCCCAATGACT   -661
```

-continued

```
TCCCCAAACGGGGACATCGAGGGTCGTGCATGATGGTGGAAAGTAGTTGCAGTATGGGAA      -601

GTACCCCGGGTTGCCAGGAACCGTTGTTCGGCCCCCCACATTTTCTCTCTGCCATGTCAA      -541

CTGTGTGTCGTTCGAGAGTTCCTGGCTCCGGCCCCCCGTCCAATTCCCTAACGGGACCGC      -481
creA

GGGGCATCGCCTGTAACTAACTTCCAAATGAAGCCGGATATGAGGGAGGGAGATTGGATC     -421

TGGCAAGCCAGCCATTCGCTGCGATCGGCACTCGTCCGTCAGCCCCGCAGTCCATATCCC     -361
areA

CAAAGGCAACTGCTCGGCGCGGCTCAAGTCTTCTTCGGAACGTCCAGCCCGAAGGCGCGC      -301

GCCAGCACCGGCCCTATGTTCCTGATTGCGATCCTCGATCTCCAGAGACGGGTCACCTCG      -241

CCTCGAGGACGGTGCAGGGGCATCGGCTTCGCTTCCTAGAGCTCCGGGCTGTGTGTGGTC     -181

AAGGGGAGAAGGCGGCGGCGCCAAGGTGCGTCTCGGCGCACTCACCCATCGCCTTTACCC    -121

CCCTCCCCCCCAGTATATAAAAGATGGCCATCGTCTCCTCGTCTGCTTGGGAAGAAAGGA     -61

TCTCTCGACCATGCACCACAGCCTAGCTCTAACCCAGCTTGTCGTGTGTTGTTGCCCAGC       -1
transc.ini.

ATGAAGTTCGTGCAGTCCGCCACCCTGGCGTTCGCCGCCACGGCCCTCGCTGCGCCCTCG     +60
Putative Signal Seq
 M   K   F   V   Q   S   A   T   L   A   F   A   A   T   A   L   A   A   P   S     20

CGCACGACTCCCCAGAAGCCCCGCCAGGCCTCGGCGGGCTGCGCGTCGGCCGTGACGCTC    +120
 R   T   T   P   Q   K   P   R   Q   A   S   A   G   C   A   S   A   V   T   L      40

GATGCCAGCACCAACGTGTTCCAGCAGTACACGCTGCACCCCAACAACTTCTACCGTGCC    +180
 D   A   S   T   N   V   F   Q   Q   Y   T   L   H   P   N   N   F   Y   R   A      60

GAGGTCGAGGCTGCCGCCGAGGCCATCTCCGACTCGGCGCTGGCCGAGAAGGCCCGCAAG    +240
 E   V   E   A   A   A   E   A   I   S   D   S   A   L   A   E   K   A   R   K      80

GTCGCCGACGTCGGTACCTTCCTGTGGCTCGACACCATCGAGAACATTGGCCGGCTGGAG    +300
 V   A   D   V   G   T   F   L   W   L   D   T   I   E   N   I   G   R   L   E     100

CCCGCGCTCGAGGACGTGCCCTGCGAGAACATCGTGGGTCTCGTCATCTACGACCTCCCG    +360
 P   A   L   E   D   V   P   C   E   N   I   V   G   L   V   I   Y   D   L   P     120

GGCCGTGACTGCGCGGCCAAGGCCTCCAACGGCGAGCTCAAGGTCGGCGAGCTCGACAGG    +420
 G   R   D   C   A   A   K   A   S   N   G   E   L   K   V   G   E   L   D   R     140

TACAAGACCGAGTACATCGACgtgagttaaccctttgtggccccttcttttcccccgag    +480
                    Intron 1
 Y   K   T   E   Y   I   D                                                         147 agagcgtctggttgagtggggttgtgagagagaaaatggggcgagcttaaagactgacgt    +540 gttggctcgcagAGATCGCCGAGATCCTCAAGGCCCACTCCAACACGGCCTTCGCCCTCG   +600
             K   I   A   E   I   L   K   A   H   S   N   T   A   F   A   L        163

TCATCGAGCCCGACTCGCTCCCCAACCTGGTCACCAATAGCGACCTGCAGACGTGCCAGC    +660
 V   I   E   P   D   S   L   P   N   L   V   T   N   S   D   L   Q   T   C   Q     183

AGAGCGCTTCCGGCTACCGCGAGGGTGTCGCCTATGCCCTCAAGCAGCTCAACCTCCCCA    +720
 Q   S   A   S   G   Y   R   E   G   V   A   Y   A   L   K   Q   L   N   L   P     203

ACGTGGTCATGTACATCGATGCCGGCCACGGTGGCTGGCTCGGCTGGGACGCCAACCTCA    +780
 N   V   V   M   Y   I   D   A   G   H   G   G   W   L   G   W   D   A   N   L     223

AGCCCGGCGCCCAGGAGCTCGCCAGCGTCTACAAGTCTGCTGGTTCGCCCTCGCAAGTCC    +840
 K   P   G   A   Q   E   L   A   S   V   Y   K   S   A   G   S   P   S   Q   V     243

GCGGTATCTCCACCAACGTGGCTGGTTGGAACGCCTGgtaagacactctatgtcccctc    +900
                                    Intron 2
 R   G   I   S   T   N   V   A   G   W   N   A   W                                 256 gtcggtcaatggcgagcggaatggcgtgaaatgcatggtgctgacctttgatcttttccc    +960 cctcctatagGGACCAGGAGCCCGGTGAGTTCTCGGACGCCTCGGATGCCCAGTACAACA   +1020
           D   Q   E   P   G   E   F   S   D   A   S   D   A   Q   Y   N          272

AGTGCCAGAACGAGAAGATCTACATCAACACCTTTGGCGCTGAGCTCAAGTCTGCCGGCA   +1080
 K   C   Q   N   E   K   I   Y   I   N   T   F   G   A   E   L   K   S   A   G     292
```

-continued

```
TGCCCAACCACGCCATCATCGACACTGGCCGCAACGGTGTCACCGGTCTCCGCGACGAGT  +1140
 M   P   N   H   A   I   I   D   T   G   R   N   G   V   T   G   L   R   D   E    312

GGGGTGACTGGTGCAACGTCAACGGCGCCGGCTTCGGTGTGCGCCCGACTGCCAACACTG  +1200
 W   G   D   W   C   N   V   N   G   A   G   F   G   V   R   P   T   A   N   T    332

GCGACGAGCTCGCCGACGCCTTCGTGTGGGTCAAGCCCGGTGGCGAGTCCGACGGCACCA  +1260
 G   D   E   L   A   D   A   F   V   W   V   K   P   G   G   E   S   D   G   T    352

GCGACTCGTCGGCGGCGCGCTACGACAGCTTCTGCGGCAAGCCCGACGCCTTCAAGCCCA  +1320
 S   D   S   S   A   A   R   Y   D   S   F   C   G   K   P   D   A   F   K   P    372

GCCCCGAGGCCGGTACCTGGAACCAGGCCTACTTCGAGATGCTCCTCAAGAACGCCAACC  +1380
 S   P   E   A   G   T   W   N   Q   A   Y   F   E   M   L   L   K   N   A   N    392

GCTCCTTCTAAGCTCCTCGACGGCTTCTTGCTGTCAGTCGCTCTGACGGTGGTGTGCTGG  +1440
t49
 P   S   F   *                                                                    395

TGGTGCCCCTGCTCCTGCTGCTGCTGCTCCGCGGGGAGGGGAGGCAACGAAAATGAAGTC  +1500
t109

CTGCTTCAAAACAAAACAGAAACAAGCGAGGCGCGGTGCAATGGTCGTGCGTTCGTCTTT  +1560
t169

TTTCATGTTCCCTTCTAGTGTAGTAGTTTGATAGTCGTACATAAGGGGTTTCAGAACCGT  +1620
t229

CTCTCTGTCTCGGTCTTTTTGCGAGTTGTTGCGACTCGTGATTATGGCCTTTGTTGCTCG  +1680
t289

TTGCGGCAGAGTAGAACCACAGCGTGTTGGGGTAGCAGCTTGCTCCGTAGGACGTAGGGA  +1740
t349

AACAACCTGAGACTCTGGAATTGCAGTCAGCCTGCGTCGCCCCTCTAGGAAACGAAGGGG  +1800
t409

AGAACCAGTAGTGGCTGCAGCTTACAAACGCGAGCATGGTGAACATCTCCGAGAAAAGGG  +1860
t469

AGGGATCC                                                      +1868
t477
    BamHI
```

SEQ ID No. 15
  C1-EG6 "43 kD" Protein sequence

```
MKFVQSATLA FAATALAAPS RTTPQKPRQA SAGCASAVTL DASTNVFQQY TLHPNNFYRA

EVEAAAEAIS DSALAEKARK VADVGTFLWL DTIENIGRLE PALEDVPCEN IVGLVIYDLP

GRDCAAKASN GELKVGELDR YKTEYIDKIA EILKAHSNTA FALVIEPDSL PNLVTNSDLQ

TCQQSASGYR EGVAYALKQL NLPNVVMYID AGHGGWLGWD ANLKPGAQEL ASVYKSAGSP

SQVRGISTNV AGWNAWDQEP GEFSDASDAQ YNKCQNEKIY INTFGAELKS AGMPNHAIID

TGRNGVTGLR DEWGDWCNVN GAGFGVRPTA NTGDELADAF VWVKPGGESD GTSDSSAARY

DSFCGKPDAF KPSPEAGTWN QAYFEMLLKN ANPSF
                                                              55
```

SEQ ID No. 7 (DNA) and SEQ ID No. 16 (Protein):
  *Chrysosporium* xylanase F (partial)

```
TGACCTTCTCCTCCTTCTCCCGAACAATAATAGATAATTACGAGCCGGTTCGAGGCTGAC    1

ATTGCGCGATTCTAGCGAGCCGCAATCAATTCAACTTTGCCAACGCCGACGCGGTTGTC   61
                   S   R   N   Q   F   N   F   A   N   A   D   A   V   V

AACTTTGCCCAGGCCAACGGCAAGCTCATCCGCGGCCACACCCTCCTCTGGCACTCTCAG  120
  N   F   A   Q   A   N   G   K   L   I   R   G   H   T   L   L   W   H   S   Q

CTGCCGCAGTGGGTGCAGAACATCAACGACCGCAACACCTTGACCCAGGTCATCGAGAAC  180
```

-continued

```
                   L P Q W V Q N I N D R N T L T Q V I E N

CACGTCACCACCCTTGTCACTCGCTACAAGGGCAAGATCCTCCACTGGGACGTCGTTAAC   240
 H  V  T  T  L  V  T  R  Y  K  G  K  I  L  H  W  D  V  V  N

GAGATCTTTGCCGAGGACGGCTCGCTCCGCGACAGCGTCTTCAGCCGCGTCCTCGGCGAG   300
 E  I  F  A  E  D  G  S  L  R  D  S  V  F  S  R  V  L  G  E

GACTTTGTCGGCATCGCCTTCCGCGCCGCCCGCGCCGCCGATCCCAACGCCAAGCTCTAC   360
 D  F  V  G  I  A  F  R  A  A  R  A  A  D  P  N  A  K  L  Y

ATCAACGACTACAGGTCGACA                                          420
 I  N  D  Y  R  S  T                                            —
```

SEQ ID No. 8 (DNA) and SEQ ID Nos. 17-18 (Protein):
C1-EG3 (Family 12) gene fragment obtained by PCR based on family 12 cellulases homology analysis.

```
GAATTCGGGGATTACGAGCTAATGATCTGgtcagttttttttttcttttt
          g  d  y  e  l  m  i  w tcttttcttcnctttttcttttcttttcctttctcctgttttattttctta            100 tccattgcttcgccctctttccttaaccctgctgactctctcttcttgtc aatgatactgtaatagGCTGGCGAGATTCGGCGACGTCTACCCCATCGGC             200
                  L  A  R  F  G  D  V  Y  P  I  G TCGTCCCAGGGCCACGTCAACGTGGCCGGCCAGGACTGGGAGCTGTGGAC
 S  S  Q  G  H  V  N  V  A  G  Q  D  W  E  L  W  T GGGCTTCAANGGNAACATGCGGGTCTACAGCTTCGTAGCGCCCANCCCC             299
 G  F  X  G  N  M  R  V  Y  S  F  V  A  P  X  P CGCAACAGNTTCAGCGCCAACGTCAAGGACTTCTTCAACTATCTCCAGTC
 r  n  x  f  s  a  n  v  k  d  f  f  n  y  l  q  s CAACCAGGGCTTCCCGGCCAGCAGCCAATACCTTCTCAAgtaaggagacga            400
 n  q  g  f  p  a  s  s  q  y  l  l  n?

gatctcgaacagcataccatatatgcgtgcggtacaagtgcactaacccccc ttttttcccgttcgcagtCTTCCAGTTCGGCACTG                            487
```

SEQ ID No. 9 (DNA) and SEQ ID No. 19 (Protein):
*Chrysosporium* cellobiohydrolase CBH1

```
                                                    45
       TTTNGGGCGCCGTCTTACTCCTACCTTGCACCGTGATCGGCCAGTCGCGCTGCGAGGGCG
   1    ?  G  A  V  L  L  P  C  T  V  I  G  Q  S  R  C  E  G

ACTCGTGCGGCGGTACCTACAGCACCGACCGCTATGCCGGCATCTGCGACCCCGACGGAT
  61   D  S  C  G  G  T  Y  S  T  D  R  Y  A  G  I  C  D  P  D  G
                                                      50

GCGACTTCAACTCGTACCGCCAGGGCAACAAGACCTTCTACGGCAAGGGCATGACGGTCG
 121   C  D  F  N  S  Y  R  Q  G  N  K  T  F  Y  G  K  G  M  T  V

ACACGACCAAGAAGATCACGGTCGTCACCCAGTTCCTCAAGAACTCGGCCGGCGAGCTCT
 181   D  T  T  K  K  I  T  V  V  T  Q  F  L  K  N  S  G  E  L
                                                    55

CCGAGATCAAGCGGTTCTACGTCCAGAACGGCAAGGTCATCCCCAACTCCGAGTCCACCA
 241   S  E  I  K  R  F  Y  V  Q  N  G  K  V  I  P  N  S  E  S  T

TCCCGGGCGTCGAGGGCAACTCCATCACCCAGGACTGGTGCGACCGCCAGAAGGCCGCCT
 301   I  P  G  V  E  G  N  S  I  T  Q  D  W  C  D  R  Q  K  A  A
                                                  60

TCGGCGACGTGACCGACTTCCAGGACAAGGGCGGCATGGTCCAGATGGGCAAGGCCCTCG
 361   F  G  D  V  T  D  F  Q  D  K  G  G  M  V  Q  M  G  K  A  L

CGGGGCCCATGGTCCTCGTCATGTCCATATGGGACGACCACGCCAGTCAACA
 421   A  G  P  M  V  L  V  M  S  I  W  D  D  H  A  S  ?
                                               65
```

We claim:

1. A mutant *Chrysosporium* strain comprising a nucleic acid sequence encoding a polypeptide of interest, said nucleic acid sequence being operably linked to a promoter sequence and optionally a secretion signal sequence, said mutant strain expressing said polypeptide of interest at a higher level than the corresponding non-mutant strain under the same conditions, wherein said mutant derived from *Chrysosporium lucknowense* is UV13-6 (VKM F-3632 D), NG7C-19 (VKM F-3633 D), or UV18-25 (VKM F-3631 D) or is derived from a *Chrysosporium lucknowense* strain of *C. lucknowense* strain C1 (VKM F-3500 D), UV13-6 (VKM F-3632 D), NG7C-19 (VKM F-3633 D), or UV18-25 (VKM F-3631 D).

2. A mutant *Chrysosporium* strain wherein said mutant is or is derived from a *Chrysosporium lucknowense* mutant strain selected from the group consisting of UV13-6 (VKM F-3632 D), NG7C-19 (VKM F-3633 D), and UV18-25 (VKM F-3631 D).

3. The mutant *Chrysosporium* strain of claim 2 wherein said mutant is or is derived from a *Chrysosporium lucknowense* mutant strain UV13-6 (VKM F-3632 D).

4. The mutant *Chrysosporium* strain of claim 2 wherein said mutant is or is derived from a *Chrysosporium lucknowense* mutant strain NG7C-19 (VKM F-3633 D).

5. The mutant *Chrysosporium* strain of claim 2 wherein said mutant is or is derived from a *Chrysosporium lucknowense* mutant strain UV18-25 (VKM F-3631 D).

6. The mutant *Chrysosporium* strain of claim 2, 3, 4 or 5 wherein said mutant strain expresses a polypeptide of interest at a higher level than the corresponding original mutant strain under the same conditions.

* * * * *